US009260705B2

(12) United States Patent
Baidyaroy et al.

(10) Patent No.: US 9,260,705 B2
(45) Date of Patent: Feb. 16, 2016

(54) CELLOBIOHYDROLASE VARIANTS

(71) Applicant: Codexis, Inc., Redwood City, CA (US)

(72) Inventors: Dipnath Baidyaroy, Fremont, CA (US); Louis Clark, San Francisco, CA (US); David Elgart, San Mateo, CA (US); Rama Voladri, Redwood City, CA (US); Xiyun Zhang, Fremont, CA (US)

(73) Assignee: Codexis, Inc., Redwood City, CA (US)

( * ) Notice: Subject to any disclaimer, the term of this patent is extended or adjusted under 35 U.S.C. 154(b) by 0 days.

(21) Appl. No.: 14/588,231

(22) Filed: Dec. 31, 2014

(65) Prior Publication Data

US 2015/0197736 A1 Jul. 16, 2015

Related U.S. Application Data

(62) Division of application No. 13/549,300, filed on Jul. 13, 2012, now Pat. No. 8,945,903.

(60) Provisional application No. 61/526,361, filed on Aug. 23, 2011.

(51) Int. Cl.

| | |
|---|---|
| ***C12N 9/42*** | (2006.01) |
| ***C12N 1/20*** | (2006.01) |
| ***C12N 15/00*** | (2006.01) |
| ***C07H 21/04*** | (2006.01) |
| ***C12P 19/14*** | (2006.01) |
| ***C12P 19/02*** | (2006.01) |
| ***C12N 15/80*** | (2006.01) |
| ***C12P 7/14*** | (2006.01) |
| ***C12P 7/16*** | (2006.01) |
| ***C12P 7/18*** | (2006.01) |
| ***C12P 7/20*** | (2006.01) |
| ***C12P 7/46*** | (2006.01) |
| ***C12P 7/48*** | (2006.01) |
| ***C12P 7/54*** | (2006.01) |
| ***C12P 7/56*** | (2006.01) |
| ***C12P 7/58*** | (2006.01) |
| ***C12P 13/14*** | (2006.01) |

(52) U.S. Cl.

CPC .............. *C12N 9/2437* (2013.01); *C12N 15/80* (2013.01); *C12P 7/14* (2013.01); *C12P 7/16* (2013.01); *C12P 7/18* (2013.01); *C12P 7/20* (2013.01); *C12P 7/46* (2013.01); *C12P 7/48* (2013.01); *C12P 7/54* (2013.01); *C12P 7/56* (2013.01); *C12P 7/58* (2013.01); *C12P 13/14* (2013.01); *C12P 19/02* (2013.01); *C12P 19/14* (2013.01); *C12Y 302/01091* (2013.01); *Y02E 50/16* (2013.01)

(58) Field of Classification Search

CPC .......................................................... C12P 7/14
USPC .................... 435/209, 252.3, 320.1; 536/23.2
See application file for complete search history.

(56) References Cited

U.S. PATENT DOCUMENTS

| | | | |
|---|---|---|---|
| 6,117,679 | A | 9/2000 | Stemmer |
| 6,376,246 | B1 | 4/2002 | Crameri et al. |
| 6,586,182 | B1 | 7/2003 | Patten et al. |
| 7,783,428 | B2 | 8/2010 | Gustafsson et al. |
| 7,923,236 | B2 | 4/2011 | Gusakov et al. |
| 2004/0197890 | A1 | 10/2004 | Lange et al. |
| 2007/0238155 | A1 | 10/2007 | Gusakov et al. |
| 2008/0220990 | A1 | 9/2008 | Fox |
| 2009/0280105 | A1 | 11/2009 | Gusakov et al. |
| 2009/0311755 | A1 | 12/2009 | Harris et al. |
| 2009/0312196 | A1 | 12/2009 | Colbeck et al. |
| 2010/0267089 | A1 | 10/2010 | Yang et al. |
| 2010/0304437 | A1 | 12/2010 | Garner et al. |
| 2011/0167514 | A1 | 7/2011 | Brover et al. |
| 2012/0135500 | A1 | 5/2012 | Aehle et al. |
| 2014/0322796 | A1 | 10/2014 | Mitchell |

FOREIGN PATENT DOCUMENTS

| | | | |
|---|---|---|---|
| WO | 03/000941 | A2 | 1/2003 |
| WO | 2006/074005 | A2 | 7/2006 |
| WO | 2008/025164 | A1 | 3/2008 |
| WO | 2008/095033 | A2 | 8/2008 |
| WO | 2008/153903 | A2 | 12/2008 |
| WO | 2008/153925 | A2 | 12/2008 |
| WO | 2009/042871 | A1 | 4/2009 |
| WO | 2009/059175 | A2 | 5/2009 |
| WO | 2009/085859 | A2 | 7/2009 |
| WO | 2010/066411 | A2 | 6/2010 |
| WO | 2010/088387 | A1 | 8/2010 |
| WO | 2010/088463 | A2 | 8/2010 |
| WO | 2010/118058 | A2 | 10/2010 |
| WO | 2010/120557 | A1 | 10/2010 |
| WO | 2010/141325 | A1 | 12/2010 |
| WO | 2010/141779 | A1 | 12/2010 |
| WO | 2011/050037 | A1 | 4/2011 |
| WO | 2011/080317 | A2 | 7/2011 |
| WO | 2011/098580 | A1 | 8/2011 |
| WO | 2011/143632 | A2 | 11/2011 |
| WO | 2012/044915 | A2 | 4/2012 |
| WO | 2012/149403 | A1 | 11/2012 |
| WO | 2013/028278 | A1 | 2/2013 |

OTHER PUBLICATIONS

PCT Written Opinion, Sep. 24, 2012.

Federova, et al., "Genomic islands in the pathogenic filamentous fungus *Aspergillus fumigates*," PLoS Genetics, 4(4), entry e1000046.

(Continued)

*Primary Examiner* — Tekchand Saidha

(74) *Attorney, Agent, or Firm* — Codexis, Inc.

(57) ABSTRACT

The present invention relates to cellobiohydrolase variants having improved thermostability in comparison to wild-type CBH2a.

17 Claims, 4 Drawing Sheets

(56) References Cited

OTHER PUBLICATIONS

Fox, R., "Directed molecular evolution by machine learning and the influence of nonlinear interactions," J. Theor. Bioi., 234(2):187-199, 2005.

Fox, R., et al., "Optimizing the search algorithm for protein engineering by directed evolution," Protein Eng., 16 (8):589-597, 2003.

Gusakov, et al., "Design of highly efficient cellulose mixtures for enzymatic hydrolysis of cellulose," Biotechnology and Bioengineering, 2007 97(5): 1028-1038.

Gusakov, et al., "Purification, cloning and characterization of two forms of thermostable and highly active cellobiohydrolase I (Cel7A) produced by the industrial strain of *Chrysosporium lucknowense*," Enzyme and Microbial Technology, 2005 36(1): 57-69.

```
                        1                                                50
            CBH2a    (1) --------------------------------------------------
     XP_001226566.1  (1) --------------------------------------------------
         CBI58887.1  (1) --------------------------------------------------
        XP_956581.1  (1) --------------------------------------------------
     XP_001903893.1  (1) --------------------------------------------------
            CBH2b    (1) APVIEERQNCGAVWTQCGGNGWQGPTCCASGSTCVAQNEWYSQCLPNSQV
         CBY00792.1  (1) --------------------------------------------------
     XP_001806560.1  (1) --------------------------------------------------
     XP_001931623.1  (1) --------------------------------------------------
     XP_003300842.1  (1) --------------------------------------------------
     XP_003028483.1  (1) --------------------------------------------------
        XP_362054.1  (1) --------------------------------------------------
          Consensus  (1)

                         51                                              100
            CBH2a    (1) ---------------------------APSRTTPQ-KPRQ----ASAGCA
     XP_001226566.1  (1) ---------------------------APSPTTKQ-KPRQ----AGGACA
         CBI58887.1  (1) ---------------------------APSTPTSQDKPRA----IQAGCA
        XP_956581.1  (1) ---------------------------APSTPTLQEKPRE----VQAGCA
     XP_001903893.1  (1) ---------------------------APSPTTQD-KPTK----RQAGCA
            CBH2b   (51) TSSTTPSSTSTSQRSTSTSSSTTRSGSSSSSSTTPPPVSSPVTSIPGGAT
         CBY00792.1  (1) ---------------------------LPSPTEQGPITAR---AAAAACA
     XP_001806560.1  (1) ---------------------------APSPVENGPITARAVGAAAAACA
     XP_001931623.1  (1) ---------------------------APTPADNGPLAAR------AACS
     XP_003300842.1  (1) ---------------------------APTPDDNGPLAAR------AACS
     XP_003028483.1  (1) ---------------------------SPANRKRR--------------P
        XP_362054.1  (1) ---------------------------SPSRTVKS-QPGQ----AAAGCS
          Consensus (51)                            APSPTT    P        AGCA

                         101                                             150
            CBH2a   (19) SAVTLDASTNVFQQYTLHPNNFYRAEVEAAAEA-ISDSALAEKARKVADV
     XP_001226566.1 (19) SAVTLDASTNVFKEYTLHPNSFYRAEVEAAVEQ-ITDSSLAAKAAKVADV
         CBI58887.1 (20) SAVTLDASTNVWKKYTLHANKFYRTEVEAAVQA-ISDSSLASQAAKVADV
        XP_956581.1 (20) SAVTLDASTNVWKKYTLHANKFYRTEVEAAVAA-ISDSSLAAKAAKVANV
     XP_001903893.1 (19) SAVSLNAQTNVFKQYTLHANNFYRKEIEELAIPNLSDPSLEAAARKVADT
            CBH2b  (101) STASYSG--NPFSGVRLFANDYYRSEVHNLAIP-SMTGTLAAKASAVAEV
         CBY00792.1 (21) TPVTLSG--NPFASRSIYANKFYSSEVAAAAAA-MTDTALASAAAKVANV
     XP_001806560.1 (24) TPVTLSG--NPFASRQIYANKFYSSEVSAAAAA-MTDSALAASATKID--
     XP_001931623.1 (18) SPVTLTG--NPFTGRKIYANKFYADEVNKAAAA-MTDSTLAAAAKKVADV
     XP_003300842.1 (18) SPVTLSG--NPFTGRKIYANKFYAAEVNKAAAA-ISDATLAAAAKKVADV
     XP_003028483.1 (10) -AVTLEG--NPFESYTLHANSHYSSLVEAAIGN-LSDSSLEPAAQVVKET
        XP_362054.1 (19) SAVTLDASTNVFSKYTLHPNSFYRAEVEAAAEA-ISDSTLKAQALKVADV
          Consensus(101) SAVTLDA TNVF  YTLHANKFYRAEVEAAAAA ISDSSLAAAA KVADV
```

*FIG. 1A*

```
                          151                                              200
          CBH2a    (68)   GTFLWLD-----------TIENIGRLEPALEDVPCENIVGLVIYDLPGRD
 XP_001226566.1    (68)   GTFLWLD-----------TIENIGKLEPALEDVPCENILGLVIYDLPGRD
     CBI58887.1    (69)   GSFLWLD-----------TIANIGKLEPALEDVPCDHILGLVIYDLPGRD
    XP_956581.1    (69)   GSFLWLD-----------SIENIGKLEPALEDVPCDHILGLVIYDLPGRD
 XP_001903893.1    (69)   GSFVWLD-----------TIANVDRLEPALAEVPCNEILGVVVYDLPGRD
          CBH2b   (148)   PSFQWLDRNVTIDTLMVQTLSQVRALNKAGANPP--YAAQLVVYDLPDRD
     CBY00792.1    (68)   GTFLWID-----------TRAKIAVVEDGIKDVPCDQIAALVIYDLPGRD
 XP_001806560.1    (69)   ------------------------IVEDTIKDVPCDQIAALVIYDLPGRD
 XP_001931623.1    (65)   GTYFWID-----------TRAKIAMIEDELKNVSCDQIAAFVIYDLPGRD
 XP_003300842.1    (65)   GTYFWID-----------TRAKIAMVEDELKNVSCDQIAAFVIYDLPGRD
 XP_003028483.1    (56)   GTFLWLD-----------TISTIETFEGYLQETGENEIFGVVIYDLPGRD
    XP_362054.1    (68)   GSFLWID-----------TISAISRIEPGVSDQPCDHILGLVIYDLPGRD
      Consensus   (151)   GTFLWLD           TIANIGKLEPAL DVPCDQILGLVIYDLPGRD

                          201                                              250
          CBH2a   (107)   CAAKASNGELKVG-ELDRYKTEYIDKIAEILKAHSNTAFALVIEPDSLPN
 XP_001226566.1   (107)   CAAKASNGELKVG-EIEKYKTEYIDKIVTILKANPNTAFALVIEPDSLPN
     CBI58887.1   (108)   CAAKASNGELKVG-ELNKYKTEYIDVIVKILKAHPKTAFALVIEPDSLPN
    XP_956581.1   (108)   CAAKASNGELAVG-ELSRYKTEYIDAIVKILKAHPKTAFALVIEPDSLPN
 XP_001903893.1   (108)   CAAKASNGELKVG-ELNRYKTEFIDRIASILKAHPNTAVALVIEPDSLPN
          CBH2b   (196)   CAAAASNGEFSIANGGAANYRSYIDAIRKHIIEYSDIRIILVIEPDSMAN
     CBY00792.1   (107)   CAAKASNGELAVG-ELDIYKREYIDPIVAIFKKYPNTAIALVIEPDSLPN
 XP_001806560.1    (95)   CAAKASNGELPVG-SLETYKTEYIDPIVAIFKKYPNIAIALVIEPDSLPN
 XP_001931623.1   (104)   CAAKASNGELAVG-QLDVYKTEYIDPIVAIFKKYPNTAISLIIEPDSLPN
 XP_003300842.1   (104)   CAAKASNGELAVG-QLDVYKTEYIDPIVAIFKKYPNTAISLIIEPDSLPN
 XP_003028483.1    (95)   CAAKASNGELAVG-ELDRYKSEYIDPIVAIIKNNPDIAIAAIIEPDSLPN
    XP_362054.1   (107)   CAAKASNGELKVG-ELAKYKSQYIDPIAALLKKYNNHAFALLIEPDSLPN
      Consensus   (201)   CAAKASNGELAVG ELDRYKTEYIDPIVAILK YPNTAIALVIEPDSLPN

                          251                                              300
          CBH2a   (156)   LVTNSDLQTCQQSASGYREGVAYALKQLNLPNVVMYIDAGHGGWLGWDAN
 XP_001226566.1   (156)   LVTNIDLTTCQESADGYHEGVAYALKSLNLPNVVMYLDAGHGGWLGWDAN
     CBI58887.1   (157)   LVTNADVQACKDSASGYRDGVAYALKNLNLPNVVMYIDAGHGGWLGWDAN
    XP_956581.1   (157)   LVTNSDLQTCKDSASGYRDGVAYALRNLNLPNVVMYIDAGHGGWLGWDAN
 XP_001903893.1   (157)   LVTNSDVQACRNSAAGYRDGVAYALKTLNLPNVVQYIDAGHGGWLGWDAN
          CBH2b   (246)   MVTNMNVAKCSNAASTYHELTVYALKQLNLPNVAMYLDAGHAGWLGWPAN
     CBY00792.1   (156)   LVTNAKLQTCQDSASGYREGVAYALKQFNMPNIAMYIDAGHGGWLGWNDN
 XP_001806560.1   (144)   LVTNANLQTCKDSAEGYRKGVAYALKSLNLPNIAMYIDAGHGGWLGWNDN
 XP_001931623.1   (153)   LVTNANVQACQQSASGYRDGVAYALKQLNLPNIAMYIDAGHGGWLGWDDN
 XP_003300842.1   (153)   LVTNANLQACQQSASGYREGVAYALKQLNLPNIAMYIDAGHGGWLGWDDN
 XP_003028483.1   (144)   LVTNSDLTTCQNSASGYEEGVAYALSSLDLPNVVQYVDAGHGGWLGWDAN
    XP_362054.1   (156)   LVTNSDLSACQQSAAGYRDGVAYALKTLNLPNVVMYIDAGHGGWLGWNDN
      Consensus   (251)   LVTNADLQTCQQSASGYREGVAYALKQLNLPNVVMYIDAGHGGWLGWDAN
```

FIG. 1B

```
                           301                                               350
         CBH2a   (206) LKPGAQELASVYKSAGSPSQVRGISTNVAGWNAWDQEPGEFSDASDAQYN
XP_001226566.1   (206) LKPGAEELAKAYKNAGSPSQFRGIATNVAGWNQWDLSPGEFSDTSDAKYN
    CBI58887.1   (207) LKPGAQELAKAYKAAGSPKQVRGIATNVAGWNQWDLSPGEFSKASDAKYN
   XP_956581.1   (207) LKPGAQELAKAYKAAGSPKQVRGIATNVAGWNQWDLTPGEFSKASDAKYN
XP_001903893.1   (207) LKPGAEELAKAYKAAGSPKQFRGIATNVAGWNAWDLSPGEFSSASDAKYN
         CBH2b   (296) IQPAAELFAGIYNDAGKPAAVRGLATNVANYNAWSIASAPSYTS-P---N
    CBY00792.1   (206) LKPGAKELATVYKNAGSPKSVRGIATNVAGWNAWDQTPGEFSTATDAQWN
XP_001806560.1   (194) LKPGAKELATVYKDAGSPKQVRGVSTNVAGWNAYDLSPGEFSKATDAQYN
XP_001931623.1   (203) IKPGAKELATVYKAAGSPKQVRGISTNIAGWNAWDLSPGEFANSADGKYN
XP_003300842.1   (203) IKPGAKELATVYKNAGSPKSVRGISTNIAGWNAFDLSPGEFANSADGKYN
XP_003028483.1   (194) LKPGAEELAKVYKAAGSPSNVRGISTNVAGWNAWSKNPGEFENAPDGQYN
   XP_362054.1   (206) LKPGAEELAKAYKAAGSPKQFRGFATNVAGWNAWDLTPGEFSSASDAQWN
     Consensus   (301) LKPGA ELAKVYKAAGSPKQVRGIATNVAGWNAWDLSPGEFS ASDAKYN

                           351                                               400
         CBH2a   (256) KCQNEKIYINTFGAELKSAGMPNHAIIDTGRNG-VTGLRDEWGDWCNVNG
XP_001226566.1   (256) SCQNEKTYITTFGAALKTAGMPNHAIIDTGRNG-VSGLREEWGNWCNVKG
    CBI58887.1   (257) KCQNEKLYLDNFGPALKSAGMPNHAIVDTGRNG-VSGLREEWGNWCNVNG
   XP_956581.1   (257) KCQNEKLYLDNFGPALKSAGMPNHAIVDTGRNG-VSGLRQEWGNWCNVNG
XP_001903893.1   (257) SCQNERTYVNTFGQRLKAAGMPNHAIVDTGRNG-VQGLREEWGNWCNVDG
         CBH2b   (342) PNYDEKHYIEAFSPLLNSAGFPARFIVDTGRNGKQPTGQQQWGDWCNVKG
    CBY00792.1   (256) KAQNEKLYIELFSPELKSAGMPGQAIVDTGRNA-VTGLRREWGNWCNVNG
XP_001806560.1   (244) KAQNEKLFVSMFSPELKSAGMPGQAIIDTARNG-VTGLRKEWGDWCNVKG
XP_001931623.1   (253) KAQNEKLYIGLISPELVKNGMPGQAIVDTGRNG-VTGLRAEWG-------
XP_003300842.1   (253) KAQNEKLYVSLISPELVKNGMPGQAIVDTGRNG-VTGLRAEWGDWCNVNG
XP_003028483.1   (244) KCQDEQRYVTIFGDALSAAGFPNHAIVDTARNG-VQGLRDAWGDWCNVIG
   XP_362054.1   (256) KCQNEKIYVETFGPLLKNAGMPNHAIVDVGRNA-VQGLREEWGHWCNVNG
     Consensus   (351) KCQNEKLYI  FGP LKSAGMPNHAIVDTGRNG VTGLREEWG WCNVNG

                           401                                               450
         CBH2a   (305) AGFGVRPTANTGDELADAFVWVKPGGESDGTSDSSAARYDSFCGKPDAFK
XP_001226566.1   (305) AGFGIRPTADTGADLADAFVWVKPGGESDGTSDTSAVRYDSFCGKPDAYN
    CBI58887.1   (306) AGFGTRPTSTTGHDLADAFVWVKPGGESDGTSDSSATRYDSFCGKSDAYQ
   XP_956581.1   (306) AGFGVRPTSSTGHDLADAFVWVKPGGESDGTSDSSATRYDSFCGKSDAYQ
XP_001903893.1   (306) AGFGRPPSADTGLELADAFVWVKPGGESDGTSDSSAVRYDSFCGKPDAFQ
         CBH2b   (392) TGFGVRPTANTGHELVDAFVWVKPGGESDGTSDTSAARYDYHCGLSDALQ
    CBY00792.1   (305) AGFGVRPTSNTGSSLVDSFVWVKPGGESDGTSDPSATRYDSFCGKEDAFK
XP_001806560.1   (293) AGFGVRPTGNTGNTLVDAFVWVKPGGESDGTSDSSATRYDSFCGKDDAFK
XP_001931623.1   (295) ------------DCLVDSFVWGKPGGESDGTSDSSATRYDSFCGKSDAYK
XP_003300842.1   (302) AGFGVRPTTNTGSSLVDSFVWGKPGGESDGTSDSSATRYDSFCGKSDAYK
XP_003028483.1   (293) AGIGVRPTADTGEELADAFVWVKPAGESDGTSDSSATRYDSMCGLDDAYK
   XP_362054.1   (305) AGFGVRPTTSTGSSLTDALLWVKPGGESDGTSDTSATRYDSFCGMSDAYK
     Consensus   (401) AGFGVRPTA TG ELADAFVWVKPGGESDGTSDSSATRYDSFCGKSDAYK
```

*FIG. 1C*

| | | 451 475 |
|---|---|---|
| CBH2a | (355) | PSPEAGTWNQAYFEMLLKNANPSF- |
| XP_001226566.1 | (355) | PSPEAGQWNQAYFEDLVKNAKPAF- |
| CBI58887.1 | (356) | PSPEAGNWNQEYFEMLLKNAKPAF- |
| XP_956581.1 | (356) | PSPEAGSWNQDYFEMLVKNAKPSF- |
| XP_001903893.1 | (356) | PSPEAGAWHQEYFEMLLRNSNPSLL |
| CBH2b | (442) | PAPEAGQWFQAYFEQLLTNANPPF- |
| CBY00792.1 | (355) | PSPEAGQWNQAYFEMLVKNAKPAF- |
| XP_001806560.1 | (343) | PSPEAGQWHQAYFEELVKNAKPAL- |
| XP_001931623.1 | (333) | PSPEAGQWNQAYFEMLVKNAKPAF- |
| XP_003300842.1 | (352) | PSPEAGQWNQPYFEMLVKNAKPAF- |
| XP_003028483.1 | (343) | PSPEAGAWNQPYFEELLKNANPSLA |
| XP_362054.1 | (355) | PSPEAGQWNQDYFEMLLRNAKPQF- |
| Consensus | (451) | PSPEAGQWNQAYFEMLLKNAKPAF |

FIG. 1D

CELLOBIOHYDROLASE VARIANTS

CROSS-REFERENCES TO RELATED APPLICATIONS

This application is a divisional application of U.S. application Ser. No. 13/549,300, filed Jul. 13, 2012, which claims benefit of priority of U.S. Provisional Application No. 61/526,361, filed Aug. 23, 2011. The entire content of each application is incorporated herein by reference.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 90834-922453_ST25.TXT, created on Dec. 31, 2014, 88,901 bytes, machine format IBM-PC, MS-Windows operating system, is hereby incorporated by reference.

FIELD OF THE INVENTION

This invention relates to cellobiohydrolase variants and their use in the production of fermentable sugars from cellulosic biomass.

BACKGROUND OF THE INVENTION

Cellulosic biomass is a significant renewable resource for the generation of fermentable sugars. These sugars can be used as reactants in various metabolic processes, including fermentation, to produce biofuels, chemical compounds, and other commercially valuable end-products. While the fermentation of simple sugars such as glucose to ethanol is relatively straightforward, the efficient conversion of cellulosic biomass to fermentable sugars is challenging. See, e.g., Ladisch et al., 1983, *Enzyme Microb. Technol.* 5:82. Cellulose may be pretreated chemically, mechanically, enzymatically or in other ways to increase the susceptibility of cellulose to hydrolysis. Such pretreatment may be followed by the enzymatic conversion of cellulose to cellobiose, cello-oligosaccharides, glucose, and other sugars and sugar polymers, using enzymes that break down the β-1-4 glycosidic bonds of cellulose. These enzymes are collectively referred to as "cellulases."

Cellulases are divided into three sub-categories of enzymes: 1,4-β-D-glucan glucanohydrolase ("endoglucanase" or "EG"); 1,4-β-D-glucan cellobiohydrolase ("exoglucanase," "cellobiohydrolase," or "CBH"); and β-D-glucoside-glucohydrolase ("β-glucosidase," "cellobiase," or "BG"). See Methods in Enzymology, 1988, Vol. 160, p. 200-391 (Eds. Wood, W. A. and Kellogg, S. T.). These enzymes act in concert to catalyze the hydrolysis of cellulose-containing substrates. Endoglucanases break internal bonds and disrupt the crystalline structure of cellulose, exposing individual cellulose polysaccharide chains ("glucans"). Cellobiohydrolases incrementally shorten the glucan molecules, releasing mainly cellobiose units (a water-soluble β-1,4-linked dimer of glucose) as well as glucose, cellotriose, and cellotetrose. β-glucosidases split the cellobiose into glucose monomers.

Cellulases with improved properties for use in processing cellulosic biomass would reduce costs and increase the efficiency of production of biofuels and other commercially valuable compounds.

BRIEF SUMMARY OF THE INVENTION

In one aspect, the present invention provides recombinant cellobiohydrolase variants that exhibit improved properties. In some embodiments, the cellobiohydrolase variants are superior to naturally occurring cellobiohydrolases under conditions required for saccharification of cellulosic biomass.

In some embodiments, a recombinant cellobiohydrolase variant comprises at least about 70% (or at least about 75%, at least about 80%, at least about 85%, at least about 90%, at least about 95%, at least about 96%, at least about 97%, at least about 98%, or at least about 99%) sequence identity to SEQ ID NO:1 and comprises an amino acid substitution at one or more positions selected from 11, 13, 14, 15, 31, 39, 55, 69, 75, 81, 95, 109, 110, 113, 122, 159, 160, 199, 200, 204, 211, 230, 250, 265, 266, 272, 273, 297, 329, 340, 345, 346, and 361, wherein the position is numbered with reference to SEQ ID NO:1. In some embodiments, the variant comprises at least about 70% (or at least about 75%, at least about 80%, at least about 85%, at least about 90%, at least about 95%, at least about 96%, at least about 97%, at least about 98%, or at least about 99%) sequence identity to SEQ ID NO:1 and comprises an amino acid substitution at one or more positions selected from R11, A13, S14, A15, Q31, N39, S55, T69, T75, R81, V95, A109, K110, N113, D122, N159, S160, W199, L200, A204, Q211, S230, S250, N265, T266, K272, S273, G297, G329, A340, S345, F346, and T361, wherein the position is numbered with reference to SEQ ID NO:1. In some embodiments, the variant comprises one or more amino acid substitutions selected from R11I/N/T/V, A13P, 514L, A15F/I/S, Q31C, N39A/C/K/P/R/V, S55P, T69C, T75S, R81K, V95L, A109F/M, K110E/Q, N113L/R/T, D122S, N159H, S160C/L/M, W199M/T, L200P, A204Q/W, Q211K, S230A, S250C/P/V, N265H, T266L, K272A, S273A/D, G297M, G329P, A340S, S345E/P, F346A/K/N/S/Y, and T361E/K/Q. In some embodiments, a recombinant cellobiohydrolase variant is encoded by a polynucleotide that hybridizes at high stringency to the complement of SEQ ID NO:2 and comprises one or more amino acid substitutions as described herein.

In some embodiments, the variant comprises an amino acid substitution at one or more positions selected from V95 and S230. In some embodiments, the variant comprises one or more amino acid substitutions selected from V95L and S230A. In some embodiments, the variant comprises the amino acid sequence of SEQ ID NO:3.

In some embodiments, the variant comprises an amino acid substitution at position F346. In some embodiments, the variant comprises the amino acid substitution F346Y. In some embodiments, the variant comprises the amino acid sequence of SEQ ID NO:4.

In some embodiments, the variant comprises an amino acid substitution at position S250. In some embodiments, the variant comprises the amino acid substitution S250P. In some embodiments, the variant comprises the amino acid sequence of SEQ ID NO:5.

In some embodiments, the variant comprises an amino acid substitution at one or more positions selected from A15, N39, N113, A204, S250, S273, and A340. In some embodiments, the variant comprises one or more amino acid substitutions selected from A15I, N39C, N113R, A204W, S250V, S273D, and A340S. In some embodiments, the variant comprises the amino acid sequence of SEQ ID NO:6.

In some embodiments, the variant comprises an amino acid substitution at one or more positions selected from A15, N39, K110, A204, S250, and A340. In some embodiments, the variant comprises one or more amino acid substitutions selected from A15S, N39A, K110Q, A204W, S250P, and A340S. In some embodiments, the variant comprises the amino acid sequence of SEQ ID NO:7.

In some embodiments, the variant comprises an amino acid substitution at one or more positions selected from A15, N39, N113, A204, T266, and S345. In some embodiments, the variant comprises one or more amino acid substitutions selected from A15I, N39A, N113L, A204W, T266L, and S345E. In some embodiments, the variant comprises the amino acid sequence of SEQ ID NO:8.

In some embodiments, the variant comprises an amino acid substitution at one or more positions selected from A15, S55, A204, Q211, N265, and A340. In some embodiments, the variant comprises one or more amino acid substitutions selected from A15I, S55P, A204W, Q211K, N265H, and A340S. In some embodiments, the variant comprises the amino acid sequence of SEQ ID NO:9.

In some embodiments, a recombinant cellobiohydrolase variant comprises at least about 70% (or at least about 75%, at least about 80%, at least about 85%, at least about 90%, at least about 95%, at least about 96%, at least about 97%, at least about 98%, or at least about 99%) sequence identity to SEQ ID NO:1 and comprises an amino acid substitutions at positions 15 and 204, wherein the positions are numbered with reference to SEQ ID NO:1. In some embodiments, the amino acid residue at position 15 is alanine (A15) and the amino acid residue at position 204 is alanine (A204). In some embodiments, the amino acid residue at A15 is replaced with phenylalanine, isoleucine, or serine (A15F/I/S) and the amino acid residue at A204 is replaced with glutamine or tryptophan (A204Q/W). In some embodiments, the variant further comprises a mutation at position 340, wherein the position is numbered with reference to SEQ ID NO:1. In some embodiments, the amino acid residue at position 340 is alanine (A340). In some embodiments, the amino acid residue at A340 is replaced with serine (A340S).

In some embodiments, a recombinant cellobiohydrolase variant comprises at least about 70% (or at least about 75%, at least about 80%, at least about 85%, at least about 90%, at least about 95%, at least about 96%, at least about 97%, at least about 98%, or at least about 99%) sequence identity to SEQ ID NO:1 and comprises an amino acid substitution, relative to SEQ ID NO:1, at one or more positions selected from 15, 204, and 340, wherein the position is numbered with reference to SEQ ID NO:1. In some embodiments, the substituted amino acid residue at position 15 is phenylalanine, isoleucine, or serine (X15F/I/S); the substituted amino acid residue at position 204 is tryptophan (X204W); and/or the substituted amino acid residue at position 340 is serine (X340S). In some embodiments, the starting amino acid residue at position 15 is alanine, the starting amino acid at position 204 is alanine, and/or the starting amino acid at position 340 is alanine. In some embodiments, the amino acid residue at A15 is replaced with phenylalanine, isoleucine, or serine (A15F/I/S); the amino acid residue at position A204 is replaced with tryptophan (A204W); and/or the amino acid residue at position A340 is replaced with serine (A340S).

In some embodiments, the variant further comprises an amino acid substitution, relative to SEQ ID NO:1, at one or more positions selected from 39, 113, and 250. In some embodiments, the substituted amino acid residue at position 39 is alanine or cysteine (X39A/C); the substituted amino acid residue at position 113 is leucine or arginine (X113L/R); and/or the substituted amino acid residue at position 250 is proline or valine (X250P/V). In some embodiments, the starting amino acid residue at position 39 is asparagine, the starting amino acid at position 113 is asparagine, and/or the starting amino acid at position 250 is serine. In some embodiments, the amino acid residue at N39 is replaced with alanine or cysteine (N39A/C); the amino acid residue at position N113 is replaced with leucine or arginine (N113L/R); and/or the amino acid residue at position S250 is replaced with proline or valine (S250P/V).

In some embodiments, a recombinant cellobiohydrolase variant comprises at least about 70% (or at least about 75%, at least about 80%, at least about 85%, at least about 90%, at least about 95%, at least about 96%, at least about 97%, at least about 98%, or at least about 99%) sequence identity to SEQ ID NO:1 and has one or more amino acid substitution sets selected from the amino acid substitution sets listed in Table 3 or Table 4.

In some embodiments, a recombinant cellobiohydrolase variant comprises at least about 70% (or at least about 75%, at least about 80%, at least about 85%, at least about 90%, at least about 95%, at least about 96%, at least about 97%, at least about 98%, or at least about 99%) sequence identity to SEQ ID NO:1, comprises one or more amino acid substitution sets selected from the amino acid substitution sets listed in Table 3 or Table 4, and further comprises at least one, two, three, four, five, six, seven, eight, nine, ten, eleven or twelve additional substitutions, e.g., 1-5, 2-6, 4-8, or 5-12 substitutions (which optionally are conservative substitutions). In some embodiments, the variant has 100% identity to SEQ ID NO:1 except for (1) the substitutions present in any individual cellobiohydrolase variant selected from variant numbers 1-55 in Tables 3 and 4 and (2) one, two, three, four, five, six, seven, eight, nine, ten, eleven or twelve additional substitutions, e.g., 1-5, 2-6, 4-8, or 5-12 substitutions (which optionally are conservative substitutions).

In some embodiments, a recombinant cellobiohydrolase variant is a biologically active fragment of a full-length cellobiohydrolase variant polypeptide.

In some embodiments, a recombinant cellobiohydrolase variant comprises at least about 50% (or at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:1 and comprises one or more amino acid substitutions selected from:

- a cysteine or asparagine residue at position 31 (X31C/N);
- an alanine, cysteine, lysine, proline, arginine, or valine residue at position 39 (X39A/C/K/P/R/V);
- a cysteine, glycine, leucine, or methionine residue at position 160 (X160C/G/L/M);
- a cysteine, methionine, serine, or threonine residue at position 199 (X199C/M/S/T);
- a glutamine, arginine, or tryptophan residue at position 204 (X204Q/R/W);
- a cysteine, histidine, lysine, asparagine, proline, threonine, or valine residue at position 250 (X250C/H/K/N/P/T/V);
- an alanine, aspartic acid, or lysine residue at position 273 (X273A/D/K);
- a methionine or threonine residue at position 297 (X297M/T);
- a glutamic acid, proline, or tryptophan residue at position 345 (X345E/P/W); and
- a glutamic acid, lysine, or glutamine residue at position 361 (X361E/K/Q), wherein the position is numbered with reference to SEQ ID NO:1, and wherein the cellobiohydrolase variant has increased thermostability in comparison to wild-type C1 CBH2a (SEQ ID NO:1).

In some embodiments, the variant is derived from a cellobiohydrolase polypeptide from a fungal strain. In some embodiments, the variant comprises at least 90% sequence identity to a CBH2 from C1 (SEQ ID NOs:1 or 20), *Chaetomium globosum* (SEQ ID NO:10), *Neurospora crassa*(SEQ ID NO:11), *Sordaria macrospora*(SEQ ID NO:12), *Podospora anserina* (SEQ ID NO:13), *Magnaporthe oryzae* (SEQ ID NO:14), *Leptosphaeria maculans* (SEQ ID NO:15), *Phaeosphaeria nodorum* (SEQ ID NO:16), *Schizophyllum commune* (SEQ ID NO:17), *Pyrenophora teres* f. *teres* (SEQ ID NO:18), or *Pyrenophora tritici-repentis* (SEQ ID NO:19).

In some embodiments, the variant exhibits at least a 1.1-fold increase in thermostability relative to wild-type C1 CBH2a (SEQ ID NO:1). In some embodiments, the variant exhibits at least a 1.5-fold increase in thermostability relative to wild-type C1 CBH2a (SEQ ID NO:1). In some embodiments, the variant has increased thermostability after incubation at pH 5.0 and 55° C. for 1 hour in comparison to wild-type C1 CBH2a (SEQ ID NO:1).

In another aspect, the present invention provides polynucleotides encoding cellobiohydrolase variants that exhibit improved properties. In some embodiments, the polynucleotide encodes an amino acid sequence that comprises at least about 70% (or at least about 75%, at least about 80%, at least about 85%, at least about 90%, at least about 95%, at least about 96%, at least about 97%, at least about 98%, or at least about 99%) sequence identity to SEQ ID NO:1 and comprises an amino acid substitution at one or more positions selected from 11, 13, 14, 15, 31, 39, 55, 69, 75, 81, 95, 109, 110, 113, 122, 159, 160, 199, 200, 204, 211, 230, 250, 265, 266, 272, 273, 297, 329, 340, 345, 346, and 361, wherein the position is numbered with reference to SEQ ID NO:1. In some embodiments, the polynucleotide encodes an amino acid sequence that comprises at least about 70% (or at least about 75%, at least about 80%, at least about 85%, at least about 90%, at least about 95%, at least about 96%, at least about 97%, at least about 98%, or at least about 99%) sequence identity to SEQ ID NO:1 and comprises an amino acid substitution at one or more positions selected from R11, A13, S14, A15, Q31, N39, S55, T69, T75, R81, V95, A109, K110, N113, D122, N159, S160, W199, L200, A204, Q211, S230, S250, N265, T266, K272, S273, G297, G329, A340, S345, F346, and T361, wherein the position is numbered with reference to SEQ ID NO:1. In some embodiments, the polynucleotide encodes an amino acid sequence that comprises one or more amino acid substitutions selected from R11I/N/T/V, A13P, 514L, A15F/I/S, Q31C, N39A/C/K/P/R/V, S55P, T69C, T75S, R81K, V95L, A109F/M, K110E/Q, N113L/R/T, D122S, N159H, S160C/L/M, W199M/T, L200P, A204Q/W, Q211K, S230A, S250C/P/V, N265H, T266L, K272A, S273A/D, G297M, G329P, A340S, S345E/P, F346A/K/N/S/Y, and T361E/K/Q. In some embodiments, the polynucleotide hybridizes at high stringency to the complement of SEQ ID NO:2 and comprises one or more amino acid substitutions as described herein.

In still another aspect, the present invention provides expression vectors comprising a polynucleotide encoding a cellobiohydrolase variant as described herein.

In yet another aspect, the present invention provides host cells transformed with a polynucleotide or vector encoding a cellobiohydrolase variant as described herein. In some embodiments, the host cell expresses a non-naturally occurring cellobiohydrolase having the amino acid sequence of a cellobiohydrolase variant as described herein. In some embodiments, the host cell is a yeast or filamentous fungus.

In still another aspect, the present invention provides enzyme compositions comprising a recombinant cellobiohydrolase variant as described herein. In some embodiments, the enzyme composition is used in a composition for a saccharification application. In some embodiments, the enzyme composition comprising a cellobiohydrolase variant of the present invention will comprise other enzymes (e.g., one or more other cellulases).

In yet another aspect, the present invention provides methods of producing a cellobiohydrolase variant comprising culturing a host cell transformed with a polynucleotide or vector encoding a cellobiohydrolase variant as described herein under conditions sufficient for the production of the cellobiohydrolase variant by the cell. In some embodiments, the cellobiohydrolase variant polypeptide is secreted by the cell and obtained from the cell culture medium.

In still another aspect, the present invention provides methods of producing a fermentable sugar, comprising contacting a cellulosic biomass with a β-glucosidase (Bgl), a type 2 endoglucanase (EG2), a type 1a cellobiohydrolase (CBH1a), a glycoside hydrolase 61 protein (GH61), and a CBH2a variant as described herein under conditions in which the fermentable sugar is produced.

In yet another aspect, the present invention provides methods of producing an end-product from a cellulosic substrate, comprising (a) contacting the cellulosic substrate with a β-glucosidase (Bgl), a type 2 endoglucanase (EG2), a type 1a cellobiohydrolase (CBH1a), a glycoside hydrolase 61 protein (GH61), and a CBH2a variant as described herein under conditions in which fermentable sugars are produced; and (b) contacting the fermentable sugars with a microorganism in a fermentation to produce the end-product. In some embodiments, prior to step (a), the cellulosic substrate is pretreated to increase its susceptibility to hydrolysis. In some embodiments, the end-product is an alcohol, an amino acid, an organic acid, a diol, or glycerol. In some embodiments, the end-product is an alcohol (e.g., ethanol or butanol). In some embodiments, the microorganism is a yeast. In some embodiments, the process comprises a simultaneous saccharification and fermentation process. In some embodiments, the saccharification and fermentation steps are consecutive. In some embodiments, the enzyme production is simultaneous with saccharification and fermentation.

BRIEF DESCRIPTION OF THE DRAWINGS

FIGS. 1A-1D. Amino acid sequence alignment. The amino acid sequence of *M. thermophila* CBH2a without signal peptide (SEQ ID NO:1) ("CBH2a") was aligned with 11 other proteins without signal peptides: *Chaetomium globosum* CBS 148.51 unnamed protein (SEQ ID NO:10) ("XP_001226566.1"), *Sordaria macrospora* unnamed protein (SEQ ID NO:12) ("CBI58887.1"), *Neurospora crassa* OR74A (SEQ ID NO:11) ("XP_956581.1"), *Podospora anserine* S mat+ unnamed protein (SEQ ID NO:13) ("XP_001903893.1"), *M. thermophila* cellobiohydrolase type 2b (SEQ ID NO:20) ("CBH2b"), *Leptosphaeria maculans* unnamed protein (SEQ ID NO:15) ("CBY00792.1"), *Phaeosphaeria nodorum* SN15 unnamed protein (SEQ ID NO:16) ("XP_001806560.1"), *Pyrenophora tritici-repentis* Pt-1C-BFP exoglucanase 3 precursor (SEQ ID NO:19) ("XP_001931623.1"), *Pyrenophora teres* f. *teres* 0-1 unnamed protein (SEQ ID NO:18) ("XP_003300842.1"), *Schizophyllum commune* H4-8 glycoside hydrolase family 6 protein (SEQ ID NO:17) ("XP_003028483.1"), or *Magnaporthe oryzae* 70-15 unnamed protein (SEQ ID NO:14) ("XP_362054.1"). The consensus sequence of the aligned proteins is provided as SEQ ID NO:25.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in analytical chemistry, cell culture, molecular genetics, organic chemistry and nucleic acid chemistry and hybridization described below are those well known and commonly employed in the art. As used herein, "a," "an," and "the" include plural references unless the context clearly dictates otherwise.

The terms "biomass," "biomass substrate," "cellulosic biomass," "cellulosic feedstock," and "cellulosic substrate" refer to materials that contain cellulose. Biomass can be derived from plants, animals, or microorganisms, and may include agricultural, industrial, and forestry residues, industrial and municipal wastes, and terrestrial and aquatic crops grown for energy purposes. Examples of cellulosic substrate include, but are not limited to, wood, wood pulp, paper pulp, corn fiber, corn grain, corn cobs, crop residues such as corn husks, corn stover, grasses, wheat, wheat straw, barley, barley straw, hay, rice, rice straw, switchgrass, waste paper, paper and pulp processing waste, woody or herbaceous plants, fruit or vegetable pulp, distillers grain, rice hulls, cotton, hemp, flax, sisal, sugar cane bagasse, sugar beets, sorghum, soy, components obtained from milling of grains, trees, branches, roots, leaves, wood chips, sawdust, shrubs and bushes, vegetables, fruits, and flowers and mixtures thereof. In some embodiments, the biomass or cellulosic substrate comprises, but is not limited to, cultivated crops (e.g., grasses, including C4 grasses, such as switchgrass, cord grass, rye grass, miscanthus, reed canary grass, or any combination thereof), sugar processing residues, for example, but not limited to, bagasse (e.g., sugar cane bagasse, beet pulp [e.g., sugar beet], or a combination thereof), agricultural residues (e.g., soybean stover, corn stover, corn fiber, rice straw, sugar cane straw, rice, rice hulls, barley straw, corn cobs, wheat straw, canola straw, oat straw, oat hulls, hemp, flax, sisal, cotton, or any combination thereof), fruit pulp, vegetable pulp, distillers' grains, and/or forestry biomass (e.g., wood, wood pulp, paper pulp, recycled wood pulp fiber, sawdust, hardwood, such as aspen wood, softwood, or a commination thereof). Furthermore, in some embodiments, the biomass or cellulosic substrate comprises cellulosic waste material and/or forestry waste materials, including but not limited to, paper and pulp processing waste, municipal paper waste, newsprint, cardboard, and the like. In some embodiments, biomass comprises one species of fiber, while in some alternative embodiments, the biomass or cellulosic substrate comprises a mixture of fibers that originate from different biomasses. In some embodiments, the biomass may also comprise transgenic plants that express ligninase and/or cellulase enzymes, see, e.g., US 2008/0104724. In some embodiments, the biomass substrate is "pretreated," or treated using methods known in the art, such as chemical pretreatment (e.g., ammonia pretreatment, dilute acid pretreatment, dilute alkali pretreatment, or solvent exposure), physical pretreatment (e.g., steam explosion or irradiation), mechanical pretreatment (e.g., grinding or milling) and biological pretreatment (e.g., application of lignin-solubilizing microorganisms) and combinations thereof, to increase the susceptibility of cellulose to hydrolysis.

"Saccharification" refers to the process in which substrates (e.g., cellulosic biomass) are broken down via the action of cellulases to produce fermentable sugars (e.g. monosaccharides such as but not limited to glucose).

"Fermentable sugars" refers to simple sugars (monosaccharides, disaccharides and short oligosaccharides) such as but not limited to glucose, xylose, galactose, arabinose, mannose and sucrose. Fermentable sugar is any sugar that a microorganism can utilize or ferment.

The term "fermentation" is used broadly to refer to the cultivation of a microorganism or a culture of microorganisms that use simple sugars, such as fermentable sugars, as an energy source to obtain a desired product.

As used herein, the term "cellulase" refers to a category of enzymes capable of hydrolyzing cellulose (β-1,4-glucan or β-D-glucosidic linkages) to shorter cellulose chains, oligosaccharides, cellobiose and/or glucose.

As used herein, the term "cellobiohydrolase" or "CBH" refers to a category of cellulases (EC 3.2.1.91) that hydrolyze glycosidic bonds in cellulose. In some embodiments, the cellobiohydrolase is a "type 2 cellobiohydrolase," a cellobiohydrolase belonging to the glycoside hydrolase family 6 (GH6) family of cellulases and which is also commonly called "the Cel6 family." Cellobiohydrolases of the GH6 family are described, for example, in the Carbohydrate Active Enzymes (CAZY) database, accessible at www.cazy.org/GH6.html.

As used herein, the term "endoglucanase" or "EG" refers to a category of cellulases (EC 3.2.1.4) that catalyze the hydrolysis of internal β-1,4 glucosidic bonds of cellulose.

As used herein, the term "β-glucosidase," "cellobiase," or "BGL" refers to a category of cellulases (EC 3.2.1.21) that catalyze the hydrolysis of cellobiose to glucose.

As used herein, the term "glycoside hydrolase 61" or "GH61" refers to a category of cellulases that enhance cellulose hydrolysis when used in conjunction with one or more additional cellulases. The GH61 family of cellulases is described, for example, in the Carbohydrate Active Enzymes (CAZY) database, accessible at www.cazy.org/GH61.html, and in Harris et al., 2010, *Biochemistry* 49(15):3305-16.

As used herein, the term "C1" refers to *Myceliophthora thermophila*, including a fungal strain described by Garg, A., 1966, "An addition to the genus *Chrysosporium corda*" *Mycopathologia* 30: 3-4. "*Chrysosporium lucknowense*" includes the strains described in U.S. Pat. Nos. 6,015,707, 5,811,381 and 6,573,086; US Pat. Pub. Nos. 2007/0238155, US 2008/0194005, US 2009/0099079; International Pat. Pub. Nos. WO 2008/073914 and WO 98/15633, all incorporated herein by reference, and include, without limitation, *Chrysosporium lucknowense* Garg 27K, VKM-F 3500 D (Accession No. VKM F-3500-D), C1 strain UV13-6 (Accession No. VKM F-3632 D), C1 strain NG7C-19 (Accession No. VKM F-3633 D), and C1 strain UV18-25 (VKM F-3631 D), all of which have been deposited at the All-Russian Collection of Microorganisms of Russian Academy of Sciences (VKM), Bakhurhina St. 8, Moscow, Russia, 113184, and any derivatives thereof. Although initially described as *Chrysosporium lucknowense*, C1 may currently be considered a strain of *Myceliophthora thermophila*. Other C1 strains include cells deposited under accession numbers ATCC 44006 and PTA-12255, CBS (Centraalbureau voor Schimmelcultures) 122188, CBS 251.72, CBS 143.77, CBS 272.77, CBS122190, CBS122189, and VKM F-3500D. Exemplary C1 derivatives include modified organisms in which one or more endogenous genes or sequences have been deleted or modified and/or one or more heterologous genes or sequences have been introduced. Derivatives include UV18#100f ΔalpI, UV18#100f Δpyr5 Δalp1, UV18#100.f Δalp1 Δpep4 Δalp2, UV18#100.f Δpyr5 Δalp1 Δpep4 Δalp2 and UV18#100.f Δpyr4 Δpyr5 Δalp1 Δpep4 Δalp2, as described in WO 2008/073914 and WO 2010/107303, each of which is incorporated herein by reference.

As used herein, the term "wild-type *M. thermophila* cellobiohydrolase type 2a" or "wild-type *M. thermophila* CBH2a" refers to SEQ ID NO:1. SEQ ID NO:1 is the mature peptide sequence (i.e., lacking a signal peptide) of CBH2a that is expressed by the naturally occurring fungal strain *M. thermophila.*

As used herein, the term "variant" refers to a cellobiohydrolase polypeptide or polynucleotide encoding a cellobiohydrolase polypeptide comprising one or more modifications relative to wild-type *M. thermophila* CBH2a or the wild-type polynucleotide encoding *M. thermophila* CBH2a (such as substitutions, insertions, deletions, and/or truncations of one or more amino acid residues or of one or more specific nucleotides or codons in the polypeptide or polynucleotide, respectively), and biologically active fragments thereof. In some embodiments, the variant is a "*M. thermophila* variant" derived from a *M. thermophila* CBH2a polypeptide and comprising one or more modifications relative to wild-type *M. thermophila* CBH2a or the wild-type polynucleotide encoding wild-type *M. thermophila* CBH2a, or a biologically active fragment thereof.

As used herein, the term "cellobiohydrolase polypeptide" refers to a polypeptide having cellobiohydrolase activity.

As used herein, the term "cellobiohydrolase polynucleotide" refers to a polynucleotide encoding a polypeptide having cellobiohydrolase activity.

As used herein, the term "cellobiohydrolase activity" refers to the enzymatic activity of a cellobiohydrolase, e.g., hydrolyzing a cellulose-containing substrate.

The terms "improved" or "improved properties," as used in the context of describing the properties of a cellobiohydrolase variant, refers to a cellobiohydrolase variant polypeptide that exhibits an improvement in a property or properties as compared to the wild-type *M. thermophila* CBH2a (SEQ ID NO:1) or a specified reference polypeptide. Improved properties may include increased protein expression, increased thermoactivity, increased thermostability, increased pH activity, increased stability (e.g., increased pH stability), increased product specificity, increased specific activity, increased substrate specificity, increased resistance to substrate or end-product inhibition, increased chemical stability, reduced inhibition by glucose, increased resistance to inhibitors (e.g., acetic acid, lectins, tannic acids, and phenolic compounds), and altered pH/temperature profile.

As used herein, the phrase "improved thermoactivity" or "increased thermoactivity" refers to a variant enzyme displaying an increase, relative to a reference enzyme (e.g., a wild-type cellobiohydrolase), in the amount of cellobiohydrolase enzymatic activity (e.g., substrate hydrolysis) in a specified time under specified reaction conditions, for example, elevated temperature. Exemplary methods for measuring cellobiohydrolase activity are provided in the Examples and include, but are not limited to, measuring cellobiose production from crystalline cellulose as measured by colorimetric assay or HPLC. To compare cellobiohydrolase activity of two recombinantly expressed proteins, the specific activity (activity per mole enzyme or activity per gram enzyme) can be compared. Alternatively, cells expressing and secreting the recombinant proteins can be cultured under the same conditions and the cellobiohydrolase activity per volume culture medium can be compared.

As used herein, the term "improved thermostability" or "increased thermostability" refers to a variant enzyme displaying an increase in "residual activity" relative to a reference enzyme (e.g., a wild-type cellobiohydrolase or a second variant enzyme). Residual activity is determined by (1) exposing the variant enzyme or reference enzyme to stress conditions of elevated temperature, optionally at lowered pH, for a period of time and then determining cellobiohydrolase activity; (2) exposing the variant enzyme or reference enzyme to unstressed conditions for the same period of time and then determining cellobiohydrolase activity; and (3) calculating residual activity as the ratio of activity obtained under stress conditions (1) over the activity obtained under unstressed conditions (2). For example, the cellobiohydrolase activity of the enzyme exposed to stress conditions ("a") is compared to that of a control in which the enzyme is not exposed to the stress conditions ("b"), and residual activity is equal to the ratio a/b. A variant with increased thermostability will have greater residual activity than the wild-type enzyme. In one embodiment the enzymes are exposed to stress conditions of 55° C. at pH 5.0 for 1 hr, but other cultivation conditions, such as conditions described herein, can be used. Exemplary methods for measuring residual cellobiohydrolase activity are provided in the Examples and include, but are not limited to, measuring cellobiose production from crystalline cellulose as measured by colorimetric assay or HPLC.

As used herein, the term "improved stability" or "increased stability" refers to a variant enzyme that retains substantially all of its residual activity under stressed conditions relative to its activity under unstressed conditions. In some embodiments, a stressed condition is elevated temperature, lowered temperature, elevated pH, lowered pH, elevated salt concentration, lowered salt concentration, or increased concentration of an enzyme inhibitor (e.g., acetic acid, lectins, tannic acids, and phenolic compounds). Residual activity is determined by (1) exposing the variant enzyme to stress conditions, such as elevated temperature or lowered pH, for a period of time and then determining cellobiohydrolase activity; (2) exposing the variant enzyme to unstressed conditions for the same period of time and then determining cellobiohydrolase activity; and (3) calculating residual activity as the ratio of activity obtained under stress conditions (1) over the activity obtained under unstressed conditions (2). A variant with increased stability will have greater residual activity than a reference enzyme exposed to the same stressed conditions (e.g., a wild-type cellobiohydrolase). In one embodiment the enzymes are exposed to stress conditions of 55° C. at pH 5.0 for 1 hr, but other cultivation conditions, such as conditions described herein, can be used.

As used herein, the term "reference enzyme" refers to an enzyme to which a variant enzyme of the present invention is compared in order to determine the presence of an improved property in the variant enzyme being evaluated, including but not limited to improved thermoactivity, improved thermostability, or improved stability. In some embodiments, a reference enzyme is a wild-type enzyme (e.g., wild-type *M. thermophila* CBH2a). In some embodiments, a reference enzyme is another variant enzyme (e.g., another variant enzyme of the present invention).

The term "biologically active fragment," as used herein, refers to a polypeptide that has an amino-terminal and/or carboxy-terminal deletion and/or internal deletion, but where the remaining amino acid sequence is identical to the corresponding positions in the sequence to which it is being compared (e.g., a full-length cellobiohydrolase variant of the invention) and that retains substantially all of the activity of the full-length polypeptide. A biologically active fragment can comprise about 60%, about 65%, about 70%, about 75%, about 80%, about 85%, at about 90%, about 91%, about 92%, about 93%, about 94%, about 95%, about 96%, about 97%, about 98%, or about 99% of a full-length cellobiohydolrase polypeptide.

As used herein, "polynucleotide" refers to a polymer of deoxyribonucleotides or ribonucleotides in either single- or double-stranded form, and complements thereof.

Nucleic acids "hybridize" when they associate, typically in solution. Nucleic acids hybridize due to a variety of well-characterized physico-chemical forces, such as hydrogen bonding, solvent exclusion, base stacking and the like. As used herein, the term "stringent hybridization wash conditions" in the context of nucleic acid hybridization experiments, such as Southern and Northern hybridizations, are sequence dependent, and are different under different environmental parameters. An extensive guide to the hybridization of nucleic acids is found in Tijssen, 1993, "Laboratory Techniques in Biochemistry and Molecular Biology-Hybridization with Nucleic Acid Probes," Part I, Chapter 2 (Elsevier, New York), which is incorporated herein by reference. For polynucleotides of at least 100 nucleotides in length, low to very high stringency conditions are defined as follows: prehybridization and hybridization at 42° C. in 5×SSPE, 0.3% SDS, 200 μg/ml sheared and denatured salmon sperm DNA, and either 25% formamide for low stringencies, 35% formamide for medium and medium-high stringencies, or 50% formamide for high and very high stringencies, following standard Southern blotting procedures. For polynucleotides of at least 100 nucleotides in length, the carrier material is finally washed three times each for 15 minutes using 2×SSC, 0.2% SDS 50° C. (low stringency), at 55° C. (medium stringency), at 60° C. (medium-high stringency), at 65° C. (high stringency), or at 70° C. (very high stringency).

The terms "peptide," "polypeptide," and "protein" are used interchangeably herein to refer to a polymer of amino acid residues.

The term "amino acid" refers to naturally occurring and synthetic amino acids, as well as amino acid analogs. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

A "conservative substitution" as used with respect to amino acids, refers to the substitution of an amino acid with a chemically similar amino acid. Amino acid substitutions which often preserve the structural and/or functional properties of the polypeptide in which the substitution is made are known in the art and are described, for example, by H. Neurath and R. L. Hill, 1979, in "The Proteins," Academic Press, New York. The most commonly occurring exchanges are isoleucine/valine, tyrosine/phenylalanine, aspartic acid/glutamic acid, lysine/arginine, methionine/leucine, aspartic acid/asparagine, glutamic acid/glutamine, leucine/isoleucine, methionine/isoleucine, threonine/serine, tryptophan/phenylalanine, tyrosine/histidine, tyrosine/tryptophan, glutamine/arginine, histidine/asparagine, histidine/glutamine, lysine/asparagine, lysine/glutamine, lysine/glutamic acid, phenylalanine/leucine, phenylalanine/methionine, serine/alanine, serine/asparagine, valine/leucine, and valine/methionine. In some embodiments, there may be at least 1, at least 2, at least 3, at least 4, at least 5, at least 6, at least 7, at least 8, at least 9, at least 10, at least 15, at least 20, at least 25, at least 30, at least 35, or at least 40 conservative substitutions.

The following nomenclature may be used to describe substitutions in a reference sequence relative to a reference sequence or a variant polypeptide or nucleic acid sequence: "R-#-V," where # refers to the position in the reference sequence, R refers to the amino acid (or base) at that position in the reference sequence, and V refers to the amino acid (or base) at that position in the variant sequence. In some embodiments, an amino acid (or base) may be called "X," by which is meant any amino acid (or base). As a non-limiting example, for a variant polypeptide described with reference to a wild-type CBH2a polypeptide (e.g., SEQ ID NO:1), "S250P" indicates that in the variant polypeptide, the serine at position 250 of the reference sequence is replaced by proline, with amino acid position being determined by optimal alignment of the variant sequence with SEQ ID NO:1. Similarly, "S250P/V" describes two variants: a variant in which the serine at position 250 of the reference sequence is replaced by proline and a variant in which the serine at position 250 of the reference sequence is replaced by valine.

The term "amino acid substitution set" or "substitution set" refers to a group of amino acid substitutions. A substitution set can have 1, 2, 3, 4, 5, 6, 7, 8, 9, 10, 11, 12, 13, 14, 15, or more amino acid substitutions. In some embodiments, a substitution set refers to the set of amino acid substitutions that is present in any of the variant cellobiohydrolases listed in Table 3 or Table 4. For example, the substitution set for Variant 43 (Table 4) consists of the amino acid substitutions A15I, N39C, N113R, A204W, S250V, S273D, and A340S.

The term "isolated" refers to a nucleic acid, polynucleotide, polypeptide, protein, or other component that is partially or completely separated from components with which it is normally associated (other proteins, nucleic acids, cells, etc.). In some embodiments, an isolated polypeptide or protein is a recombinant polypeptide or protein.

A nucleic acid (such as a polynucleotide), a polypeptide, or a cell is "recombinant" when it is artificial or engineered, or derived from or contains an artificial or engineered protein or nucleic acid. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Identity" or "percent identity," in the context of two or more polypeptide sequences, refers to two or more sequences or subsequences that are the same or have a specified percentage of amino acid residues that are the same (e.g., share at least about 70%, at least about 75%, at least about 80%, at least about 85%, at least about 88% identity, at least about 89%, at least about 90%, at least about 91%, at least about 92%, at least about 93%, at least about 94%, at least about 95%, at least about 96%, at least about 97%, at least about 98%, or at least about 99% identity) over a specified region to a reference sequence, when compared and aligned for maximum correspondence over a comparison window, or designated region as measured using a sequence comparison algorithms or by manual alignment and visual inspection.

A "comparison window," as used herein, includes reference to a segment of any one of a number of contiguous positions from about 20 to about 500, e.g., about 50 to about 300 contiguous positions, about 50 to 250 contiguous positions, or also about 100 to about 200 contiguous positions, in which a sequence may be compared to a reference sequence of the same number of contiguous positions after the two sequences are optimally aligned. As noted, in some embodiments the comparison is between the entire length of the two sequences, or, if one sequence is a fragment of the other, the entire length of the shorter of the two sequences.

Optimal alignment of sequences for comparison and determination of sequence identity can be determined by a sequence comparison algorithm or by visual inspection (see, generally, Ausubel et al., infra). When optimally aligning sequences and determining sequence identity by visual inspection, percent sequence identity is calculated as the number of residues of the test sequence that are identical to the reference sequence divided by the number of non-gap positions and multiplied by 100. When using a sequence comparison algorithm, test and reference sequences are entered into a computer, subsequence coordinates and sequence algorithm program parameters are designated. The sequence comparison algorithm then calculates the percent sequence identities for the test sequences relative to the reference sequence, based on the program parameters.

An algorithm that may be used to determine whether a variant cellobiohydrolase has sequence identity to SEQ ID NO:1 is the BLAST algorithm, which is described in Altschul et al., 1990, *J. Mol. Biol.* 215:403-410, which is incorporated herein by reference. Software for performing BLAST analyses is publicly available through the National Center for Biotechnology Information (on the worldwide web at ncbi.nlm-.nih.gov/). The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. For amino acid sequences, the BLASTP program uses as defaults a word size (W) of 3, an expectation (E) of 10, and the BLOSUM62 scoring matrix (see Henikoff & Henikoff, 1989, *Proc. Natl. Acad. Sci. USA* 89:10915). Other programs that may be used include the Needleman-Wunsch procedure, J. Mol. Biol. 48: 443-453 (1970), using blosum62, a Gap start penalty of 7 and gap extend penalty of 1; and gapped BLAST 2.0 (see Altschul, et al. 1997, Nucleic Acids Res., 25:3389-3402) both available to the public at the National Center for Biotechnology Information Website.

Multiple sequences can be aligned with each other by visual inspection or using a sequence comparison algorithm, such as PSI-BLAST (Altschul, et al., 1997, supra) or "T-Coffee" (Notredame et al., 2000, J. Mol. Bio. 302:205-17). T-Coffee alignments may be carried out using default parameters (T-Coffee Technical Documentation, Version 8.01, July 2009, WorldWideWeb.tcoffee.org), or AlignX® (AlignX Jul. 31, 2006, a component of Vector NTI advance 10.3.0 and based on the ClustalW algorithm). For multiple sequence alignment, the following default AlignX multiple alignment parameters are used: DNA/Protein Gap Open Penalty: 15/10; DNA/Protein Gap Extension Penalty: 6.66/0.05; Gap separation penalty range: 8; Use end gap separation penalty; % identity for alignment delay: 40; Use residue-specific gaps; Use hydrophilic residue gap; transition weighing (for DNA only). After aligning multiple sequences, percent sequence identity can be calculated as the percentage of identical residues among all ungapped positions between the pairs.

The phrase "substantial sequence identity" or "substantial identity," in the context of two nucleic acid or polypeptide sequences, refers to a sequence that has at least 70% identity to a reference sequence. Percent identity can be any integer from 70% to 100%. Two nucleic acid or polypeptide sequences that have 100% sequence identity are said to be "identical." A nucleic acid or polypeptide sequence are said to have "substantial sequence identity" to a reference sequence when the sequences have at least about 70%, at least about 75%, at least 80%, at least 85%, at least 90%, at least 91%, at least 92%, at least 93%, at least 94%, at least 95%, at least 96%, at least 97%, at least 98%, or at least 99% or greater sequence identity as determined using the methods described herein, such as BLAST using standard parameters as described above. For an alignment that extends along the entire length of SEQ ID NO:1, there may be at least 265, at least 284, at least 303, at least 322, at least 341, at least 344, at least 348, at least 352, at least 356, at least 360, at least 363, at least 367, at least 371, or at least 375 amino acids identical between a variant sequence and SEQ ID NO:1.

The term "pre-protein" refers to a protein including an amino-terminal signal peptide (or leader sequence) region attached. The signal peptide is cleaved from the pre-protein by a signal peptidase prior to secretion to result in the "mature" or "secreted" protein.

A "vector" is a DNA construct for introducing a DNA sequence into a cell. A vector may be an expression vector that is operably linked to a suitable control sequence capable of effecting the expression in a suitable host of the polypeptide encoded in the DNA sequence. An "expression vector" has a promoter sequence operably linked to the DNA sequence (e.g., transgene) to drive expression in a host cell, and in some embodiments a transcription terminator sequence.

The term "expression" includes any step involved in the production of the polypeptide including, but not limited to, transcription, post-transcriptional modification, translation, post-translational modification, and secretion.

The term "operably linked" refers to a configuration in which a control sequence is appropriately placed at a position relative to the coding sequence of the DNA sequence such that the control sequence influences the expression of a polypeptide.

An amino acid or nucleotide sequence (e.g., a promoter sequence, signal peptide, terminator sequence, etc.) is "heterologous" to another sequence with which it is operably linked if the two sequences are not associated in nature.

The terms "transform" or "transformation," as used in reference to a cell, means a cell has a non-native nucleic acid sequence integrated into its genome or as an episome (e.g., plasmid) that is maintained through multiple generations.

The term "culturing" refers to growing a population of microbial cells under suitable conditions in a liquid or solid medium.

The term "introduced," as used in the context of inserting a nucleic acid sequence into a cell, means conjugated, transfected, transduced or transformed (collectively "transformed") or otherwise incorporated into the genome of, or maintained as an episome in, the cell.

DETAILED DESCRIPTION OF THE INVENTION

I. Introduction

Fungi, bacteria, and other organisms produce a variety of cellulases and other enzymes that act in concert to catalyze decrystallization and hydrolysis of cellulose to yield fermentable sugars. One such fungus is *M. thermophila*, which is described by Garg, 1966, "An addition to the genus *Chrysosporium corda*" *Mycopathologia* 30: 3-4; see also U.S. Pat. Nos. 6,015,707 and 6,573,086, which are incorporated herein by reference for all purposes.

One *M. thermophila* cellulase of interest is the cellobiohydrolase referred to as "*M. thermophila* cellobiohydrolase type 2a" or "CBH2a". The cellobiohydrolase variants described herein are particularly useful for the production of fermentable sugars from cellulosic biomass. In one aspect, the present invention relates to cellobiohydrolase variants that have improved properties, relative to wild-type *M. thermophila* cellobiohydrolase (SEQ ID NO:1), under process conditions used for saccharification of biomass. Improved properties, described hereinabove, include properties include increased thermostability and/or increased thermoactivity and/or increased pH tolerance. In another aspect, the present invention relates to methods of generating fermentable sugars from cellulosic biomass, by contacting the biomass with a cellulase composition comprising a cellobiohydrolase variant as described herein under conditions suitable for the production of fermentable sugars. Increased thermostability, especially at extreme pH, can be useful for improving yields in saccharification, improving rates of saccharification, and broadening the substrate range of a cellulase composition.

Various aspects of the invention are described in the following sections.

II. Cellobiohydrolase Type 2 Variants

Properties of Cellobiohydrolase Variants

In one aspect, the present invention provides CBH2a variants, and biologically active fragments thereof, having improved properties over a wild-type cellobiohydrolase. In some embodiments, the CBH2a variants exhibit increased thermostability in comparison to a wild-type CBH2a (e.g., a *M. thermophila* CBH2a having the amino acid sequence of SEQ ID NO:1) under conditions relevant to commercial cellulose hydrolysis processes.

In some embodiments, the present invention provides a recombinant *M. thermophila* CBH2a variant comprising at least about 70% (or at least about 75%, at least about 80%, at least about 85%, at least about 90%, at least about 95%, at least about 96%, at least about 97%, at least about 98%, or at least about 99%) sequence identity to SEQ ID NO:1 and comprising an amino acid substitution, relative to SEQ ID NO:1, at one or more positions selected from R11, A13, S14, A15, Q31, N39, S55, T69, T75, R81, V95, A109, K110, N113, D122, N159, S160, W199, L200, A204, Q211, S230, S250, N265, T266, K272, S273, G297, G329, A340, S345, F346, and T361, wherein the position is numbered with reference to SEQ ID NO:1, and wherein the variant has increased thermostability in comparison to wild-type *M. thermophila* CBH2a (SEQ ID NO:1). In some embodiments, a CBH2a variant has an amino acid sequence that is encoded by a nucleic acid that hybridizes under high stringency conditions to the complement of SEQ ID NO:2 (e.g., over substantially the entire length of a nucleic acid exactly complementary to SEQ ID NO:2) and comprises an amino acid substitution at one or more positions selected from R11, A13, S14, A15, Q31, N39, S55, T69, T75, R81, V95, A109, K110, N113, D122, N159, S160, W199, L200, A204, Q211, S230, S250, N265, T266, K272, S273, G297, G329, A340, S345, F346, and T361, wherein the position is numbered with reference to SEQ ID NO:1.

In some embodiments, the invention provides a recombinant *M. thermophila* CBH2a variant comprising at least about 70% (or at least about 75%, at least about 80%, at least about 85%, at least about 90%, at least about 95%, at least about 96%, at least about 97%, at least about 98%, or at least about 99%) sequence identity to SEQ ID NO:1 and comprising one or more amino acid substitutions selected from R11I/N/T/V, A13P, 514L, A15F/I/S, Q31C, N39A/C/K/P/R/V, S55P, T69C, T75S, R81K, V95L, A109F/M, K110E/Q, N113L/R/T, D122S, N159H, S160C/L/M, W199M/T, L200P, A204Q/W, Q211K, S230A, S250P/V, N265H, T266L, K272A, S273A/D, G297M, G329P, A340S, S345E/P, F346A/K/N/S/Y, and T361E/K/Q, wherein the position is numbered with reference to SEQ ID NO:1, and wherein the variant has increased thermostability in comparison to wild-type *M. thermophila* CBH2a (SEQ ID NO:1). In some embodiments, a CBH2a variant has an amino acid sequence that is encoded by a nucleic acid that hybridizes under high stringency conditions to the complement of SEQ ID NO:2 (e.g., over substantially the entire length of a nucleic acid exactly complementary to SEQ ID NO:2) and comprises one or more amino acid substitutions selected from R11I/N/T/V, A13P, 514L, A15F/I/S, Q31C, N39A/C/K/P/R/V, S55P, T69C, T75S, R81K, V95L, A109F/M, K110E/Q, N113L/R/T, D122S, N159H, S160C/L/M, W199M/T, L200P, A204Q/W, Q211K, S230A, S250P/V, N265H, T266L, K272A, S273A/D, G297M, G329P, A340S, S345E/P, F346A/K/N/S/Y, and T361E/K/Q, wherein the position is numbered with reference to SEQ ID NO:1.

In some embodiments, the *M. thermophila* CBH2a variant exhibits at least about a 1.1 fold, at least about a 1.2 fold, at least about a 1.3 fold, at least about a 1.4 fold, at least about a 1.5 fold, at least about a 1.6 fold, at least about a 1.7 fold, at least about a 1.8 fold, at least about a 1.9 fold, at least about a 2.0 fold increase or more in thermostability relative to wild-type *M. thermophila* CBH2a (SEQ ID NO:1). Exemplary variants are identified in Table 3 or Table 4, wherein fold improvement in thermostability is measured as described in the Examples (i.e., expressed in *S. cerevisiae*).

In some embodiments, the *M. thermophila* CBH2a variant of the present invention comprises at least about 1, at least about 2, at least about 3, at least about 4, at least about 5, at least about 6, at least about 7, at least about 8, at least about 9, or at least about 10 or more amino acid residues which have been substituted (e.g., with substitutions described herein) as compared to the amino acid sequence of the wild-type cellobiohydrolase protein from which the cellobiohydrolase variant is derived. In some embodiments, the *M. thermophila* CBH2a variant differs from the CBH2a of SEQ ID NO:1 at no more than 20, no more than 19, no more than 18, no more than 17, no more than 16, no more than 15, no more than 14, no more than 13, no more than 12, no more than 11, no more than 10, no more than 9, no more than 8, no more than 7, no more than 6, or no more than 5 residues.

In some embodiments, a *M. thermophila* CBH2a variant of the present invention comprises at least about 70% (or at least about 75%, at least about 80%, at least about 85%, at least about 90%, at least about 95%, at least about 96%, at least about 97%, at least about 98%, or at least about 99%) sequence identity to SEQ ID NO:1 and comprises one or more amino acid substitution sets selected from the substitution sets identified in Table 3. In some embodiments, a CBH2a variant comprises at least about 70% (or at least about 75%, at least about 80%, at least about 85%, at least about 90%, at least about 95%, at least about 96%, at least about 97%, at least about 98%, or at least about 99%) sequence identity to SEQ ID NO:1 and comprises one or more amino acid substitution sets selected from the substitution sets of any of Variants 1, 2, 3, 4, 5, 6, 7, 8, 9, 10, 11, 12, 13, 14, 16, 17, 18, 19, 20, 21, 22, or 23 as identified in Table 3.

In some embodiments, a CBH2a variant of the present invention comprises at least about 70% (or at least about 75%, at least about 80%, at least about 85%, at least about 90%, at least about 95%, at least about 96%, at least about 97%, or at least about 98%) sequence identity to SEQ ID NO:1 and comprises one or more amino acid substitution sets selected from the substitution sets identified in Table 4. In some embodiments, a CBH2a variant comprises at least about 70% (or at least about 75%, at least about 80%, at least about 85%, at least about 90%, at least about 95%, at least about 96%, at least about 97%, at least about 98%, or at least about 99%) sequence identity to SEQ ID NO:1 and comprises one or more amino acid substitution sets selected from the substitution sets of any of Variants 44, 45, 46, or 47 as identified in Table 4.

In some embodiments, exemplary variants include any of the cellobiohydrolase proteins in Tables 3 or 4, as well as any variants that comprise one or more amino acid substitutions or substitution sets provided in Table 3 or Table 4 and comprise at least about 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:1. In some embodiments, exemplary variants include any variants comprising one or more amino acid substitutions or substitution sets provided in Table 3 or Table 4 and comprising at least about 70% (or at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:1, and further comprising one, two, three, four, five, six, or more additional amino acid substitutions.

Certain cellobiohydrolase variants comprise an amino acid substitution, relative to SEQ ID NO:1, at one or more positions selected from V95 and S230. In some embodiments, a *M. thermophila* cellobiohydrolase variant comprises one or more amino acid substitutions selected from V95L and S230A. In some embodiments, a *M. thermophila* cellobiohydrolase variant comprises the amino acid substitutions of variant 1, i.e., the amino acid substitutions V95L and S230A. In some embodiments, the *M. thermophila* cellobiohydrolase variant has the amino acid sequence of SEQ ID NO:3.

Certain cellobiohydrolase variants comprise an amino acid substitution, relative to SEQ ID NO:1, at position F346. In some embodiments, a *M. thermophila* cellobiohydrolase variant comprises the amino acid substitutions of variant 2, i.e., the amino acid substitution F346Y. In some embodiments, the *M. thermophila* cellobiohydrolase variant has the amino acid sequence of SEQ ID NO:4.

Certain cellobiohydrolase variants comprise an amino acid substitution, relative to SEQ ID NO:1, at position S250. In some embodiments, a *M. thermophila* cellobiohydrolase variant comprises the amino acid substitutions of variant 22, i.e., the amino acid substitution S250P. In some embodiments, the *M. thermophila* cellobiohydrolase variant has the amino acid sequence of SEQ ID NO:5.

Certain cellobiohydrolase variants comprise an amino acid substitution, relative to SEQ ID NO:1, at one or more positions selected from A15, N39, N113, A204, S250, S273, and A340. In some embodiments, the variant comprises one or more amino acid substitutions selected from A15I, N39C, N113R, A204W, S250V, S273D, and A340S. In some embodiments, a *M. thermophila* cellobiohydrolase variant comprises the amino acid substitutions of variant 44, i.e., the amino acid substitutions A15I, N39C, N113R, A204W, S250V, S273D, and A340S. In some embodiments, the *M. thermophila* cellobiohydrolase variant has the amino acid sequence of SEQ ID NO:6.

Certain cellobiohydrolase variants comprise an amino acid substitution, relative to SEQ ID NO:1, at one or more positions selected from A15, N39, K110, A204, S250, and A340. In some embodiments, the variant comprises one or more amino acid substitutions selected from A15S, N39A, K110Q, A204W, S250P, and A340S. In some embodiments, a *M. thermophila* cellobiohydrolase variant comprises the amino acid substitutions of variant 45, i.e., the amino acid substitutions A15S, N39A, K110Q, A204W, S250P, and A340S. In some embodiments, the *M. thermophila* cellobiohydrolase variant has the amino acid sequence of SEQ ID NO:7.

Certain cellobiohydrolase variants comprise an amino acid substitution, relative to SEQ ID NO:1, at one or more positions selected from A15, N39, N113, A204, T266, and S345. In some embodiments, the variant comprises one or more amino acid substitutions selected from A15I, N39A, N113L, A204W, T266L, and S345E. In some embodiments, a *M. thermophila* cellobiohydrolase variant comprises the amino acid substitutions of variant 46, i.e., the amino acid substitutions A15I, N39A, N113L, A204W, T266L, and S345E. In some embodiments, the *M. thermophila* cellobiohydrolase variant has the amino acid sequence of SEQ ID NO:8.

Certain cellobiohydrolase variants comprise an amino acid substitution, relative to SEQ ID NO:1, at one or more positions selected from A15, S55, A204, Q211, N265, and A340. In some embodiments, the variant comprises one or more amino acid substitutions selected from A15I, S55P, A204W, Q211K, N265H, and A340S. In some embodiments, a *M. thermophila* cellobiohydrolase variant comprises the amino acid substitutions of variant 47, i.e., the amino acid substitutions A15I, S55P, A204W, Q211K, N265H, and A340S. In some embodiments, the *M. thermophila* cellobiohydrolase variant has the amino acid sequence of SEQ ID NO:9.

Certain *M. thermophila* cellobiohydrolase variants comprise an amino acid substitution, relative to SEQ ID NO:1, at one or more positions selected from A15, A204, S250, and A340. In some embodiments, a cellobiohydrolase variant of the invention comprises one or more amino acid substitutions selected from A15F/I/S, A204Q/W, S250P/V, and A340S. In some embodiments, a cellobiohydrolase variant of the invention comprises the amino acid substitutions A15F/I/S, A204Q/W, S250P/V, and A340S. In some embodiments, a cellobiohydrolase variant of the invention further comprises an amino acid substitution, relative to SEQ ID NO:1, at one or more positions selected from S14, N39, S55, T69, T75, R81, K110, N113, N159, Q211, N265, T266, K272, S273, and S345. In some embodiments, a cellobiohydrolase variant of the invention comprises one or more amino acid substitutions selected from 514L, N39A/C/K, S55P, T69C, T75S, R81K, K110E/Q, N113L/R/T, N159H, Q211K, N265H, T266L, K272A, S273D, and S345E/P. In some embodiments, a cellobiohydrolase of the invention comprises the amino acid substitutions 514L, N39A/C/K, S55P, T69C, T75S, R81K, K110E/Q, N113L/R/T, N159H, Q211K, N265H, T266L, K272A, S273D, and S345E/P.

It will be appreciated that secreted cellobiohydrolase variants of the present invention may encompass additional amino acid substitutions beyond those listed above (such as additional conservative substitutions) may be less-than-full length compared to a wild-type secreted *M. thermophila* cellobiohydrolase protein and may contain additional residues at the amino and/or carboxy termini. Thus, cellobiohydrolase variants of the present invention may comprise insertions or deletions (e.g., truncation at the amino- and/or carboxy-termini) relative to a full-length cellobiohydrolase (e.g., SEQ ID NO:1). For illustration and not limitation, in some embodiments the variant may be longer or shorter by up to about 25%, about 20%, about 15%, about 10%, about 5%, about 4%, about 3%, about 2%, or about 1% of the wild-type length. For example, a cellobiohydrolase variant with an amino-terminal and/or carboxy-terminal deletion and/or internal deletion relative to a full-length cellobiohydrolase (e.g., SEQ ID NO:1) may comprise, for example, about 70%, about 75%, about 80%, about 85%, about 90%, about 91%, about 92%, about 93%, about 94%, about 95%, about 96%, about 97%, about 98%, or about 99% the length of the full-length cellobiohydrolase polypeptide.

In some embodiments, a cellobiohydrolase variant of the present invention comprises a signal peptide sequence at the amino-terminus of the polypeptide. In some embodiments, the signal peptide is an endogenous *M. thermophila* cellobiohydrolase signal peptide. In some embodiments, the signal peptide is a signal peptide from another *M. thermophila* secreted protein. In some embodiments, the signal peptide is a signal peptide from a cellobiohydrolase or another secreted protein secreted from an organism other than *M. thermophila* (e.g., from a filamentous fungus, yeast, or bacteria). In some embodiments the signal peptide is artificial.

Biologically Active Fragments

Skilled artisans will appreciate that oftentimes, the full length sequence of an enzyme is not required for enzymatic activity. Therefore, “biologically active fragments” of the various CBH2a variant polypeptides described herein are also contemplated and included in the disclosure. The enzymatic activity of biologically active fragments may be measured as described in the Examples hereinbelow.

In some embodiments the biologically active fragments comprise at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% of the corresponding full-length cellobiohydrolase variant. In some embodiments, the biologically active fragments, like the full-length cellobiohydrolase variants from which they are derived, will exhibit improved properties, relative to wild-type *M. thermophila* cellobiohydrolase (SEQ ID NO:1), such as increased thermostability and/or increased thermoactivity and/or increased pH tolerance.

In some embodiments, regions of one or both termini, such as, for example, from about 1 to about 10, about 1 to about 15, or about 1 to about 20 residues at one or both termini, may be removed without significantly deleteriously affecting the activity of the enzyme. Such deletions can oftentimes be made internally without detrimental effect. In instances of multifunctional, multi-domain enzymes, entire domains can be removed without deleteriously affecting a desired enzymatic activity.

III. Substitutions in Homologous Cellobiohydrolases

In another aspect, the invention contemplates that substitutions may be introduced into type 2 cellobiohydrolases of fungal species other than *M. thermophila*, at positions corresponding to the amino acid positions of wild-type *M. thermophila* CBH2a (SEQ ID NO:1), to produce variants, or biologically active fragments thereof, having improved properties, such as improved thermostability, relative to the cellobiohydrolase from which the variant is derived (e.g., wild-type CBH2 or a CBH2a of a fungal species other than *M. thermophila*).

CBH2 belongs to the glycoside hydrolase family 6 (GH6) family of cellulases (formerly known as cellulase family B), a group of enzymes that hydrolyze glycosidic bonds in cellulose. GH6 cellulase cellobiohydrolase type 2 have a catalytic domain that hydrolyzes cellulose, and may also have a cellulose-binding domain (CBD). For example, *Myceliophthora thermophila* CBH2b has a CBD. FIG. 1 shows that there is a high degree of conservation of primary amino acid sequence structure among many cellobiohydrolase type 2 homologs. Alignments across 12 cellobiohydrolase type 2 homologs of fungal origin shows that these homologs exhibit about 50% sequence homology or greater to *M. thermophila* CBH2a (SEQ ID NO:1) across the length of the entire mature protein.

A number of fungal strains (including, but not limited to, *Chaetomium, Leptosphaeria, Magnaporthe, Neurospora, Podospora, Pyrenophora, Schizophyllum*, and *Sordaria*) express cellobiohydrolase homologs with significant sequence identity to *M. thermophila* cellobiohydrolase. It is within the ability of one of ordinary skill in the art to identify other examples of structurally homologous proteins. The present invention provides variants of these and other homologous cellobiohydrolase proteins in which substitutions are made at residues corresponding to those identified herein in the *M. thermophila* CBH2a protein.

In some embodiments, a recombinant cellobiohydrolase of the invention is derived from a fungal protein shown in Table 1.

TABLE 1

Cellobiohydrolase homologs having significant sequence identity to *M. thermophila* CBH2a

| Organism | Protein | SEQ ID NO | % Homology to *M. thermophila* CBH2a |
|---|---|---|---|
| *Myceliophthora thermophila* | Cellobiohydrolase type IIa (CBH2a) | 1 | — |
| *Chaetomium globosum* CBS 148.51 | Unnamed protein | 10 | 83% |
| *Neurospora crassa* OR74A | Exoglucanase 3 precursor | 11 | 82% |
| *Sordaria macrospora* | Unnamed protein | 12 | 81% |
| *Podospora anserina* S mat+ | Unnamed protein | 13 | 77% |
| *Magnaporthe oryzae* 70-15 | Unnamed protein | 14 | 77% |
| *Leptosphaeria maculans* | Unnamed protein | 15 | 72% |
| *Phaeosphaeria nodorum* SN15 | Unnamed protein | 16 | 71% |
| *Schizophyllum commune* H4-8 | Glycoside hydrolase family 6 protein | 17 | 70% |
| *Pyrenophora teres* f. *teres* 0-1 | Unnamed protein | 18 | 69% |
| *Pyrenophora tritici-repentis* Pt-1C-BFP | Exoglucanase 3 precursor | 19 | 68% |
| *Myceliophthora thermophila* | Cellobiohydrolase type IIb (CBH2b) | 20 | 51% |

It is possible to use sequence alignment or other methods to identify amino acid positions in structurally related proteins (i.e., homologs) that correspond to each other. Corresponding positions in homologs are considered Performance Sensitive Positions (PSPs) when a substitution in that position is determined to affect a property in a set of multiple homologs. Substitutions at PSPs in other homologs are expected to also have significant effects on activity. For example, the amino acid sequence of cellobiohydrolase homolog *M. thermophila* CBH2b was aligned to *M. thermophila* CBH2a. For those amino acid positions in *M. thermophila* CBH2a at which substitution mutations were shown experimentally to exhibit increased thermostability as compared to wild-type CBH2a (identified in Tables 3 and 4, infra), the corresponding amino acid position was identified in the *M. thermophila* CBH2b by alignment. These identified amino acid sequences were compared to experimental data generated from screening variants of wild-type *M. thermophila* CBH2b for increased thermostability to identify those residues of CBH2b in which experimentally identified beneficial substitutions were found. Experimental data for the *M. thermophila* CBH2a corresponding residues is shown in Example 6. Residues for which improved CBH2 performance is found for *M. thermophila* CBH2a as well as *M. thermophila* CBH2b are identified as "performance sensitive positions," positions where amino acid substitutions are likely to have a beneficial effect on CBH2 performance.

As shown in Table 2, PSPs were identified for some variants of CBH2a and CBH2b. In some embodiments, an amino acid position where a substitution has been shown to be beneficial for increasing cellobiohydrolase thermostability and/or thermoactivity in *M. thermophila* cellobiohydrolases is predicted to be a position at which substitution will increase cellobiohydrolase thermostability and/or thermoactivity in a homolog of *M. thermophila* cellobiohydrolase. In some embodiments, the amino acid position at which a substitution is beneficial for increasing cellobiohydrolase thermostability and/or thermoactivity is an amino acid position selected from position 31, position 39, position 160, position 199, position 204, position 250, position 273, position 297, position 345, and position 361, wherein the amino acid positions are numbered with reference to SEQ ID NO:1. In some embodiments, an amino acid substitution at position 31 is selected from cysteine and asparagine (X31C/N). In some embodiments, an amino acid substitution at position 39 is selected from alanine, cysteine, lysine, proline, arginine, and valine (X39A/C/K/P/R/V). In some embodiments, an amino acid substitution at position 160 is selected from cysteine, glycine, leucine, and methionine (X160C/G/L/M). In some embodiments, an amino acid substitution at position 199 is selected from cysteine, methionine, serine, and threonine (X199C/M/S/T). In some embodiments, an amino acid substitution at position 204 is selected from glutamine, arginine, and tryptophan (X204Q/R/W). In some embodiments, an amino acid substitution at position 250 is selected from cysteine, histidine, lysine, asparagine, proline, threonine, and valine (X250C/H/K/N/P/T/V). In some embodiments, an amino acid substitution at position 273 is selected from alanine, aspartic acid, and lysine (X273A/D/K). In some embodiments, an amino acid substitution at position 297 is selected from methionine and threonine (X297M/T). In some embodiments, an amino acid substitution at position 345 is selected from glutamic acid, proline, and tryptophan (X345E/P/W). In some embodiments, an amino acid substitution at position 361 is selected from glutamic acid, lysine, and glutamine (X361E/K/Q).

TABLE 2

Performance Sensitive Positions Identified in CBH2 Based on Sequence Alignment

| Performance Sensitive Position (numbered according to *M. thermophila* CBH2a) | Beneficial Mutations in *M. thermophila* CBH2a (SEQ ID NO: 1) | Beneficial Mutations in *M. thermophila* CBH2b |
|---|---|---|
| 31 | Q31C | S111N |
| 39 | N39ACKPRV | D119PR |
| 160 | S160CLM | M250G |
| 199 | W199MT | W289CMS |
| 204 | A204QW | A294R |
| 250 | S250CPV | S336HKNPT |
| 273 | S273AD | S359DK |
| 297 | G297M | G384T |
| 345 | S345EP | Y432W |
| 361 | T361EKQ | Q448K |

Thus, in some embodiments, the present invention provides a recombinant cellobiohydrolase variant comprising at least about 50% (or at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%) sequence identity to SEQ ID NO:1 and comprising one or more amino acid substitutions selected from:

- a cysteine or asparagine residue at position 31 (X31C/N);
- an alanine, cysteine, lysine, proline, arginine, or valine residue at position 39 (X39A/C/K/P/R/V);
- a cysteine, glycine, leucine, or methionine residue at position 160 (X160C/G/L/M);
- a cysteine, methionine, serine, or threonine residue at position 199 (X199C/M/S/T);

- a glutamine, arginine, or tryptophan residue at position 204 (X204Q/R/W);
- a cysteine, histidine, lysine, asparagine, proline, threonine, or valine at position 250 (X250C/H/K/N/P/T/V);
- an alanine, aspartic acid, or lysine residue at position 273 (X273A/D/K);
- a methionine or threonine residue at position 297 (X297M/T);
- a glutamic acid, proline, or tryptophan residue at position 345 (X345E/P/W); and
- a glutamic acid, lysine, or glutamine residue at position 361 (X361E/K/Q), wherein the position is numbered with reference to the amino acid sequence of SEQ ID NO:1.

In some embodiments, the cellobiohydrolase variant of the present invention is derived from a cellobiohydrolase polypeptide from a fungal strain. In some embodiments, the cellobiohydrolase variant comprises at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to a cellobiohydrolase from *M. thermophila* (SEQ ID NO:1 or SEQ ID NO:20), *Chaetomium globosum* (SEQ ID NO:10), *Neurospora crassa* (SEQ ID NO:11), *Sordaria macrospora* (SEQ ID NO:12), *Podospora anserina* (SEQ ID NO:13), *Magnaporthe oryzae* (SEQ ID NO:14), *Leptosphaeria maculans* (SEQ ID NO:15), *Phaeosphaeria nodorum* (SEQ ID NO:16), *Schizophyllum commune* (SEQ ID NO:17), *Pyrenophora teres* f. *teres* (SEQ ID NO:18), or *Pyrenophora tritici-repentis* (SEQ ID NO:19). In some embodiments, the cellobiohydrolase variant has at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to a cellobiohydrolase sequence described herein and comprises an amino acid substitution at one or more positions homologous to the positions identified in Table 2 (i.e., position 31, position 39, position 160, position 199, position 204, position 250, position 273, position 297, position 345, and position 361, as numbered with reference to SEQ ID NO:1).

In some embodiments, the variant has increased thermostability in comparison to wild-type *M. thermophila* CBH2a (SEQ ID NO:1). In some embodiments, the variant has increased thermostability in comparison to the cellobiohydrolase polypeptide (e.g., a cellobiohydrolase polypeptide from a fungal strain, e.g., a cellobiohydrolase polypeptide from *Acremonium, Agaricus, Aspergillus, Botryotinia, Chaetomium, Chrysosporium, Cochliobolus, Coniophora, Coprinopsis, Fusarium, Gibberella, Humicola, Hypocrea, Leptosphaeria, Lentinus, Magnaporthe, Moniliophthora, Nectria, Neurospora, Penicillium, Phaetosphaeria, Phanerochaete, Podospora, Pyrenophora, Sordaria, Talaromyces, Thielavia, Trametes, Trichoderma, Verticillium*, or *Volvariella*) from which the variant is derived.

In another aspect, the present invention relates to a method of making CBH2a variants having improved thermostability. In some embodiments, the method comprises: (a) identifying a sequence that comprises at least about 50% (or at least about 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%) sequence identity to SEQ ID NO:1; (b) aligning the identified sequence with the sequence of SEQ ID NO:1; and (c) substituting one or more amino acid residues of the identified sequence, wherein the substitutions are made at one or more positions selected from R11, A13, S14, A15, Q31, N39, S55, T69, T75, R81, V95, A109, K110, N113, D122, N159, S160, W199, L200, A204, Q211, S230, S250, N265, T266, K272, S273, G297, G329, A340, S345, F346, and T361.

In some embodiments, step (c) of the method comprises making one or more amino acid substitutions selected from R11I/N/T/V, A13P, 514L, A15F/I/S, Q31C, N39A/C/K/P/R/V, S55P, T69C, T75S, R81K, V95L, A109F/M, K110E/Q, N113L/R/T, D122S, N159H, S160C/L/M, W199M/T, L200P, A204Q/W, Q211K, S230A, S250P/V, N265H, T266L, K272A, S273A/D, G297M, G329P, A340S, S345E/P, F346A/K/N/S/Y, and T361E/K/Q.

In some embodiments, the method further comprises determining whether the one or more amino acid substitutions increase the thermostability of the cellobiohydrolase variant in comparison to secreted wild-type *M. thermophila* CBH2a (SEQ ID NO:1).

IV. Making Cellobiohydrolase Variants

A cellobiohydrolase variant polypeptide of the invention can be subject to further modification to produce new polypeptides that retain the specific substitutions that characterize the variant and which may have desirable properties. For example, a polynucleotide encoding a cellobiohydrolase with an improved property can be subjected to additional rounds of mutagenesis to generate polypeptides with further improvements in the desired enzyme or enzyme properties.

Given the wild-type *M. thermophila* CBH2a sequence or the sequence of a wild-type fungal homolog of *M. thermophila* CBH2a, cellobiohydrolase variants can be generated according to the methods described herein and can be screened for the presence of improved properties, such as increased thermostability. Libraries of cellobiohydrolase variant polypeptides (and/or polynucleotides encoding the variant) may be generated from a parental sequence (e.g., wild-type *M. thermophila* CBH2a, or a wild-type cellobiohydrolase from another fungal strain such as a cellobiohydrolase of Table 1, or one of the cellobiohydrolase variants exemplified herein), and screened using a high throughput screen to determine improved properties such as increased stability at desired conditions, as described herein. Mutagenesis and directed evolution methods are well known in the art and can be readily applied to polynucleotides encoding cellobiohydrolase variants exemplified herein to generate variant libraries that can be expressed, screened, and assayed using the methods described herein. See, e.g., Ling, et al., 1999, "Approaches to DNA mutagenesis: an overview," *Anal. Biochem.,* 254(2):157-78; Dale, et al., 1996, "Oligonucleotide-directed random mutagenesis using the phosphorothioate method," *Methods Mol. Biol.,* 57:369-74; Smith, 1985, "In vitro mutagenesis," *Ann. Rev. Genet.,* 19:423-462; Botstein, et al., 1985, "Strategies and applications of in vitro mutagenesis," *Science,* 229:1193-1201; Carter, 1986, "Site-directed mutagenesis," *Biochem. J.,* 237:1-7; Kramer, et al., 1984, "Point Mismatch Repair," *Cell,* 38:879-887; Wells, et al., 1985, "Cassette mutagenesis: an efficient method for generation of multiple mutations at defined sites," *Gene,* 34:315-323; Minshull, et al., 1999, "Protein evolution by molecular breeding," *Current Opinion in Chemical Biology,* 3:284-290; Christians, et al., 1999, "Directed evolution of thymidine kinase for AZT phosphorylation using DNA family shuffling, " *Nature Biotechnology,* 17:259-264; Crameri, et al., 1998, "DNA shuffling of a family of genes from diverse species accelerates directed evolution," *Nature,* 391:288-291; Crameri, et al., 1997, "Molecular evolution of an arsenate detoxification pathway by DNA shuffling," *Nature Biotechnology,* 15:436-438; Zhang, et al., 1997 "Directed evolution of an effective fucosidase from a galactosidase by DNA shuffling and screening," *Proceedings of the National Academy of Sciences, U.S.A.,* 94:45-4-4509; Crameri, et al., 1996, "Improved green fluorescent protein by molecular evolution using DNA shuffling," *Nature Biotechnology,* 14:315-319; Stemmer, 1994, "Rapid evolution of a protein in vitro by DNA shuffling," *Nature,* 370:389-391; Stemmer, 1994, "DNA shuffling by random fragmentation and reassembly: In vitro recombination for molecular evolution," *Proceedings of the National Academy of Sciences, U.S.A.,* 91:10747-10751; WO 95/22625; WO 97/0078; WO 97/35966; WO 98/27230; WO 00/42651; and WO 01/75767, all of which are incorporated herein by reference.

Cellobiohydrolase variants having the amino acid substitutions described herein can be produced by recombinant expression or by chemical synthesis. Chemically synthesized polypeptides may be made using the well-known techniques of solid phase, liquid phase, or peptide condensation techniques, and can include any combination of amino acids as desired to produce the variants described herein. Synthetic amino acids can be obtained from Sigma, Cambridge Research Biochemical, or any other chemical company familiar to those skilled in the art.

V. Cellobiohydrolase Thermoactivity and Thermostability

Cellobiohydrolase activity and thermostability can be determined by methods described in the Examples section (e.g., Examples 3 and 4), and/or using other assay methods known in the art. For example, cellobiohydrolase activity may be determined using an assay that measures the conversion of crystalline cellulose to glucose.

Cellobiohydrolase activity can be determined, for example, using a cellulose assay, in which the ability of the cellobiohydrolase variants to hydrolyze a cellulose substrate to cellobiose, e.g., crystalline cellulose under specific temperature and/or pH conditions is measured, then a β-glucosidase is added to convert the cellobiose to glucose. For example, a supernatant containing the secreted cellobiohydrolase is mixed with a cellulose substrate, e.g., crystalline cellulose, in a buffered solution and β-glucosidase is added to convert the cellobiose to glucose. A biotransformation reaction is performed under specific time, temperature, and/or pH conditions, for example, pH 5.0, 50° C., for 16-24 hours. An aliquot of the biotransformation reaction is then assayed for conversion of cellulose (e.g., crystalline cellulose) to fermentable soluble sugars (e.g., glucose) Conversion of cellulose substrate (e.g., crystalline cellulose) to fermentable sugar oligomers (e.g., glucose) can be determined by art-known means, including but not limited to coupled enzymatic assay and colorimetric assay. For example, glucose concentrations can be determined using a coupled enzymatic assay based on glucose oxidase and horseradish peroxidase (e.g., GOPOD assay) as exemplified in Trinder, P. (1969) *Ann. Clin. Biochem.* 6:24-27, which is incorporated herein by reference in its entirety. GOPOD assay kits are known in the art and are readily commercially available, e.g., from Megazyme (Wicklow, Ireland). Methods for performing GOPOD assays are known in the art; see, e.g., McCleary et al., *J. AOAC Int.* 85(5):1103-11 (2002), the contents of which are incorporated by reference herein. Additional methods of cellobiose quantification include chromatographic methods, for example by HPLC as exemplified in the incorporated materials of U.S. Pat. Nos. 6,090,595 and 7,419,809.

In one exemplary assay, biotransformation reactions are performed by mixing 100 μl clear supernatant containing the secreted cellobiohydrolase variant with 300 μl of a slurry of crystalline cellulose in 200 mM sodium acetate buffer pH 5.0 (final concentration: 75 g/L crystalline cellulose; a glass bead/well) containing 0.15 g/L-β-glucosidase, which converts cellobiose to glucose. Biotransformation is performed at pH 5, 55-60° C. for an appropriate amount of time. The amount of glucose produced is then determined by art-known means, for example GOPOD assay. For the GOPOD assay, fermentable sugar oligomer (e.g., glucose) production is measured by mixing 10 μl of the above reaction with 190 μl of GOPOD assay mix. The reactions are allowed to shake for 45 min at room temperature. Absorbance of the solution is measured at 510 nm to determine the amount of glucose produced in the original biotransformation reaction, which is used to calculate cellobiohydrolase activity.

Cellobiohydrolase thermostability can be determined, for example, by exposing the cellobiohydrolase variants and the reference (e.g., wild-type) cellobiohydrolase to stress conditions of elevated temperature and/or low pH for a desired period of time and then determining residual cellobiohydrolase activity using an assay that measures the conversion of cellulose to glucose. For example, a supernatant containing the secreted cellobiohydrolase is exposed to stress conditions, for example, pH 4.5-5.0 and temperature 55-60° C. for 1 hour. After the challenge with stress conditions, residual cellobiohydrolase activity is measured by performing a biotransformation reaction on crystalline cellulose substrate such as Avicel in the presence of excess β-glucosidase at pH 5, 55° C. for 18 hours. The conversion of cellulose substrate (e.g., crystalline cellulose) to fermentable sugar oligomers (e.g., glucose) can be determined by art-known means, for example using any of the assays as described above, such as coupled enzymatic assay based on glucose oxidase and horseradish peroxidase or GOPOD assay.

In an exemplary assay, thermostability is screened using a cellulose-based High Throughput Assay. In deep, 96-well microtiter plates 100 μL of media supernatant containing cellobiohydrolase variant is added to 300 μL of 200 mM sodium acetate buffer pH 5.0 containing 0.15 g/L β-glucosidase and 75 gl/L crystalline cellulose. After sealing with aluminum/polypropylene laminate heat seal tape (Velocity 11 (Menlo Park, Calif.), Cat#06643-001)), the plates are shaken at 55° C. for 16-24 hours. The plates are centrifuged at 4000 rpm for 5 minutes. The glucose produced is then is measured by any art-known means, for example using any of the assays as described above, such as coupled enzymatic assay based on glucose oxidase and horseradish peroxidase or GOPOD assay.

Some cellobiohydrolase variants of the invention will have improved thermostability as compared to a reference sequence (e.g., a wild-type cellobiohydrolase or another cellobiohydrolase variant). In some embodiments, a cellobiohydrolase variant has improved thermostability at a pH range of 3.0 to 7.5, at a pH range of 3.5 to 6.5, at a pH range of 3.5 to 6.0, at a pH range of 3.5 to 5.5, at a pH range of 3.5 to 5.0, or at a pH range of 4.0 to 5.0. In some embodiments, a cellobiohydrolase variant has improved thermostability at a temperature of about 55° C. to 80° C., at a temperature of about 60° C. to 80° C., at a temperature of about 65° C. to 80° C., or at a temperature of about 65 to 75° C. In some embodiments, a cellobiohydrolase will have improved thermostability at a pH of 3.5 to 5.5 and a temperature of 55-70° C.

In some embodiments, the cellobiohydrolase variants of the invention exhibit cellobiohydrolase thermostability that is at least about 1.1 fold, at least about 1.5 fold, at least about 2.0 fold, or at least about 3.0 fold or greater than the cellobiohydrolase thermostability of a reference cellobiohydrolase (e.g., the wild-type cellobiohydrolase of SEQ ID NO:1) when tested under the same conditions. In some embodiments, the thermostability of the cellobiohydrolase variants at pH 4.5 and 70° C. is at least about 1.1 fold, at least about 1.5 fold, at least about 2.0 fold or greater than the thermostability of a control cellobiohydrolase (e.g., the wild-type cellobiohydrolase of SEQ ID NO:1) under the same conditions.

It will be apparent that the same assays may be used to assess cellobiohydrolase activity of biologically active fragments of cellobiohydrolase variants.

VI. Fusion Peptides and Additional Sequence Elements

In some embodiments, a cellobiohydrolase variant of the present invention further comprises additional sequences which do not alter the encoded activity of the cellobiohydrolase. For example, the cellobiohydrolase may be linked to an epitope tag or to another sequence useful in purification.

The present invention also provides cellobiohydrolase variant fusion polypeptides, wherein the fusion polypeptide comprises an amino acid sequence encoding a cellobiohydrolase variant polypeptide of the present invention or fragment thereof, linked either directly or indirectly through the N- or C-terminus of the cellobiohydrolase variant polypeptide to an amino acid sequence encoding at least a second (additional) polypeptide. The cellobiohydrolase variant fusion polypeptide may further include amino acid sequence encoding a third, fourth, fifth, or additional polypeptides. Typically, each additional polypeptide has a biological activity, or alternatively, is a portion of a polypeptide that has a biological activity, where the portion has the effect of improving expression and/or secretion and/or purification and/or detection of the fusion polypeptide from the desired expression host. These sequences may be fused, either directly or indirectly, to the N- or C-terminus of the cellobiohydrolase variant polypeptide or fragment thereof, or alternatively, to the N- or C-terminus of the additional polypeptides having biological activity.

In some embodiments, the additional polypeptide(s) encode an enzyme or active fragment thereof, and/or a polypeptide that improves expression and/or secretion of the fusion polypeptide from the desired expression host cell. For example, the additional polypeptide may encode a cellulase (for example, a cellobiohydrolase having a different amino acid sequence from the cellobiohydrolase variant polypeptide in the fusion polypeptide, or a polypeptide exhibiting endoglucanase activity or β-glucosidase activity) and/or a polypeptide that improves expression and secretion from the desired host cell, such as, for example, a polypeptide that is normally expressed and secreted from the desired expression host, such as a secreted polypeptide normally expressed from filamentous fungi. These include glucoamylase, α-amylase and aspartyl proteases from *Aspergillus niger, Aspergillus niger* var. *awamori*, and *Aspergillus oryzae*, cellobiohydrolase I, cellobiohydrolase II, endoglucanase I and endoglucase III from *Trichoderma* and glucoamylase from *Neurospora* and *Humicola* species. See WO 98/31821, which is incorporated herein by reference.

The polypeptide components of the fusion polypeptide may be linked to each other indirectly via a linker. Linkers suitable for use in the practice of the present invention are described in WO 2007/075899, which is incorporated herein by reference. Exemplary linkers include peptide linkers of from 1 to about 40 amino acid residues in length, including those from about 1 to about 20 amino acid residues in length, and those from about 1 to about 10 amino acid residues in length. In some embodiments, the linkers may be made up of a single amino acid residue, such as, for example, a Gly, Ser, Ala, or Thr residue or combinations thereof, particularly Gly and Ser. Linkers employed in the practice of the present invention may be cleavable. Suitable cleavable linkers may contain a cleavage site, such as a protease recognition site. Exemplary protease recognition sites are well known in the art and include, for example, Lys-Arg (the KEX2 protease recognition site, which can be cleaved by a native *Aspergillus* KEX2-like protease), Lys and Arg (the trypsin protease recognition sites). See, for example, WO 2007/075899.

Signal Peptides

In some embodiments, the cellobiohydrolase variant polypeptides of the present invention are secreted from the host cell in which they are expressed (e.g., a yeast or fungal cell) and are expressed as a pre-protein including a signal peptide, i.e., an amino acid sequence linked to the amino terminus of a polypeptide and which directs the encoded polypeptide into the cell secretory pathway. In one embodiment, the signal peptide is an endogenous *M. thermophila* cellobiohydrolase signal peptide. For example, the signal peptide of the CBH2a of SEQ ID NO:1 has the sequence MKFVQSATLAFAATALA (SEQ ID NO:26). In other embodiments, signal peptides from other *M. thermophila* secreted proteins are used.

Still other signal peptides may be used, depending on the host cell and other factors. Effective signal peptide coding regions for filamentous fungal host cells include, but are not limited to, the signal peptide coding regions obtained from *Aspergillus oryzae* TAKA amylase, *Aspergillus niger* neutral amylase, *Aspergillus niger* glucoamylase, *Rhizomucor miehei* asparatic proteinase, *Humicola insolens* cellulase, *Humicola lanuginosa* lipase, and *T. reesei* cellobiohydrolase II (TrCBH2).

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* β-lactamase, *Bacillus stearothermophilus* neutral proteases (nprT, nprS, nprM), and *Bacillus subtilis* prsA. Further signal peptides are described by Simonen and Palva, 1993, *Microbiol Rev* 57: 109-137 (incorporated herein by reference).

Useful signal peptides for yeast host cells also include those from the genes for *Saccharomyces cerevisiae* alpha-factor, *Saccharomyces cerevisiae* SUC2 invertase (see Taussig and Carlson, 1983, *Nucleic Acids Res* 11:1943-54; SwissProt Accession No. P00724), and others. See, e.g., Romanos et al., 1992, *Yeast* 8:423-488. Variants of these signal peptides and other signal peptides are suitable.

Cellulose Binding Domains

A cellulose binding domain (CBD) is a domain in cellulose degrading enzymes that binds specifically to cellulose. Although some naturally-occurring cellobiohydrolases have a CBD, others (such as wild-type *M. thermophila* CBH2a) do not. Thus, in some embodiments, a cellobiohydrolase variant of the present invention lacks a CBD. However, in some embodiments a CBD from a cellulose degrading enzyme (e.g., a cellobiohydrolase) can be joined to a cellobiohydrolase variant polypeptide as described herein that lacks a naturally-occurring CBD to make a fusion peptide having a CBD.

Thus, in some embodiments a cellobiohydrolase variant of the invention is a fusion peptide comprising a polypeptide having at least 70% amino acid sequence identity to SEQ ID NO:1 and having one or more substitutions or substitution sets as described herein (e.g., as listed in Table 3 or Table 4) and further comprising a cellulose binding domain (CBD). In some embodiments, the CBD is heterologous to the polypeptide having at least 70% amino acid sequence identity to SEQ ID NO:1 and having one or more substitutions or substitution sets as described herein. For example, in some embodiments a cellobiohydrolase variant of the present invention may comprise a polypeptide having at least 70% amino acid sequence identity to SEQ ID NO:1 and having one or more substitutions or substitution sets as described herein and fused to a CBD from another cellobiohydrolase protein, e.g., a CBD from *M. thermophila* CBH2b. In some embodiments, the CBD is joined to the polypeptide by a linker peptide.

In some embodiments, a cellobiohydrolase variant of the present invention has multiple CBDs. The multiple CBDs can be in tandem or in different regions of the polypeptide.

VII. Polynucleotides and Expression Systems Encoding Cellobiohydrolase Variants In another aspect, the invention provides polynucleotides encoding variant cellobiohydrolase polypeptides, or biologically active fragments thereof, as described herein. The polynucleotide may be operably linked to one or more heterologous regulatory or control sequences that control gene expression to create a recombinant polynucleotide capable of expressing the polypeptide. Expression constructs containing a heterologous polynucleotide encoding the engineered cellobiohydrolase can be introduced into appropriate host cells to express the cellobiohydrolase.

In some embodiments, the cellobiohydrolase variant is generated from a wild-type cellobiohydrolase cDNA sequence (e.g., a wild-type *M. thermophila* CBH2a cDNA sequence) or the portion thereof comprising the open reading frame, with changes made as required at the codons corresponding to substitutions described herein (e.g., at Tables 3 or 4). In addition, one or more "silent" nucleotide changes can be incorporated into the cDNA sequence. A DNA sequence may also be designed for high codon usage bias codons (codons that are used at higher frequency in the protein coding regions than other codons that code for the same amino acid). The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. In particular, a DNA sequence can be optimized for expression in a particular host organism. A variety of methods are known for determining the codon frequency and/or codon preference in specific organisms, including multivariate analysis, for example, using cluster analysis or correspondence analysis, and the effective number of codons used in a gene (see GCG CodonPreference, Genetics Computer Group Wisconsin Package; Codon W, John Peden, University of Nottingham; McInerney, J. O, 1998, *Bioinformatics* 14:372-73; Stenico et al., 1994, *Nucleic Acids Res.* 222437-46; Wright, F., 1990, *Gene* 87:23-29; Wada et al., 1992, *Nucleic Acids Res.* 20:2111-2118; Nakamura et al., 2000, *Nucl. Acids Res.* 28:292; Henaut and Danchin, "*Escherichia coli* and *Salmonella*," 1996, Neidhardt, et al. Eds., ASM Press, Washington D.C., p. 2047-2066, all of which are incorporated herein be reference). The data source for obtaining codon usage may rely on any available nucleotide sequence capable of coding for a protein, e.g., complete protein coding sequences (CDSs), expressed sequence tags (ESTs), or predicted coding regions of genomic sequences.

Those having ordinary skill in the art will understand that due to the degeneracy of the genetic code, a multitude of nucleotide sequences encoding cellobiohydrolase polypeptides of the present invention exist. For example, the codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide. It is understood that U in an RNA sequence corresponds to T in a DNA sequence. The invention contemplates and provides each and every possible variation of nucleic acid sequence encoding a polypeptide of the invention that could be made by selecting combinations based on possible codon choices.

Polynucleotides encoding cellobiohydrolases can be prepared using methods that are well known in the art. See, e.g., Carruthers, et al., 1982, *Cold Spring Harbor Symp. Quant. Biol.,* 47:411-18 and Adams et al., 1983, *J. Am. Chem. Soc.* 105:661, both of which are incorporated herein by reference. Typically, oligonucleotides of up to about 40 bases are individually synthesized, then joined (e.g., by enzymatic or chemical ligation methods, or polymerase-mediated methods) to form essentially any desired continuous sequence. For example, polynucleotides of the present invention can be prepared by chemical synthesis using, for example, the classical phosphoramidite method described by Beaucage, et al., 1981, *Tetrahedron Letters,* 22:1859-69, or the method described by Matthes, et al., 1984, *EMBO J.* 3:801-05, both of which are incorporated herein by reference. These methods are typically practiced in automated synthetic methods. According to the phosphoramidite method, oligonucleotides are synthesized, e.g., in an automatic DNA synthesizer, purified, annealed, ligated and cloned in appropriate vectors. Double stranded DNA fragments may then be obtained either by synthesizing the complementary strand and annealing the strands together under appropriate conditions, or by adding the complementary strand using DNA polymerase with an appropriate primer sequence.

General texts that describe molecular biological techniques which are useful herein, including the use of vectors, promoters, protocols sufficient to direct persons of skill through in vitro amplification methods, including the polymerase chain reaction (PCR) and the ligase chain reaction (LCR), and many other relevant methods, include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (2nd Ed.), Vol. 1-3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 2009) ("Ausubel"), all of which are incorporated herein by reference. Reference is made to Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36-47; *The Journal Of NIH Research* (1991) 3, 81-94; (Kwoh et al. (1989) *Proc. Natl. Acad. Sci.*

*USA* 86, 1173; Guatelli et al. (1990) *Proc. Natl. Acad. Sci. USA* 87, 1874; Lomeli et al. (1989) *J. Clin. Chem* 35, 1826; Landegren et al., (1988) *Science* 241, 1077-1080; Van Brunt (1990) *Biotechnology* 8, 291-294; Wu and Wallace, (1989) *Gene* 4, 560; Barringer et al. (1990) *Gene* 89, 117, and Sooknanan and Malek (1995) *Biotechnology* 13: 563-564, all of which are incorporated herein by reference. Methods for cloning in vitro amplified nucleic acids are described in Wallace et al., U.S. Pat. No. 5,426,039, which is incorporated herein by reference.

Vectors

The present invention makes use of recombinant constructs comprising a sequence encoding a cellobiohydrolase as described above. In a particular aspect the present invention provides an expression vector comprising a cellobiohydrolase polynucleotide operably linked to a heterologous promoter. Expression vectors of the present invention may be used to transform an appropriate host cell to permit the host to express the cellobiohydrolase protein. Methods for recombinant expression of proteins in fungi and other organisms are well known in the art, and a number expression vectors are available or can be constructed using routine methods. See, e.g., Tkacz and Lange, 2004, Advances in fungal biotechnology for industry, agriculture, and medicine, Kluwer Academic/Plenum Publishers, New York; Zhu et al., 2009, Construction of two Gateway vectors for gene expression in fungi, *Plasmid* 62:128-33; and Kavanagh, K. 2005, Fungi: biology and applications, Wiley, all of which are incorporated herein by reference.

Nucleic acid constructs of the present invention comprise a vector, such as, a plasmid, a cosmid, a phage, a virus, a bacterial artificial chromosome (BAC), a yeast artificial chromosome (YAC), and the like, into which a nucleic acid sequence of the invention has been inserted. Polynucleotides of the present invention can be incorporated into any one of a variety of expression vectors suitable for expressing a polypeptide. Suitable vectors include chromosomal, non-chromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated virus, retroviruses and many others. Any vector that transduces genetic material into a cell, and, if replication is desired, which is replicable and viable in the relevant host can be used.

In some embodiments, the construct further comprises regulatory sequences, including, for example, a promoter, operably linked to the protein encoding sequence. Large numbers of suitable vectors and promoters are known to those of skill in the art.

Promoters

In order to obtain high levels of expression in a particular host it is often useful to express the cellobiohydrolase variant of the present invention under the control of a heterologous promoter. A promoter sequence may be operably linked to the 5' region of the cellobiohydrolase coding sequence using routine methods.

Examples of useful promoters for expression of cellobiohydrolases include promoters from fungi. In some embodiments, a promoter sequence that drives expression of a gene other than a cellobiohydrolase gene in a fungal strain may be used. As a non-limiting example, a fungal promoter from a gene encoding an endoglucanase may be used. In some embodiments, a promoter sequence that drives the expression of a cellobiohydrolase gene in a fungal strain other than the fungal strain from which the cellobiohydrolase variant was derived may be used. As a non-limiting example, if the cellobiohydrolase variant is derived from C1, a promoter from a *T. reesei* cellobiohydrolase gene may be used or a promoter as described in WO 2010/107303, such as but not limited to the sequences identified as SEQ ID NO:25, SEQ ID NO:26, SEQ ID NO:27, SEQ ID NO:28, or SEQ ID NO:29 in WO 2010/107303.

Examples of other suitable promoters useful for directing the transcription of the nucleotide constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787, which is incorporated herein by reference), as well as the NA2-tpi promoter (a hybrid of the promoters from the genes for *Aspergillus niger* neutral alpha-amylase and *Aspergillus oryzae* triose phosphate isomerase), promoters such as cbh1, cbh2, egl1, egl2, pepA, hfb1, hfb2, xyn1, amy, and glaA (Nunberg et al., 1984, *Mol. Cell Biol.,* 4:2306-2315, Boel et al., 1984, *EMBO J.* 3:1581-85 and EPA 137280, all of which are incorporated herein by reference), and mutant, truncated, and hybrid promoters thereof. In a yeast host, useful promoters can be from the genes for *Saccharomyces cerevisiae* enolase (eno-1), *Saccharomyces cerevisiae* galactokinase (gall), *Saccharomyces cerevisiae* alcohol dehydrogenase/glyceraldehyde-3-phosphate dehydrogenase (ADH2/GAP), and *S. cerevisiae* 3-phosphoglycerate kinase. Other useful promoters for yeast host cells are described by Romanos et al., 1992, *Yeast* 8:423-488, incorporated herein by reference. Promoters associated with chitinase production in fungi may be used. See, e.g., Blaiseau and Lafay, 1992, *Gene* 120243-248 (filamentous fungus *Aphanocladium album*); Limon et al., 1995, *Curr. Genet,* 28:478-83 (*Trichoderma harzianum*), both of which are incorporated herein by reference.

In a yeast host, useful promoters can be from the genes for *Saccharomyces cerevisiae* enolase (ENO-1), *Saccharomyces cerevisiae* galactokinase (GALI), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8:423-88.

Other Expression Elements

Cloned cellobiohydrolases may also have a suitable transcription terminator sequence, a sequence recognized by a host cell to terminate transcription. The terminator sequence is operably linked to the 3' terminus of the nucleic acid sequence encoding the polypeptide. Any terminator that is functional in the host cell of choice may be used in the present invention.

For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease. Exemplary transcription terminators are described in U.S. Pat. No. 7,399,627, incorporated herein by reference.

Exemplary terminators for yeast host cells can be obtained from the genes for *Saccharomyces cerevisiae* enolase, *Saccharomyces cerevisiae* cytochrome C (CYCI), and *Saccharomyces cerevisiae* glyceraldehyde-3-phosphate dehydrogenase. Other useful terminators for yeast host cells are described by Romanos et al., 1992, *Yeast* 8:423-88.

A suitable leader sequence may be part of a cloned cellobiohydrolase sequence, which is a nontranslated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

Sequences may also contain a polyadenylation sequence, which is a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells can be from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are described by Guo and Sherman, *Mol Cell Biol* 5:5983-5990 (1995).

The expression vector of the present invention preferably contains one or more selectable markers, which permit easy selection of transformed cells. A selectable marker is a gene, the product of which provides for biocide or viral resistance, resistance to heavy metals, prototrophy to auxotrophs, and the like. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Embodiments for use in an *Aspergillus* cell include the amdS and pyrG genes of *Aspergillus nidulans* or *Aspergillus oryzae* and the bar gene of *Streptomyces hygroscopicus*. Suitable markers for yeast host cells are ADE2, HIS3, LEU2, LYS2, MET3, TRP1, and URA3.

VIII. Host Cells Comprising Cellobiohydrolase Variants

A vector comprising a sequence encoding a cellobiohydrolase is transformed into a host cell in order to allow propagation of the vector and expression of the cellobiohydrolase. In some embodiments, the cellobiohydrolase is post-translationally modified to remove the signal peptide and in some cases may be cleaved after secretion.

The transformed or transfected host cell described above is cultured in a suitable nutrient medium under conditions permitting the expression of the cellobiohydrolase. The medium used to culture the cells may be any conventional medium suitable for growing the host cells, such as minimal or complex media containing appropriate supplements. Cells are optionally grown in HTP media. Suitable media are available from commercial suppliers or may be prepared according to published recipes (e.g. in catalogues of the American Type Culture Collection).

Expression Hosts

In some embodiments, the host cell is a eukaryotic cell. Suitable eukaryotic host cells include, but are not limited to, fungal cells, algal cells, insect cells, and plant cells. Suitable fungal host cells include, but are not limited to, Ascomycota, Basidiomycota, Deuteromycota, Zygomycota, Fungi imperfecti. Particularly preferred fungal host cells are yeast cells and filamentous fungal cells. The filamentous fungal host cells of the present invention include all filamentous forms of the subdivision Eumycotina and Oomycota. (Hawksworth et al., In Ainsworth and Bisby's Dictionary of The Fungi, $8^{th}$ edition, 1995, CAB International, University Press, Cambridge, UK). Filamentous fungi are characterized by a vegetative mycelium with a cell wall composed of chitin, cellulose and other complex polysaccharides. The filamentous fungal host cells of the present invention are morphologically distinct from yeast.

In the present invention a filamentous fungal host cell may be a cell of a species of, but not limited to *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora, Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Trametes, Tolypocladium, Trichoderma, Verticillium, Volvariella*, or teleomorphs, or anamorphs, and synonyms, basionyms, or taxonomic equivalents thereof.

In some embodiments of the invention, the filamentous fungal host cell is of the *Trichoderma* species, e.g., *T. longibrachiatum, T. viride* (e.g., ATCC 32098 and 32086), *Hypocrea jecorina* or *T. reesei* (NRRL 15709, ATTC 13631, 56764, 56765, 56466, 56767 and RL-P37 and derivatives thereof; see Sheir-Neiss et al., Appl. Microbiol. Biotechnology, 20 (1984) pp 46-53), *T. koningii*, and *T. harzianum*. In addition, the term "*Trichoderma*" refers to any fungal strain that was previously classified as *Trichoderma* or currently classified as *Trichoderma*. In some embodiments of the invention, the filamentous fungal host cell is of the *Aspergillus* species, e.g., *A. awamori, A. fumigatus, A. japonicus, A. nidulans, A. niger, A. aculeatus, A. foetidus, A. oryzae, A. sojae*, and *A. kawachi*. (Reference is made to Kelly and Hynes (1985) *EMBO J.* 4,475479; NRRL 3112, ATCC 11490, 22342, 44733, and 14331; Yelton M., et al., (1984) *Proc. Natl. Acad. Sci. USA,* 81, 1470-1474; Tilburn et al., (1982) *Gene* 26, 205-221; and Johnston, I. L. et al. (1985) *EMBO J.* 4, 1307-1311). In some embodiments of the invention, the filamentous fungal host cell is of the *Chrysosporium* species, e.g., *C. lucknowense, C. keratinophilum, C. tropicum, C. merdarium, C. inops, C. pannicola*, and *C. zonatum*. In some embodiments of the invention, the filamentous fungal host cell is of the *Myceliophthora* species, e.g., *M. thermophila*. In some embodiments of the invention, the filamentous fungal host cell is of the *Fusarium* species, e.g., *F. bactridioides, F. cerealis, F. crookwellense, F. culmorum, F. graminearum, F. graminum. F. oxysporum, F. roseum*, and *F. venenatum*. In some embodiments of the invention, the filamentous fungal host cell is of the *Neurospora* species, e.g., *N. crassa*. Reference is made to Case, M. E. et al., (1979) *Proc. Natl. Acad. Sci. USA,* 76, 5259-5263; U.S. Pat. No. 4,486,553; and Kinsey, J. A. and J. A. Rambosek (1984) *Molecular and Cellular Biology* 4, 117-122. In some embodiments of the invention, the filamentous fungal host cell is of the *Humicola* species, e.g., *H. insolens, H. grisea*, and *H. lanuginosa*. In some embodiments of the invention, the filamentous fungal host cell is of the *Mucor* species, e.g., *M. miehei* and *M. circinelloides*. In some embodiments of the invention, the filamentous fungal host cell is of the *Rhizopus* species, e.g., *R. oryzae* and *R. niveus*. In some embodiments of the invention, the filamentous fungal host cell is of the *Penicillum* species, e.g., *P. purpurogenum, P. chrysogenum*, and *P. verruculosum*. In some embodiments of the invention, the filamentous fungal host cell is of the *Thielavia* species, e.g., *T. terrestris* and *T. heterothallica*. In some embodiments of the invention, the filamentous fungal host cell is of the *Tolypocladium* species, e.g., *T. inflatum* and *T. geodes*. In some embodiments of the invention, the filamentous fungal host cell is of the *Trametes* species, e.g., *T. villosa* and *T. versicolor*. In some embodiments of the invention, the filamentous fungal host cell is of the *Sporotrichium* species. In some embodiments of the invention, the filamentous fungal host cell is of the *Corynascus* species.

In some embodiments of the invention, a yeast host cell may be a cell of a species of, but not limited to *Candida, Hansenula, Saccharomyces, Schizosaccharomyces, Pichia, Kluyveromyces*, and *Yarrowia*. In some embodiments of the invention, the yeast cell is *Hansenula polymorpha, Saccharomyces cerevisiae, Saccharomyces carlsbergensis, Saccharomyces diastaticus, Saccharomyces norbensis, Saccharomyces kluyveri, Schizosaccharomyces pombe, Pichia pastoris, Pichia finlandica, Pichia trehalophila, Pichia kodamae, Pichia membranaefaciens, Pichia opuntiae, Pichia thermotolerans, Pichia salictaria, Pichia quercuum, Pichia pijperi, Pichia stipitis, Pichia methanolica, Pichia angusta, Kluyveromyces lactis, Candida albicans*, or *Yarrowia lipolytica*.

In some embodiments of the invention, the host cell is an algal cell such as *Chlamydomonas* (e.g., *C. reinhardtii*) and *Phormidium* (P. sp. ATCC29409).

In other embodiments, the host cell is a prokaryotic cell. Suitable prokaryotic cells include gram positive, gram negative and gram-variable bacterial cells. For example and not for limitation, the host cell may be a species of *Agrobacterium, Alicyclobacillus, Anabaena, Anacystis, Acinetobacter, Acidothermus, Arthrobacter, Azobacter, Bacillus, Bifidobacterium, Brevibacterium, Butyrivibrio, Buchnera, Campestris, Camplyobacter, Clostridium, Corynebacterium, Chromatium, Coprococcus, Escherichia, Enterococcus, Enterobacter, Erwinia, Fusobacterium, Faecalibacterium, Francisella, Flavobacterium, Geobacillus, Haemophilus, Helicobacter, Klebsiella, Lactobacillus, Lactococcus, Ilyobacter, Micrococcus, Microbacterium, Mesorhizobium, Methylobacterium, Methylobacterium, Mycobacterium, Neisseria, Pantoea, Pseudomonas, Prochlorococcus, Rhodobacter, Rhodopseudomonas, Rhodopseudomonas, Roseburia, Rhodospirillum, Rhodococcus, Scenedesmus, Streptomyces, Streptococcus, Synecoccus, Saccharomonospora, Staphylococcus, Serratia, Salmonella, Shigella, Thermoanaerobacterium, Tropheryma, Tularensis, Temecula, Thermosynechococcus, Thermococcus, Ureaplasma, Xanthomonas, Xylella, Yersinia* or *Zymomonas*. In some embodiments, the host cell is a species of *Agrobacterium, Acinetobacter, Azobacter, Bacillus, Bifidobacterium, Buchnera, Geobacillus, Campylobacter, Clostridium, Corynebacterium, Escherichia, Enterococcus, Erwinia, Flavobacterium, Lactobacillus, Lactococcus, Pantoea, Pseudomonas, Staphylococcus, Salmonella, Streptococcus, Streptomyces*, or *Zymomonas*.

In yet other embodiments, the bacterial host strain is non-pathogenic to humans. In some embodiments the bacterial host strain is an industrial strain. Numerous bacterial industrial strains are known and suitable in the present invention.

In some embodiments of the invention, the bacterial host cell is of the *Agrobacterium* species, e.g., *A. radiobacter, A. rhizogenes*, and *A. rubi*. In some embodiments of the invention the bacterial host cell is of the *Arthrobacter* species, e.g., *A. aurescens, A. citreus, A. globformis, A. hydrocarboglutamicus, A. mysorens, A. nicotianae, A. paraffineus, A. protophonniae, A. roseoparqffinus, A. sulfureus*, and *A. ureafaciens*. In some embodiments of the invention the bacterial host cell is of the *Bacillus* species, e.g., *B. thuringensis, B. anthracis, B. megaterium, B. subtilis, B. lentus, B. circulans, B. pumilus, B. lautus, B. coagulans, B. brevis, B. firmus, B. alkaophius, B. licheniformis, B. clausii, B. stearothermophilus, B. halodurans* and *B. amyloliquefaciens*. In particular embodiments, the host cell will be an industrial *Bacillus* strain including but not limited to *B. subtilis, B. pumilus, B. licheniformis, B. megaterium, B. clausii, B. stearothermophilus* and *B. amyloliquefaciens*. Some preferred embodiments of a *Bacillus* host cell include *B. subtilis, B. licheniformis, B. megaterium, B. stearothermophilus* and *B. amyloliquefaciens*. In some embodiments the bacterial host cell is of the *Clostridium* species, e.g., *C. acetobutylicum, C. tetani* E88, *C. lituseburense, C. saccharobutylicum, C. perfringens*, and *C. beijerinckii*. In some embodiments the bacterial host cell is of the *Corynebacterium* species e.g., *C. glutamicum* and *C. acetoacidophilum*. In some embodiments the bacterial host cell is of the *Escherichia* species, e.g., *E. coli*. In some embodiments the bacterial host cell is of the *Erwinia* species, e.g., *E. uredovora, E. carotovora, E. ananas, E. herbicola, E. punctata*, and *E. terreus*. In some embodiments the bacterial host cell is of the *Pantoea* species, e.g., *P. citrea*, and *P. agglomerans*. In some embodiments the bacterial host cell is of the *Pseudomonas* species, e.g., *P. putida, P. aeruginosa, P. mevalonii*, and P. sp. D-01 10. In some embodiments the bacterial host cell is of the *Streptococcus* species, e.g., *S. equisimiles, S. pyogenes*, and *S. uberis*. In some embodiments the bacterial host cell is of the *Streptomyces* species, e.g., *S. ambofaciens, S. achromogenes, S. avermitilis, S. coelicolor, S. aureofaciens, S. aureus, S. fungicidicus, S. griseus*, and *S. lividans*. In some embodiments the bacterial host cell is of the *Zymomonas* species, e.g., *Z. mobilis*, and *Z. lipolytica*.

Strains which may be used in the practice of the invention including both prokaryotic and eukaryotic strains, are readily accessible to the public from a number of culture collections such as American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Host cells may be genetically modified to have characteristics that improve protein secretion, protein stability or other properties desirable for expression and/or secretion of a protein. For example, knockout of Alp1 function results in a cell that is protease deficient. Knockout of pyr5 function results in a cell with a pyrimidine deficient phenotype. In particular embodiments host cells are modified to delete endogenous cellulase protein-encoding sequences or otherwise eliminate expression of one or more endogenous cellulases. In one embodiment expression of one or more endogenous cellulases is inhibited to increase production of cellulases of interest. Genetic modification can be achieved by genetic engineering techniques or using classical microbiological techniques, such as chemical or UV mutagenesis and subsequent selection. A combination of recombinant modification and classical selection techniques may be used to produce the organism of interest. Using recombinant technology, nucleic acid molecules can be introduced, deleted, inhibited or modified, in a manner that results in increased yields of cellobiohydrolase within the organism or in the culture. In one genetic engineering approach, homologous recombination can be used to induce targeted gene modifications by specifically targeting a gene in vivo to suppress expression of the encoded protein. In an alternative approach, siRNA, antisense, or ribozyme technology can be used to inhibit gene expression.

In some embodiments, the host cell for expression is a fungal cell (e.g., *Myceliophthora thermophila*) genetically modified to reduce the amount of endogenous cellobiose dehydrogenase (EC 1.1.3.4) and/or other enzyme (e.g., protease) activity that is secreted by the cell. A variety of methods are known in the art for reducing expression of protein in a cell, including deletion of all or part of the gene encoding the protein and site-specific mutagenesis to disrupt expression or activity of the gene product. See, e.g., Chaveroche et al., 2000, *Nucleic Acids Research*, 28:22 e97; Cho et al., 2006, *MPMI* 19: 1, pp. 7-15; Maruyama and Kitamoto, 2008, *Biotechnol Lett* 30:1811-1817; Takahashi et al., 2004, *Mol Gen Genomics* 272: 344-352; and You et al., 2009, *Arch Micriobiol* 191:615-622, the contents of each of which is incorporated by reference herein in its entirety. Random mutagenesis, followed by screening for desired mutations, can also be used. See e.g., Combier et al., 2003, *FEMS Microbiol Lett* 220: 141-8 and Firon et al., 2003, *Eukaryot Cell* 2:247-55, incorporated by reference herein in its entirety.

In some embodiments, the cell is modified to reduce production of endogenous cellobiose dehydrogenases. In some embodiments, the cell is modified to reduce production of cellobiose dehydrogenase (e.g., CDH1 or CDH2). In some embodiments, the host cell has less than 75%, sometimes less than 50%, sometimes less than 30%, sometimes less than 25%, sometimes less than 20%, sometimes less than 15%, sometimes less than 10%, sometimes less than 5%, and sometimes less than 1% of the cellobiose dehydrogenase (e.g., CDH1 and/or CDH2) activity of the corresponding cell in which the gene is not disrupted.

Exemplary *Myceliophthora thermophila* cellobiose dehydrogenases are CDH1 (SEQ ID NO:22), encoded by the nucleotide sequence SEQ ID NO:21, and CDH2 (SEQ ID NO:24), encoded by the nucleotide sequence SEQ ID NO:23. The genomic sequence for the Cdh1 encoding CDH1 has accession number AF074951.1. In one approach, gene disruption is achieved using genomic flanking markers (see, e.g., Rothstein, 1983, *Methods in Enzymology* 101:202-11).

Site-directed mutagenesis may be used to target a particular domain of a protein, in some cases, to reduce enzymatic activity (e.g., glucose-methanol-choline oxido-reductase N and C domains of a cellobiose dehydrogenase or heme binding domain of a cellobiose dehydrogenase; see, e.g., Rotsaert et al., 2001, *Arch. Biochem. Biophys.* 390:206-14, which is incorporated by reference herein in its entirety).

Transformation and Culture

Introduction of a vector or DNA construct into a host cell can be effected by calcium phosphate transfection, DEAE-Dextran mediated transfection, PEG-mediated transformation, electroporation, or other common techniques (See Davis et al., 1986, *Basic Methods in Molecular Biology*, which is incorporated herein by reference).

The engineered host cells can be cultured in conventional nutrient media modified as appropriate for activating promoters, selecting transformants, or amplifying the cellobiohydrolase polynucleotide. Culture conditions, such as temperature, pH and the like, are those previously used with the host cell selected for expression, and will be apparent to those skilled in the art. As noted, many references are available for the culture and production of many cells, including cells of bacterial, plant, animal (especially mammalian) and archebacterial origin. See e.g., Sambrook, Ausubel, and Berger (all supra), as well as Freshney (1994) *Culture of Animal Cells, a Manual of Basic Technique*, third edition, Wiley-Liss, New York and the references cited therein; Doyle and Griffiths (1997) *Mammalian Cell Culture: Essential Techniques* John Wiley and Sons, NY; Humason (1979) *Animal Tissue Techniques*, fourth edition W.H. Freeman and Company; and Ricciardelli, et al., (1989) *In Vitro Cell Dev. Biol.* 25:1016-1024, all of which are incorporated herein by reference. For plant cell culture and regeneration, Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York); Jones, ed. (1984) *Plant Gene Transfer and Expression Protocols*, Humana Press, Totowa, N.J. and *Plant Molecular Biology* (1993) R. R. D. Croy, Ed. Bios Scientific Publishers, Oxford, U.K. ISBN 0 12 198370 6, all of which are incorporated herein by reference. Cell culture media in general are set forth in Atlas and Parks (eds.) *The Handbook of Microbiological Media* (1993) CRC Press, Boca Raton, Fla., which is incorporated herein by reference. Additional information for cell culture is found in available commercial literature such as the *Life Science Research Cell Culture Catalogue* (1998) from Sigma-Aldrich, Inc (St Louis, Mo.) ("Sigma-LSRCCC") and, for example, *The Plant Culture Catalogue* and supplement (1997) also from Sigma-Aldrich, Inc (St Louis, Mo.) ("Sigma-PCCS"), all of which are incorporated herein by reference.

In some embodiments, cells expressing the cellobiohydrolase polypeptides of the invention are grown under batch or continuous fermentations conditions. Classical batch fermentation is a closed system, wherein the compositions of the medium is set at the beginning of the fermentation and is not subject to artificial alternations during the fermentation. A variation of the batch system is a fed-batch fermentation which also finds use in the present invention. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth. Continuous fermentation systems strive to maintain steady state growth conditions. Methods for modulating nutrients and growth factors for continuous fermentation processes as well as techniques for maximizing the rate of product formation are well known in the art of industrial microbiology.

Cell-free transcription/translation systems can also be employed to produce cellobiohydrolase polypeptides using the polynucleotides of the present invention. Several such systems are commercially available. A general guide to in vitro transcription and translation protocols is found in Tymms (1995) *In vitro Transcription and Translation Protocols: Methods in Molecular Biology*, Volume 37, Garland Publishing, NY, which is incorporated herein by reference.

IX. Production and Recovery of Cellobiohydrolase Variants

In another aspect, the present invention is directed to a method of making a polypeptide having cellobiohydrolase activity or a biologically active fragment thereof. In some embodiments, the method comprises: providing a host cell transformed with a polynucleotide encoding an amino acid sequence that comprises at least about 70% (or at least about 75%, at least about 80%, at least about 85%, at least about 90%, at least about 95%, at least about 96%, at least about 97%, at least about 98%, or at least about 99%) sequence identity to SEQ ID NO:1 and comprises one or more substitutions or substitution sets as described herein (e.g., in Table 3 or Table 4); culturing the transformed host cell in a culture medium under conditions in which the host cell expresses the encoded cellobiohydrolase polypeptide; and optionally recovering or isolating the expressed cellobiohydrolase polypeptide, or recovering or isolating the culture medium containing the expressed cellobiohydrolase polypeptide. The method further provides optionally lysing the transformed host cells after expressing the encoded cellobiohydrolase polypeptide and optionally recovering or isolating the expressed cellobiohydrolase polypeptide from the cell lysate. The present invention further provides a method of making an cellobiohydrolase polypeptide, said method comprising cultivating a host cell transformed with a cellobiohydrolase polypeptide under conditions suitable for the production of the cellobiohydrolase polypeptide and recovering the cellobiohydrolase polypeptide.

Typically, recovery or isolation of the cellobiohydrolase polypeptide is from the host cell culture medium, the host cell or both, using protein recovery techniques that are well known in the art, including those described herein. Cells are typically harvested by centrifugation, disrupted by physical or chemical means, and the resulting crude extract may be retained for further purification. Microbial cells employed in expression of proteins can be disrupted by any convenient method, including freeze-thaw cycling, sonication, mechanical disruption, or use of cell lysing agents, or other methods, which are well known to those skilled in the art.

The resulting polypeptide may be recovered/isolated and optionally purified by any of a number of methods known in the art. For example, the polypeptide may be isolated from the nutrient medium by conventional procedures including, but not limited to, centrifugation, filtration, extraction, spray-drying, evaporation, chromatography (e.g., ion exchange, affinity, hydrophobic interaction, chromatofocusing, and size exclusion), or precipitation. Protein refolding steps can be used, as desired, in completing the configuration of the mature protein. Finally, high performance liquid chromatography (HPLC) can be employed in the final purification steps. Purification of BGL1 is described in Parry et al., 2001, *Biochem. J.* 353:117, and Hong et al., 2007, *Appl. Microbiol. Biotechnol.* 73:1331, both incorporated herein by reference. In addition to the references noted supra, a variety of purification methods are well known in the art, including, for example, those set forth in Sandana (1997) *Bioseparation of Proteins*, Academic Press, Inc.; Bollag et al. (1996) *Protein Methods, 2nd* Edition, Wiley-Liss, NY; Walker (1996) *The Protein Protocols Handbook Humana Press*, NJ; Harris and Angal (1990) *Protein Purification Applications: A Practical Approach*, IRL Press at Oxford, Oxford, England; Harris and Angal *Protein Purification Methods: A Practical Approach*, IRL Press at Oxford, Oxford, England; Scopes (1993) *Protein Purification: Principles and Practice 3rd Edition*, Springer Verlag, NY; Janson and Ryden (1998) *Protein Purification: Principles, High Resolution Methods and Applications, Second Edition*, Wiley-VCH, NY; and Walker (1998) *Protein Protocols on CD-ROM*, Humana Press, NJ, all of which are incorporated herein by reference.

Immunological methods may be used to purify cellobiohydrolase polypeptides. In one approach, antibody raised against the cellobiohydrolase polypeptides (e.g., against a polypeptide comprising SEQ ID NO:1 or an immunogenic fragment thereof) using conventional methods is immobilized on beads, mixed with cell culture media under conditions in which the cellobiohydrolase is bound, and precipitated. In a related approach, immunochromatography is used.

As noted, in some embodiments the cellobiohydrolase is expressed as a fusion protein including a non-enzyme portion. In some embodiments the cellobiohydrolase sequence is fused to a purification facilitating domain. As used herein, the term "purification facilitating domain" refers to a domain that mediates purification of the polypeptide to which it is fused. Suitable purification domains include metal chelating peptides, histidine-tryptophan modules that allow purification on immobilized metals, a sequence which binds glutathione (e.g., GST), a hemagglutinin (HA) tag (corresponding to an epitope derived from the influenza hemagglutinin protein; Wilson et al., 1984, *Cell* 37:767), maltose binding protein sequences, the FLAG epitope utilized in the FLAGS extension/affinity purification system (Immunex Corp, Seattle, Wash.), and the like. The inclusion of a protease-cleavable polypeptide linker sequence between the purification domain and the CBH2a polypeptide is useful to facilitate purification. One expression vector contemplated for use in the compositions and methods described herein provides for expression of a fusion protein comprising a polypeptide of the invention fused to a polyhistidine region separated by an enterokinase cleavage site. The histidine residues facilitate purification on IMIAC (immobilized metal ion affinity chromatography, as described in Porath et al., 1992, *Protein Expression and Purification* 3:263-281) while the enterokinase cleavage site provides a means for separating the CBH2a polypeptide from the fusion protein. pGEX vectors (Promega; Madison, Wis.) may also be used to express foreign polypeptides as fusion proteins with glutathione S-transferase (GST). In general, such fusion proteins are soluble and can easily be purified from lysed cells by adsorption to ligand-agarose beads (e.g., glutathione-agarose in the case of GST-fusions) followed by elution in the presence of free ligand.

X. Methods of Using Cellobiohydrolase Variants

The cellobiohydrolase variants and biologically active fragments as described herein have multiple industrial applications, including but are not limited to, sugar production (e.g. glucose syrups), biofuels production, textile treatment, pulp or paper treatment, and applications in detergents or animal feed. A host cell containing a cellobiohydrolase variant of the present invention may be used without recovery and purification of the recombinant cellobiohydrolase, e.g., for use in a large scale biofermentor. Alternatively, the recombinant cellobiohydrolase variant may be expressed and purified from the host cell. The cellobiohydrolase variants of the present invention may also be used according to the methods of Section III ("Improved Saccharification Process") of WO 2010/120557, the contents of which are incorporated by reference herein.

The variant cellobiohydrolases that have been described herein are particularly useful for breaking down cellulose to smaller oligosaccharides, disaccharides and monosaccharides. In some embodiments, the variant cellobiohydrolases are useful in saccharification methods. In some embodiments, the variant cellobiohydrolases may be used in combination with other cellulase enzymes including, for example, conventional enzymatic saccharification methods, to produce fermentable sugars.

Therefore, in one aspect the present invention provides a method of producing an end-product from a cellulosic substrate, the method comprising contacting the cellulosic substrate with a cellobiohydrolase variant as described herein (and optionally other cellulases) under conditions in which fermentable sugars are produced, and contacting fermentable sugars with a microorganism in a fermentation to produce the end-product. In some embodiments, the method further comprises pretreating the cellulosic substrate to increase its susceptibility to hydrolysis prior to contacting the cellulosic substrate with the cellobiohydrolase variant (and optionally other cellulases).

In some embodiments, enzyme compositions comprising the cellobiohydrolase variants of the present invention may be reacted with a biomass substrate in the range of about 25° C. to 100° C., about 30° C. to 90° C., about 30° C. to 80° C., and about 30° C. to 70° C. Also the biomass may be reacted with the cellobiohydrolase enzyme compositions at about 25° C., at about 30° C., at about 35° C., at about 40° C., at about 45° C., at about 50° C., at about 55° C., at about 60° C., at about 65° C., at about 70° C., at about 75° C., at about 80° C., at about 85° C., at about 90° C., at about 95° C. and at about 100° C. Generally the pH range will be from about pH 3.0 to 8.5, pH 3.5 to 8.5, pH 4.0 to 7.5, pH 4.0 to 7.0 and pH 4.0 to 6.5. The incubation time may vary for example from 1.0 to 240 hours, from 5.0 to 180 hrs and from 10.0 to 150 hrs. For example, the incubation time will be at least 1 hr, at least 5 hrs, at least 10 hrs, at least 15 hrs, at least 25 hrs, at least 50 hr, at least 100 hrs, at least 180 and the like. Incubation of the cellulase under these conditions and subsequent contact with the substrate may result in the release of substantial amounts of fermentable sugars from the substrate (e.g., glucose when the cellulase is combined with β-glucosidase). For example, at least 20%, at least 30%, at least 40%, at least 50%, at least 60%, at least 70%, at least 80%, at least 90% or more fermentable sugar may be available as compared to the release of sugar by a wild-type polypeptide.

In some embodiments, an end-product of a fermentation is any product produced by a process including a fermentation step using a fermenting organism. Examples of end-products of a fermentation include, but are not limited to, alcohols (e.g., fuel alcohols such as ethanol and butanol), organic acids (e.g., citric acid, acetic acid, lactic acid, gluconic acid, and succinic acid), glycerol, ketones, diols, amino acids (e.g., glutamic acid), antibiotics (e.g., penicillin and tetracycline), vitamins (e.g., beta-carotine and B12), hormones, and fuel molecules other than alcohols (e.g., hydrocarbons).

In some embodiments, the fermentable sugars produced by the methods of the present invention may be used to produce an alcohol (such as, for example, ethanol, butanol, and the like). The variant cellobiohydrolases of the present invention may be utilized in any method used to generate alcohols or other biofuels from cellulose, and are not limited necessarily to those described herein. Two methods commonly employed are the separate saccharification and fermentation (SHF) method (see, Wilke et al., Biotechnol. Bioengin. 6:155-75 (1976)) or the simultaneous saccharification and fermentation (SSF) method, disclosed, for example, in U.S. Pat. Nos. 3,990,944 and 3,990,945.

The SHF method of saccharification comprises the steps of contacting a cellulase with a cellulose containing substrate to enzymatically break down cellulose into fermentable sugars (e.g., monosaccharides such as glucose), contacting the fermentable sugars with an alcohol-producing microorganism to produce alcohol (e.g., ethanol or butanol) and recovering the alcohol. In some embodiments, the method of consolidated bioprocessing (CBP) can be used, where the cellulase production from the host is simultaneous with saccharification and fermentation either from one host or from a mixed cultivation.

In addition to SHF methods, a SSF method may be used. In some cases, SSF methods result in a higher efficiency of alcohol production than is afforded by the SHF method (Drissen et al., Biocatalysis and Biotransformation 27:27-35 (2009). One disadvantage of SSF over SHF is that higher temperatures are required for SSF than for SHF. In one embodiment, the present invention claims cellobiohydrolase polypeptides that have higher thermostability than a wild-type cellobiohydrolase and one practicing the present invention could expect an increase in ethanol production if using the cellulases described here in combination with SSF.

For cellulosic substances to be used effectively as substrates for the saccharification reaction in the presence of a cellulase of the present invention, it can be desirable to pretreat the substrate. Means of pretreating a cellulosic substrate are known in the art, including but not limited to chemical pretreatment (e.g., ammonia pretreatment, dilute acid pretreatment, dilute alkali pretreatment, or solvent exposure), physical pretreatment (e.g., steam explosion or irradiation), mechanical pretreatment (e.g., grinding or milling) and biological pretreatment (e.g., application of lignin-solubilizing microorganisms), and the present invention is not limited by such methods.

Any alcohol producing microorganism such as those known in the art, e.g., *Saccharomyces cerevisiae*, can be employed with the present invention for the fermentation of fermentable sugars to alcohols and other end-products.

The fermentable sugars produced from the use of one or more cellobiohydrolase variants encompassed by the invention may be used to produce other end-products besides alcohols, such as but not limited to other biofuels compounds, acetone, an amino acid (e.g., glycine, lysine, and the like), organic acids (e.g., lactic acids and the like), glycerol, ascorbic acid, a diol (e.g., 1,3-propanediol, butanediol, and the like), vitamins, hormones, antibiotics, other chemicals, and animal feeds.

The cellobiohydrolase variants as described herein are further useful in the pulp and paper industry. In the pulp and paper industry, neutral cellulases can be used, for example, in deinking of different recycled papers and paperboards having neutral or alkaline pH, in improving the fiber quality, or increasing the drainage in paper manufacture. Other examples include, for example, the removal of printing paste thickener and excess dye after textile printing.

Lignocellulosic Feedstocks

The term "lignocellulosic feedstock" refers to any type of plant biomass such as, but not limited to, non-woody plant biomass, cultivated crops such as, but not limited to grasses, for example, but not limited to, C4 grasses, such as switch grass, cord grass, rye grass, miscanthus, reed canary grass, or a combination thereof, sugar processing residues, for example, but not limited to, baggase, such as sugar cane bagasse, beet pulp, or a combination thereof, agricultural residues, for example, but not limited to, soybean stover, corn stover, rice straw, sugar cane straw, rice hulls, barley straw, corn cobs, wheat straw, canola straw, oat straw, oat hulls, corn fiber, or a combination thereof, forestry biomass for example, but not limited to, recycled wood pulp fiber, sawdust, hardwood, for example aspen wood, softwood, or a combination thereof. Furthermore, the lignocellulosic feedstock may comprise cellulosic waste material or forestry waste materials such as, but not limited to, newsprint, cardboard and the like. Lignocellulosic feedstock may comprise one species of fiber or, alternatively, lignocellulosic feedstock may comprise a mixture of fibers that originate from different lignocellulosic feedstocks. In addition, the lignocellulosic feedstock may comprise fresh lignocellulosic feedstock, partially dried lignocellulosic feedstock, fully dried lignocellulosic feedstock, or a combination thereof.

Lignocellulosic feedstocks often comprise cellulose in an amount greater than about 20%, more preferably greater than about 30%, more preferably greater than about 40% (w/w). For example, in some embodiments, the lignocellulosic material may comprise from about 20% to about 90% (w/w) cellulose, or any amount therebetween. Furthermore, the lignocellulosic feedstock comprises lignin in an amount greater than about 10%, more typically in an amount greater than about 15% (w/w). The lignocellulosic feedstock may also comprise small amounts of sucrose, fructose and starch. The lignocellulosic feedstock is generally first subjected to size reduction by methods including, but not limited to, milling, grinding, agitation, shredding, compression/expansion, or other types of mechanical action. Size reduction by mechanical action can be performed by any type of equipment adapted for the purpose, for example, but not limited to, hammer mills, tub-grinders, roll presses, refiners and hydrapulpers. At least 90% by weight of the particles produced from the size reduction may have a length less than between about 1/16 and about 4 in. The measurement may be a volume or a weight average length.

The preferable equipment for the particle size reduction is a hammer mill or shredder. Subsequent to size reduction, the feedstock is typically slurried in water. This allows the feedstock to be pumped.

Lignocellulosic feedstocks of particle size less than about 6 inches may not require size reduction.

The feedstock may be slurried prior to pretreatment. In one embodiment of the invention, the consistency of the feedstock slurry is between about 2% and about 30% and more typically between about 4% and about 15%. Optionally, the slurry is subjected to a water or acid soaking operation prior to pretreatment.

Prior to pretreatment, the slurry may be dewatered using known methodologies to reduce steam and chemical usage. Examples of dewatering devices include pressurized screw presses, such as those described in WO 2010/022511 (incorporated herein by reference), pressurized filters, and extruders.

A pretreated lignocellulosic feedstock, or pretreated lignocellulose, is a lignocellulosic feedstock that has been subjected to physical and/or chemical processes to make the fiber more accessible and/or receptive to the actions of cellulolytic enzymes.

The pretreatment may be carried out to hydrolyze the hemicellulose, or a portion thereof, that is present in the lignocellulosic feedstock to monomeric pentose and hexose sugars, for example xylose, arabinose, mannose, galactose, or a combination thereof. For example, the pretreatment may be carried out so that nearly complete hydrolysis of the hemicellulose and a small amount of conversion of cellulose to glucose occurs. During the pretreatment, typically an acid concentration in the aqueous slurry from about 0.02% (w/w) to about 2% (w/w), or any amount therebetween, is used for the treatment of the lignocellulosic feedstock. The acid may be, but is not limited to, hydrochloric acid, nitric acid, or sulfuric acid. For example, the acid used during pretreatment is sulfuric acid.

One method of performing acid pretreatment of the feedstock is steam explosion using the process conditions set out in U.S. Pat. No. 4,461,648. Another method of pretreating the feedstock slurry involves continuous pretreatment, meaning that the lignocellulosic feedstock is pumped though a reactor continuously. Continuous acid pretreatment is familiar to those skilled in the art; see, for example, U.S. Pat. No. 7,754,457.

The pretreatment may also be conducted with alkali. In contrast to acid pretreatment, pretreatment with alkali may not hydrolyze the hemicellulose component of the feedstock. For example, the alkali may react with acidic groups present on the hemicellulose to open up the surface of the substrate. The addition of alkali may also alter the crystal structure of the cellulose so that it is more amenable to hydrolysis. Examples of alkali that may be used in the pretreatment include ammonia, ammonium hydroxide, potassium hydroxide, and sodium hydroxide.

An example of a suitable alkali pretreatment is Ammonia Freeze Explosion, Ammonia Fiber Explosion or Ammonia Fiber Expansion ("AFEX" process). According to this process, the lignocellulosic feedstock is contacted with ammonia or ammonium hydroxide in a pressure vessel for a sufficient time to enable the ammonia or ammonium hydroxide to alter the crystal structure of the cellulose fibers. The pressure is then rapidly reduced, which allows the ammonia to flash or boil and explode the cellulose fiber structure. (See U.S. Pat. Nos. 5,171,592; 5,037,663; 4,600,590; 6,106,888; 4,356,196; 5,939,544; 6,176,176; 5,037,663 and 5,171,592). The flashed ammonia may then be recovered according to known processes.

Dilute ammonia pretreatment utilizes more dilute solutions of ammonia or ammonium hydroxide than AFEX (see WO 2009/045651 and US 2007/0031953). Such a pretreatment process may or may not produce any monosaccharides.

Yet a further non-limiting example of a pretreatment process for use in the present invention includes chemical treatment of the feedstock with organic solvents. Organic liquids in pretreatment systems are described by Converse et al. (U.S. Pat. No. 4,556,430; incorporated herein by reference), and such methods have the advantage that the low boiling point liquids easily can be recovered and reused. Other pretreatments, such as the Organosolv™ process, also use organic liquids (see U.S. Pat. No. 7,465,791, which is also incorporated herein by reference). Subjecting the feedstock to pressurized water may also be a suitable pretreatment method (see Weil et al. (1997) *Appl. Biochem. Biotechnol.* 68(1-2): 21-40, which is incorporated herein by reference).

The pretreated lignocellulosic feedstock may be processed after pretreatment by any of several steps, such as dilution with water, washing with water, buffering, filtration, or centrifugation, or a combination of these processes, prior to enzymatic hydrolysis, as is familiar to those skilled in the art.

The pretreatment produces a pretreated feedstock composition (e.g., a pretreated feedstock slurry) that contains a soluble component including the sugars resulting from hydrolysis of the hemicellulose, optionally acetic acid and other inhibitors, and solids including unhydrolyzed feedstock and lignin.

The soluble components of the pretreated feedstock composition may be separated from the solids to produce a soluble fraction. The soluble fraction, which includes the sugars released during pretreatment and other soluble components, including inhibitors, may then be sent to fermentation. It will be understood, however, that if the hemicellulose is not effectively hydrolyzed during the pretreatment, it may be desirable to include a further hydrolysis step or steps with enzymes or by further alkali or acid treatment to produce fermentable sugars. The foregoing separation may be carried out by washing the pretreated feedstock composition with an aqueous solution to produce a wash stream, and a solids stream comprising the unhydrolyzed, pretreated feedstock. Alternatively, the soluble component is separated from the solids by subjecting the pretreated feedstock composition to a solids-liquid separation, using known methods such as centrifugation, microfiltration, plate and frame filtration, cross-flow filtration, pressure filtration, vacuum filtration, and the like. Optionally, a washing step may be incorporated into the solids-liquids separation. The separated solids, which contain cellulose, may then be sent to enzymatic hydrolysis with cellulase enzymes in order to convert the cellulose to glucose.

The pretreated feedstock composition may be fed to the fermentation without separation of the solids contained therein. After the fermentation, the unhydrolyzed solids may be subjected to enzymatic hydrolysis with cellulase enzymes to convert the cellulose to glucose.

Prior to hydrolysis with cellulase enzymes, the pH of the pretreated feedstock slurry may be adjusted to a value that is amenable to the cellulase enzymes, which is typically between about 4 and about 6, although the pH can be higher if alkalophilic cellulases are used.

Enzyme Mixtures

In another aspect, the invention provides an enzyme mixture that comprises a cellobiohydrolase variant polypeptide as described herein or a biologically active fragment thereof. In some embodiments, the enzymes of the enzyme mixture may be secreted from a host cell and in other embodiments, the enzymes of the enzyme mixture may not be secreted. The enzyme mixture may be cell-free, or in alternative embodiments, may not be separated from host cells that secrete an enzyme mixture component. A cell-free enzyme mixture typically comprises enzymes that have been separated from any cells. Cell-free enzyme mixtures can be prepared by any of a variety of methodologies that are known in the art, such as filtration or centrifugation methodologies. In certain embodiments, the enzyme mixture can be, for example, partially cell-free, substantially cell-free, or entirely cell-free. In some embodiments, one or more enzymes of the enzyme mixture are not secreted by the host cell. The cells may be lysed to release the enzyme(s). Enzymes may be recovered from the cell lysate or the cell lysate may be combined, with partial purification or without further purification, with the substrate.

The cellobiohydrolase variant and any additional enzymes present in an enzyme mixture may be secreted from a single genetically modified host cell or by different microbes in combined or separate fermentations. Similarly, the cellobiohydrolase variant and any additional enzymes present in the enzyme mixture may be expressed individually or in sub-groups from different strains of different organisms and the enzymes combined in vitro to make the enzyme mixture. It is also contemplated that the cellobiohydrolase variant and any additional enzymes in the enzyme mixture may be expressed individually or in sub-groups from different strains of a single organism, and the enzymes combined to make the enzyme mixture. In some embodiments, all of the enzymes are expressed from a single host organism, such as a genetically modified fungal cell.

In some embodiments, the enzyme mixture comprises other types of cellulases, selected from but not limited to cellobiohydrolase, endoglucanase, β-glucosidase, and glycoside hydrolase 61 protein (GH61) cellulases. These enzymes may be wild-type or recombinant enzymes. In some embodiments, the cellobiohydrolase is a type 1 cellobiohydrolase, e.g., a *T. reesei* cellobiohydrolase I. In some embodiments, the endoglucanase comprises a catalytic domain derived from the catalytic domain of a *Streptomyces avermitilis* endoglucanase. See US 2010/0267089, incorporated herein by reference. In some embodiments, the at least one cellulase is derived from *Acidothermus cellulolyticus, Thermobifida fusca, Humicola grisea, Myceliophthora thermophila, Chaetomium thermophilum, Acremonium* sp., *Thielavia* sp, *Trichoderma reesei, Aspergillus* sp., or a *Chrysosporium* sp. Cellulase enzymes of the cellulase mixture work together resulting in decrystallization and hydrolysis of the cellulose from a biomass substrate to yield fermentable sugars, such as but not limited to glucose (See Brigham et al., 1995, in Handbook on Bioethanol (C. Wyman ed.) pp 119-141, Taylor and Francis, Washington D.C., which is incorporated herein by reference).

Cellulase mixtures for efficient enzymatic hydrolysis of cellulose are known (see, e.g., Viikari et al., 2007, "Thermostable enzymes in lignocellulose hydrolysis" *Adv Biochem Eng Biotechnol* 108:121-45, and US Pat. publications US 2009/0061484; US 2008/0057541; and US 2009/0209009 to Iogen Energy Corp.), each of which is incorporated herein by reference for all purposes. In some embodiments, mixtures of purified naturally occurring or recombinant enzymes are combined with cellulosic feedstock or a product of cellulose hydrolysis. Alternatively or in addition, one or more cell populations, each producing one or more naturally occurring or recombinant cellulases, may be combined with cellulosic feedstock or a product of cellulose hydrolysis.

In some embodiments, the enzyme mixture comprises commercially available purified cellulases. Commercial cellulases are known and available (e.g., C2730 cellulase from *Trichoderma reesei* ATCC No. 25921 available from Sigma-Aldrich, Inc.; and C9870 ACCELLERASE™ 1500, available from Genencor).

In some embodiments, the enzyme mixture comprises an isolated CBH2a variant as described herein and at least one or more of an isolated cellobiohydrolase type 1a such as a CBH1a, an isolated endoglucanase (EG) such as a type 2 endoglucanase (EG2), an isolated β-glucosidase (Bgl), and an isolated glycoside hydrolase 61 protein (GH61). In some embodiments, at least 20%, at least 25%, at least 30%, at least 35%, at least 40%, at least 45%, or at least 50% of the enzyme mixture is a CBH2a variant. In some embodiments, the enzyme mixture further comprises a cellobiohydrolase type 1a (e.g., CBH1a), and the CBH2a variant and the CBH1a together comprise at least 25%, at least 30%, at least 35%, at least 40%, at least 45%, at least 50%, at least 55%, at least 60%, at least 65%, at least 70%, at least 75%, or at least 80% of the enzyme mixture. In some embodiments, the enzyme mixture further comprises a β-glucosidase (Bgl), and the CBH2a variant, the CBH1a, and the Bgl together comprise at least 30%, at least 35%, at least 40%, at least 45%, at least 50%, at least 55%, at least 60%, at least 65%, at least 70%, at least 75%, at least 80%, or at least 85% of the enzyme mixture. In some embodiments, the enzyme mixture further comprises an endoglucanase (EG), and the CBH2a variant, the CBH1a, the Bgl, and the EG together comprise at least 35%, at least 40%, at least 45%, at least 50%, at least 55%, at least 60%, at least 65%, at least 70%, at least 75%, at least 80%, at least 85%, or at least 90% of the enzyme mixture. In some embodiments, the enzyme mixture comprises a CBH2a variant as described herein, a cellobiohydrolase type 1a (CBH1a), a β-glucosidase (Bgl), an endoglucanase (EG), and a glycoside hydrolase 61 protein (GH61). In some embodiments, the enzyme mixture composition comprises isolated cellulases in the following proportions by weight (wherein the total weight of the cellulases is 100%): about 20%-10% of EG, about 20%-10% of Bgl, about 30%-25% of CBH1a, about 10%-30% of GH61, and about 20%-25% of a CBH2a variant of the present invention. In some embodiments, the enzyme mixture composition comprises isolated cellulases in the following proportions by weight: about 20%-10% of EG, about 25%-15% of Bgl, about 20%-30% of CBH1a, about 10%-15% of GH61, and about 25%-30% of a CBH2a variant of the present invention. In some embodiments, the enzyme mixture composition comprises isolated cellulases in the following proportions by weight: about 10%-15% of EG, about 20%-25% of Bgl, about 30%-20% of CBH1a, about 15%-5% of GH61, and about 25%-35% of a CBH2a variant of the present invention. In some embodiments, the enzyme mixture composition comprises isolated cellulases in the following proportions by weight: about 15%-5% of EG, about 15%-10% of Bgl, about 45%-30% of CBH1a, about 25%-5% of GH61, and about 40%-10% of a CBH2a variant of the present invention. In some embodiments, the enzyme mixture composition comprises isolated cellulases in the following proportions by weight: about 10% of EG, about 15% of Bgl, about 40% of CBH1a, about 25% of GH61, and about 10% of a CBH2a variant of the present invention. In some embodiments, the enzyme mixture composition comprises isolated cellulases in the following proportions by weight: about 0% of EG, about 15%-10% of Bgl, about 30%-40% of CBH1a, about 15%-10% of GH61, and about 30%-40% of a CBH2a variant of the present invention. In some embodiments, the enzyme component comprises more than 1 CBH2a variant (e.g., 2, 3 or 4 different CBH2a variants as disclosed herein). In some embodiments, an enzyme mixture composition of the invention can also contain one or more additional proteins such as those listed below. In some embodiments, an enzyme mixture composition of the invention can also contain one or more additional enzymes other than the EG, Bgl, CBH1a, GH61, and/or CBH2a variant recited herein, such as the enzymes listed below. In some embodiments, an enzyme mixture composition of the invention can also contain one or more additional cellulases other than the EG, Bgl, CBH1a, GH61, and/or CBH2a variant recited herein.

A cellobiohydrolase variant polypeptide of the invention may also be present in mixtures with non-cellulase enzymes that degrade cellulose, hemicellulose, pectin, and/or lignocellulose.

A "hemicellulase" as used herein, refers to a polypeptide that can catalyze hydrolysis of hemicellulose into small polysaccharides such as oligosaccharides, or monomeric saccharides. Hemicellullases include xylan, glucuonoxylan, arabinoxylan, glucomannan and xyloglucan. Hemicellulases include, for example, the following: endoxylanases, β-xylosidases, α-L-arabinofuranosidases, a-D-glucuronidases, feruloyl esterases, coumarolyl esterases, α-galactosidases, β-galactosidases, β-mannanases, and β-mannosidases. An enzyme mixture may therefore comprise a cellobiohydrolase variant of the invention and one or more hemicellulases.

An endoxylanase (EC 3.2.1.8) catalyzes the endohydrolysis of 1,4-β-D-xylosidic linkages in xylans. This enzyme may also be referred to as endo-1,4-β-xylanase or 1,4-β-D-xylan xylanohydrolase. An alternative is EC 3.2.1.136, a glucuronoarabinoxylan endoxylanase, an enzyme that is able to hydrolyse 1,4 xylosidic linkages in glucuronoarabinoxylans.

A β-xylosidase (EC 3.2.1.37) catalyzes the hydrolysis of 1,4-β-D-xylans, to remove successive D-xylose residues from the non-reducing termini. This enzyme may also be referred to as xylan 1,4-β-xylosidase, 1,4-β-D-xylan xylohydrolase, exo-1,4-β-xylosidase, or xylobiase.

An α-L-arabinofuranosidase (EC 3.2.1.55) catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, arabinofuranosidase, polysaccharide alpha-L-arabinofuranosidase, alpha-L-arabinofuranoside hydrolase, L-arabinosidase and alpha-L-arabinanase.

An alpha-glucuronidase (EC 3.2.1.139) catalyzes the hydrolysis of an alpha-D-glucuronoside to D-glucuronate and an alcohol.

An acetylxylanesterase (EC 3.1.1.72) catalyzes the hydrolysis of acetyl groups from polymeric xylan, acetylated xylose, acetylated glucose, alpha-napthyl acetate, and p-nitrophenyl acetate.

A feruloyl esterase (EC 3.1.1.73) has 4-hydroxy-3-methoxycinnamoyl-sugar hydrolase activity (EC 3.1.1.73) that catalyzes the hydrolysis of the 4-hydroxy-3-methoxycinnamoyl (feruloyl) group from an esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II.

A coumaroyl esterase (EC 3.1.1.73) catalyzes a reaction of the form: coumaroyl-saccharide+H(2)O=coumarate+saccharide. The saccharide may be, for example, an oligosaccharide or a polysaccharide. This enzyme may also be referred to as trans-4-coumaroyl esterase, trans-p-coumaroyl esterase, p-coumaroyl esterase or p-coumaric acid esterase. The enzyme also falls within EC 3.1.1.73 so may also be referred to as a feruloyl esterase.

An α-galactosidase (EC 3.2.1.22) catalyzes the hydrolysis of terminal, non-reducing α-D-galactose residues in α-D-galactosides, including galactose oligosaccharides, galactomannans, galactans and arabinogalactans. This enzyme may also be referred to as melibiase.

A β-galactosidase (EC 3.2.1.23) catalyzes the hydrolysis of terminal non-reducing β-D-galactose residues in β-D-galactosides. Such a polypeptide may also be capable of hydrolyzing α-L-arabinosides. This enzyme may also be referred to as exo-(1→4)-β-D-galactanase or lactase.

A β-mannanase (EC 3.2.1.78) catalyzes the random hydrolysis of 1,4-β-D-mannosidic linkages in mannans, galactomannans and glucomannans. This enzyme may also be referred to as mannan endo-1,4-β-mannosidase or endo-1,4-mannanase.

A β-mannosidase (EC 3.2.1.25) catalyzes the hydrolysis of terminal, non-reducing β-D-mannose residues in β-D-mannosides. This enzyme may also be referred to as mannanase or mannase.

A glucoamylase (EC 3.2.1.3) is an enzyme which catalyzes the release of D-glucose from non-reducing ends of oligo- and poly-saccharide molecules. Glucoamylase is also generally considered a type of amylase known as amylo-glucosidase.

An amylase (EC 3.2.1.1) is a starch cleaving enzyme that degrades starch and related compounds by hydrolyzing the α-1,4 and/or α-1,6 glucosidic linkages in an endo- or an exo-acting fashion. Amylases include α-amylases (EC 3.2.1.1); β-amylases (3.2.1.2), amylo-amylases (EC 3.2.1.3), α-glucosidases (EC 3.2.1.20), pullulanases (EC 3.2.1.41), and isoamylases (EC 3.2.1.68). In some embodiments, the amylase is an α-amylase.

One or more enzymes that degrade pectin may also be included in an enzyme mixture that comprises a cellobiohydrolase variant of the invention. A pectinase catalyzes the hydrolysis of pectin into smaller units such as oligosaccharide or monomeric saccharides. An enzyme mixture may comprise any pectinase, for example an endo-polygalacturonase, a pectin methyl esterase, an endo-galactanase, a pectin acetyl esterase, an endo-pectin lyase, pectate lyase, alpha rhamnosidase, an exo-galacturonase, an exo-polygalacturonate lyase, a rhamnogalacturonan hydrolase, a rhamnogalacturonan lyase, a rhamnogalacturonan acetyl esterase, a rhamnogalacturonan galacturonohydrolase or a xylogalacturonase.

An endo-polygalacturonase (EC 3.2.1.15) catalyzes the random hydrolysis of 1,4-α-D-galactosiduronic linkages in pectate and other galacturonans. This enzyme may also be referred to as polygalacturonase pectin depolymerase, pectinase, endopolygalacturonase, pectolase, pectin hydrolase, pectin polygalacturonase, poly-α-1,4-galacturonide glycanohydrolase, endogalacturonase; endo-D-galacturonase or poly(1,4-α-D-galacturonide) glycanohydrolase.

A pectin methyl esterase (EC 3.1.1.11) catalyzes the reaction: pectin+n $H_2O$=n methanol+pectate. The enzyme may also been known as pectinesterase, pectin demethoxylase, pectin methoxylase, pectin methylesterase, pectase, pectinoesterase or pectin pectylhydrolase.

A endo-galactanase (EC 3.2.1.89) catalyzes the endohydrolysis of 1,4-β-D-galactosidic linkages in arabinogalactans. The enzyme may also be known as arabinogalactan endo-1,4-β-galactosidase, endo-1,4-β-galactanase, galactanase, arabinogalactanase or arabinogalactan 413-D-galactanohydrolase.

A pectin acetyl esterase catalyzes the deacetylation of the acetyl groups at the hydroxyl groups of GalUA residues of pectin.

An endo-pectin lyase (EC 4.2.2.10) catalyzes the eliminative cleavage of (1→4)-α-D-galacturonan methyl ester to give oligosaccharides with 4-deoxy-β-O-methyl-α-D-galact-4-enuronosyl groups at their non-reducing ends. The enzyme may also be known as pectin lyase, pectin trans-eliminase; endo-pectin lyase, polymethylgalacturonic transeliminase, pectin methyltranseliminase, pectolyase, PL, PNL or PMGL or (1→4)-β-O-methyl-α-D-galacturonan lyase.

A pectate lyase (EC 4.2.2.2) catalyzes the eliminative cleavage of (1→4)-α-D-galacturonan to give oligosaccharides with 4-deoxy-α-D-galact-4-enuronosyl groups at their non-reducing ends. The enzyme may also be known polygalacturonic transeliminase, pectic acid transeliminase, polygalacturonate lyase, endopectin methyltranseliminase, pectate transeliminase, endogalacturonate transeliminase, pectic acid lyase, pectic lyase, α-1,4-D-endopolygalacturonic acid lyase, PGA lyase, PPase-N, endo-α-1,4-polygalacturonic acid lyase, polygalacturonic acid lyase, pectin trans-eliminase, polygalacturonic acid trans-eliminase or (1→4)-α-D-galacturonan lyase.

An alpha rhamnosidase (EC 3.2.1.40) catalyzes the hydrolysis of terminal non-reducing α-L-rhamnose residues in α-L-rhamnosides or alternatively in rhamnogalacturonan. This enzyme may also be known as α-L-rhamnosidase T, α-L-rhamnosidase N or α-L-rhamnoside rhamnohydrolase.

An exo-galacturonase (EC 3.2.1.82) hydrolyzes pectic acid from the non-reducing end, releasing digalacturonate. The enzyme may also be known as exo-poly-α-galacturonosidase, exopolygalacturonosidase or exopolygalacturanosidase.

An exo-galacturonase (EC 3.2.1.67) catalyzes a reaction of the following type: (1,4-α-D-galacturonide)n+H2O=(1,4-α-D-galacturonide)n-i+D-galacturonate. The enzyme may also be known as galacturan 1,4-α-galacturonidase, exopolygalacturonase, poly(galacturonate) hydrolase, exo-D-galacturonase, exo-D-galacturonanase, exopoly-D-galacturonase or poly(1,4-α-D-galacturonide) galacturonohydrolase.

An exopolygalacturonate lyase (EC 4.2.2.9) catalyzes eliminative cleavage of 4-(4-deoxy-α-D-galact-4-enuronosyl)-D-galacturonate from the reducing end of pectate, i.e. de-esterified pectin. This enzyme may be known as pectate disaccharide-lyase, pectate exo-lyase, exopectic acid transeliminase, exopectate lyase, exopolygalacturonic acid-trans-eliminase, PATE, exo-PATE, exo-PGL or (1→4)-α-D-galacturonan reducing-end-disaccharide-lyase.

A rhamnogalacturonan hydrolyzes the linkage between galactosyluronic acid and rhamnopyranosyl in an endo-fashion in strictly alternating rhamnogalacturonan structures, consisting of the disaccharide [(1,2-alpha-L-rhamnoyl-(1,4)-alpha-galactosyluronic acid].

A rhamnogalacturonan lyase cleaves α-L-Rhap-(1→4)-α-D-GalpA linkages in an endo-fashion in rhamnogalacturonan by beta-elimination.

A rhamnogalacturonan acetyl esterase catalyzes the deacetylation of the backbone of alternating rhamnose and galacturonic acid residues in rhamnogalacturonan.

A rhamnogalacturonan galacturonohydrolase hydrolyzes galacturonic acid from the non-reducing end of strictly alternating rhamnogalacturonan structures in an exo-fashion. This enzyme may also be known as xylogalacturonan hydrolase.

An endo-arabinanase (EC 3.2.1.99) catalyzes endohydrolysis of 1,5-α-arabinofuranosidic linkages in 1,5-arabinans. The enzyme may also be known as endo-arabinase, arabinan endo-1,5-α-L-arabinosidase, endo-1,5-α-L-arabinanase, endo-α-1,5-arabanase; endo-arabanase or 1,5-α-L-arabinan 1,5-α-L-arabinanohydrolase.

One or more enzymes that participate in lignin degradation may also be included in an enzyme mixture that comprises a cellobiohydrolase variant of the invention. Enzymatic lignin depolymerization can be accomplished by lignin peroxidases, manganese peroxidases, laccases and cellobiose dehydrogenases (CDH), often working in synergy. These extracellular enzymes are often referred to as lignin-modifying enzymes or LMEs. Three of these enzymes comprise two glycosylated heme-containing peroxidases: lignin peroxidase (LIP); Mn-dependent peroxidase (MNP); and, a copper-containing phenoloxidase laccase (LCC).

Laccase: Laccases are copper containing oxidase enzymes that are found in many plants, fungi and microorganisms. Laccases are enzymatically active on phenols and similar molecules and perform a one electron oxidation. Laccases can be polymeric and the enzymatically active form can be a dimer or trimer.

Mn-dependent peroxidase: The enzymatic activity of Mn-dependent peroxidase (MnP) in is dependent on Mn2+. Without being bound by theory, it has been suggested that the main role of this enzyme is to oxidize Mn2+ to Mn3+ (Glenn et al. (1986) Arch. Biochem. Biophys. 251:688-696). Subsequently, phenolic substrates are oxidized by the Mn3+ generated.

Lignin peroxidase: Lignin peroxidase is an extracellular heme that catalyses the oxidative depolymerization of dilute solutions of polymeric lignin in vitro. Some of the substrates of LiP, most notably 3,4-dimethoxybenzyl alcohol (veratryl alcohol, VA), are active redox compounds that have been shown to act as redox mediators. VA is a secondary metabolite produced at the same time as LiP by ligninolytic cultures of *P. chrysosporium* and without being bound by a theory, has been proposed to function as a physiological redox mediator in the LiP-catalysed oxidation of lignin in vivo (Harvey, et al. (1986) FEBS Lett. 195, 242-246).

An enzymatic mixture comprising a cellobiohydrolase variant of the invention may further comprise at least one of the following: a protease or a lipase that participates in cellulose degradation.

"Protease" includes enzymes that hydrolyze peptide bonds (peptidases), as well as enzymes that hydrolyze bonds between peptides and other moieties, such as sugars (glycopeptidases). Many proteases are characterized under EC 3.4, and are suitable for use in the invention. Some specific types of proteases include, cysteine proteases including pepsin, papain and serine proteases including chymotrypsins, carboxypeptidases and metalloendopeptidases.

"Lipase" includes enzymes that hydrolyze lipids, fatty acids, and acylglycerides, including phospoglycerides, lipoproteins, diacylglycerols, and the like. In plants, lipids are used as structural components to limit water loss and pathogen infection. These lipids include waxes derived from fatty acids, as well as cutin and suberin.

An enzyme mixture that comprises a cellobiohydrolase variant of the invention may also comprise at least one expansin or expansin-like protein, such as a swollenin (see Salheimo et al., *Eur. J. Biohem.* 269, 4202-4211, 2002) or a swollenin-like protein.

Expansins are implicated in loosening of the cell wall structure during plant cell growth. Expansins have been proposed to disrupt hydrogen bonding between cellulose and other cell wall polysaccharides without having hydrolytic activity. In this way, they are thought to allow the sliding of cellulose fibers and enlargement of the cell wall. Swollenin, an expansin-like protein contains an N-terminal Carbohydrate Binding Module Family 1 domain (CBD) and a C-terminal expansin-like domain. For the purposes of this invention, an expansin-like protein or swollenin-like protein may comprise one or both of such domains and/or may disrupt the structure of cell walls (such as disrupting cellulose structure), optionally without producing detectable amounts of reducing sugars.

An enzyme mixture that comprises a cellobiohydrolase variant of the invention may also comprise at least one of the following: a polypeptide product of a cellulose integrating protein, scaffoldin or a scaffoldin-like protein, for example CipA or CipC from *Clostridium thermocellum* or *Clostridium cellulolyticum* respectively. Scaffoldins and cellulose integrating proteins are multi-functional integrating subunits which may organize cellulolytic subunits into a multi-enzyme complex. This is accomplished by the interaction of two complementary classes of domain, i.e. a cohesion domain on scaffoldin and a dockerin domain on each enzymatic unit. The scaffoldin subunit also bears a cellulose-binding module that mediates attachment of the cellulosome to its substrate. A scaffoldin or cellulose integrating protein for the purposes of this invention may comprise one or both of such domains.

An enzyme mixture that comprises a cellobiohydrolase variant of the invention may also comprise at least one cellulose induced protein or modulating protein, for example as encoded by cip1 or cip2 gene or similar genes from *Trichoderma reesei* (see Foreman et al., *J. Biol. Chem.* 278(34), 31988-31997, 2003).

An enzyme mixture that comprises a cellobiohydrolase variant of the invention may comprise a member of each of the classes of the polypeptides described above, several members of one polypeptide class, or any combination of these polypeptide classes.

Cellobiohydrolase Compositions

The cellobiohydrolase variants of the present invention, and biologically active fragments thereof, may be used in combination with other optional ingredients such as a buffer, a surfactant, and/or a scouring agent. A buffer may be used with a cellobiohydrolase of the present invention (optionally combined with other cellulases, including another cellobiohydrolase) to maintain a desired pH within the solution in which the cellobiohydrolase is employed. The exact concentration of buffer employed will depend on several factors which the skilled artisan can determine. Suitable buffers are well known in the art. A surfactant may further be used in combination with the cellobiohydrolases of the present invention. Suitable surfactants include any surfactant compatible with the cellobiohydrolase and, optionally, with any other cellulases being used. Exemplary surfactants include an anionic, a non-ionic, and ampholytic surfactants. Suitable anionic surfactants include, but are not limited to, linear or branched alkylbenzenesulfonates; alkyl or alkenyl ether sulfates having linear or branched alkyl groups or alkenyl groups; alkyl or alkenyl sulfates; olefinsulfonates; alkanesulfonates, etc. Suitable counter ions for anionic surfactants include, but are not limited to, alkali metal ions such as sodium and potassium; alkaline earth metal ions such as calcium and magnesium; ammonium ion; and alkanolamines having 1 to 3 alkanol groups of carbon number 2 or 3. Ampholytic surfactants include, e.g., quaternary ammonium salt sulfonates, and betaine-type ampholytic surfactants. Nonionic surfactants generally comprise polyoxyalkylene ethers, as well as higher fatty acid alkanolamides or alkylene oxide adduct thereof, and fatty acid glycerine monoesters. Mixtures of surfactants can also be employed as is known in the art.

The cellobiohydrolase variants of the invention may be used at effective amounts and concentrations and for effective lengths of time. An effective amount of cellobiohydrolase is a concentration of cellobiohydrolase sufficient for its intended purpose. For example, an effective amount of cellobiohydrolase within a solution may vary depending on whether the intended purpose is to use the enzyme composition comprising the cellobiohydrolase in a saccharification process, or for example a textile application such as stone-washing denim jeans. The amount of cellobiohydrolase employed is further dependent on the equipment employed, the process parameters employed, and the cellulase activity, e.g., a particular solution will require a lower concentration of cellobiohydrolase where a more active cellulase composition is used as compared to a less active cellulase composition. A concentration of cellobiohydrolase and length of time that an cellobiohydrolase will be in contact with the desired target further depends on the particular use employed by one of skill in the art, as is described herein.

One skilled in the art may practice the present invention using cellobiohydrolases in either aqueous solutions, or a solid cellobiohydrolase concentrate. When aqueous solutions are employed, the cellobiohydrolase solution can easily be diluted to allow accurate concentrations. A concentrate can be in any form recognized in the art including, but not limited to, liquids, emulsions, gel, pastes, granules, powders, an agglomerate, or a solid disk. Other materials can also be used with or placed in the cellulase composition of the present invention as desired, including stones, pumice, fillers, solvents, enzyme activators, and anti-redeposition agents depending on the intended use of the composition.

XI. Examples

The following examples are offered to illustrate, but not to limit the claimed invention.

Example 1

Wild-Type *M. thermophila* CBH2a Gene Acquisition and Construction of Expression Vectors The wild-type *M. thermophila* cellobiohydrolase type 2a (CBH2a) cDNA gene (SEQ ID NO:2) was cloned by PCR amplification from a cDNA library using vector-specific primers that flanked the inserts. The wild-type *M. thermophila* CBH2a sequence was cloned for expression in the *Saccharomyces cerevisiae* strain InvSc1, a commercially available strain (Invitrogen, Carlsbad, Calif.). A variant identified in the initial screening, Variant 22, was cloned for expression in the *Saccharomyces cerevisiae* strain InvSc1.

Example 2

Assays to Determine Cellobiohydrolase Thermostability

Cellobiohydrolase thermostability may be determined by exposing the cellobiohydrolase to stress conditions of elevated temperature, optionally at low pH, for an appropriate period of time and then determining residual cellobiohydrolase activity by a cellulose assay.

The cellobiohydrolase was challenged by incubating under conditions of pH 5 and 55° C. or 57° C. for 1 hour. Following the challenge incubation, residual activity of the cellobiohydrolase was measured.

Residual cellobiohydrolase activity was determined using a crystalline cellulose assay in which Avicel was used as a substrate. The reaction was incubated at 50° C., pH 5 for 16-24 hours in the presence of β-glucosidase. Activity was measured as glucose production using a GOPOD assay. 20 μl of the above reaction was mixed with 180 μl of GOPOD assay mix. The reactions were allowed to shake for at least 45 min at room temperature. Absorbance of the solution was measured at 510 nm to determine the amount of glucose produced in the original crystalline cellulose reaction.

Example 3

High Throughput Assays to Identify Improved *M. thermophila* CBH2a Variants

Variations were introduced into CBH2a cDNA sequences resulting in the generation of plasmid libraries containing variant cellobiohydrolase genes. The libraries were transformed into *S. cerevisiae*. Transformants were plated on SD-ura agar plate containing 2% glucose. After incubation for at least 48 hours at 30° C., colonies were picked using a Q-bot® robotic colony picker (Genetix USA, Inc., Beaverton, Oreg.) into shallow, 96-well microtiter plates containing pH adjusted 200 μL SD-ura media and 3% glucose. Cells were grown for 24 hours at 30° C. with shaking at 250 rpm and 85% humidity. 20 μL of this overnight culture was then transferred into 96-well microtiter plates (deep well) containing 380 μL DEMA Extra medium and 1% galactose. The plates were incubated at 37° C. with shaking at 250 rpm and 85% humidity for 48 hours. The deep plates were centrifuged at 4000 rpm for 15 minutes and the clear media supernatant containing the secreted cellobiohydrolase was used for the high throughput (HTP) Avicel assay.

The *M. thermophila* CBH2a libraries were screened in high throughput using a thermostability assay. In the thermostability assay, the HTP media supernatant samples containing *M. thermophila* cellobiohydrolase variant enzymes were pre-incubated at pH 5.0, temperature 55° C. for 1 hour for the first round or pH 5.0, temperature 57° C. for 1 hour for the second round. The residual enzyme activity with and without the thermal challenge was measured using a crystalline cellulose assay (pH 5.0; temperature 50° C.; time: 16-24 hrs) as described in Example 2.

The residual activity was calculated using the formula:

% residual activity=100×(Activity of challenged samples/Activity of unchallenged samples)

Residual activities of the *M. thermophila* CBH2a variants were compared to that of the wild-type *M. thermophila* CBH2a or of variant 22 to identify the thermostability improved variants.

Example 4

Improved Thermostability of Engineered *M. thermophila* CBH2a Variants—Round 1 Screen Improved *M. thermophila* CBH2a variants were identified from the high throughput screening of *M. thermophila* cellobiohydrolase variant libraries as described in Example 3. For the Round 1 screen (Table 3), the *M. thermophila* CBH2a of SEQ ID NO:1 was the reference protein.

Table 3 summarizes the results of the Round 1 screen, which identified improved *M. thermophila* cellobiohydrolase variants derived from the wild-type *M. thermophila* CBH2a (SEQ ID NO:1). The thermostability of the cellobiohydrolase variants were compared to the thermostability of the wild-type *M. thermophila* CBH2a of SEQ ID NO:1. Thermostability was assessed by determining residual enzyme activity on crystalline cellulose after incubation at pH 5.0 and 55° C. for 1 hour. Thermostability is presented as fold increase over wild-type *M. thermophila* CBH2a (SEQ ID NO:1). Amino acid positions (e.g., "F346") and changes (e.g., "F346Y") are relative to SEQ ID NO:1.

TABLE 3

Improved *M. thermophila* CBH2a variants

| Variant Number | Amino acid changes over wild-type *M. thermophila* CBH2a (SEQ ID NO: 1) | Thermostability: Fold improvement over wild-type *M. thermophila* CBH2a (SEQ ID NO: 1) |
|---|---|---|
| WT | — | — |
| 1 | V95L; S230A | +++ |
| 2 | F346Y | +++ |
| 3 | F346A | ++ |
| 4 | S160L | ++ |
| 5 | A109F | ++ |
| 6 | A204W | ++ |
| 7 | S160M | ++ |
| 8 | G329P | ++ |
| 9 | L200P | ++ |
| 10 | V95L | ++ |
| 11 | N39K | ++ |
| 12 | S160C | ++ |
| 13 | S230A | ++ |
| 14 | W199T | ++ |
| 15 | T361Q | ++ |
| 16 | S345P | ++ |

TABLE 3-continued

| Improved *M. thermophila* CBH2a variants | | |
|---|---|---|
| Variant Number | Amino acid changes over wild-type *M. thermophila* CBH2a (SEQ ID NO: 1) | Thermostability: Fold improvement over wild-type *M. thermophila* CBH2a (SEQ ID NO: 1) |
| 17 | N39R | ++ |
| 18 | F346K | ++ |
| 19 | N265H | ++ |
| 20 | F346S | ++ |
| 21 | D122S | ++ |
| 22 | S250P | ++ |
| 23 | N39C | ++ |
| 24 | T361K | + |
| 25 | G297M | + |
| 26 | N39A | + |
| 27 | N39V | + |
| 28 | N39P | + |
| 29 | W199M | + |
| 30 | S55P | + |
| 31 | A340S | + |
| 32 | F346N | + |
| 33 | T361E | + |
| 34 | A109M | + |
| 35 | N113R | + |
| 36 | S273A | + |
| 37 | T266L | + |
| 38 | Q31C | + |
| 39 | R11V | + |
| 40 | R11N | + |
| 41 | R11T | + |
| 42 | A13P | + |
| 43 | R11I | + |

+ indicates a 1.1- to 1.4-fold improvement over wild-type C1 CBH2a
++ indicates a 1.5- to 2.0-fold improvement over wild-type C1 CBH2a
+++ indicates a greater than 2.0-fold improvement over wild-type C1 CBH2a

Example 5

Improved Thermostability of Engineered *M. thermophila* CBH2a Variants—Round 2 Screen From the Round 1 screen, one of the improved variants from the round (variant 22, as shown in Table 4) was selected as the reference protein for the Round 2 screen. Libraries were designed to combine beneficial mutations identified in the Round 1 screen. The resulting CBH2a polypeptides were expressed in yeast and tested for thermostability and pH tolerance. Table 4 summarizes the results of the Round 2 screen. The thermostability of the cellobiohydrolase variants were compared to the thermostability of variant 22. Thermostability was assessed by determining residual enzyme activity on crystalline cellulose after incubation at pH 5.0 and 57° C. for 1 hour. Thermostability is presented as fold increase over Variant 22. Amino acid positions (e.g., "A15") and changes (e.g., "A15I") are relative to SEQ ID NO:1.

TABLE 4

| Improved C1 CBH2a variants | | |
|---|---|---|
| Variant Number | Amino acid changes over wild-type *M. thermophila* CBH2a (SEQ ID NO: 1) | Thermostability: Fold improvement over Variant 22 |
| 22 | S250P | — |
| 44 | A15I; N39C; N113R; A204W; S250V; S273D; A340S | ++ |
| 45 | A15S; N39A; K110Q; A204W; S250P; A340S | ++ |
| 46 | A15I; N39A; N113L; A204W; T266L; S345E | ++ |
| 47 | A15I; S55P; A204W; Q211K; N265H; A340S | ++ |
| 48 | A15S; A204W; A340S | + |
| 49 | A15F; N39K; T75S; A204Q; T266L | + |
| 50 | A15S; A204W; S345E | + |
| 51 | A15I; R81K; A204W; T266L; A340S | + |
| 52 | A15S; T69C; N113T; N159H; A204W; T266L; A340S | + |
| 53 | S14L; T69C; N265H; A340S | + |
| 54 | A15S; N39A; K110E; A204W; S250C; K272A; S345P | + |
| 55 | A15I; A204W; S250V; A340S | + |

+ indicates a 1.1- to 1.4-fold improvement over Variant 22
++ indicates a greater than 1.4-fold improvement over Variant 22

Example 6

Performance Sensitive Positions Identified in *M. thermophila* CBH2a and CBH2b To determine whether beneficial mutations at particular cellobiohydrolase residues impart improved stability across corresponding amino acid residues of homologous cellobiohydrolases, site-saturation mutagenesis was performed on both *M. thermophila* CBH2a and *M. thermophila* CBH2b. The wild-type *M. thermophila* CBH2a and CBH2b cDNA genes were expressed in *S. cerevisiae* as described in Example 1. Site-saturation libraries were constructed for each gene and HTP screens were performed according to the methods described in Example 3. Sequence analysis of the improved variants identified for CBH2a and CBH2b showed that there were multiple positions for which amino acid substitutions from the wild-type residue resulted in improvements in stability (as measured according to the methods of Examples 2 and 3) for corresponding positions in *M. thermophila* CBH2a and CBH2b (Table 5). Corresponding positions were identified by aligning CBH2a and CBH2b using the protein alignment tool AlignX as shown in FIG. 1.

TABLE 5

| Amino acid positions with mutations common to CBH2a and CBH2b that improve protein stability | |
|---|---|
| CBH2a substitution | CBH2b substitution |
| Q31C | S111N |
| N39ACKPRV | D119PR |
| S160CLM | M250G |
| W199MT | W289CMS |
| A204QW | A294R |
| S250CPV | S336HKNPT |
| S273AD | S359DK |
| G297M | G384T |
| S345EP | Y432W |
| T361EKQ | Q448K |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A recombinant polynucleotide that comprises a nucleic acid sequence encoding a cellobiohydrolase type 2a (CBH2a) variant comprising at least about 90% sequence identity to SEQ ID NO:1 and comprising an amino acid substitution, relative to SEQ ID NO:1, at one or more positions selected from 15, 204, and 340, wherein the position is numbered with reference to SEQ ID NO:1.

2. The recombinant polynucleotide of claim 1, wherein the amino acid residue at position 15 of the CBH2a variant is phenylalanine, isoleucine, or serine (X15F/I/S); the amino acid residue at position 204 of the CBH2a variant is tryptophan (X204W); and/or the amino acid residue at position 340 of the CBH2a variant is serine (X340S).

3. The recombinant polynucleotide of claim 1, wherein the CBH2a variant further comprises an amino acid substitution, relative to SEQ ID NO:1, at one or more positions selected from 39, 113, and 250.

4. The recombinant polynucleotide of claim 3, wherein the amino acid residue at position 39 of the CBH2a variant is alanine or cysteine (X39A/C); the amino acid residue at position 113 of the CBH2a variant is leucine or arginine (X113L/R); and/or the amino acid residue at position 250 of the CBH2a variant is proline or valine (X250P/V).

5. The recombinant polynucleotide of claim 1, wherein the CBH2a variant is a *Myceliophthora thermophila* cellobiohydrolase.

6. The recombinant polynucleotide of claim 1, wherein the CBH2a variant comprises at least 95% sequence identity to SEQ ID NO:1.

7. The recombinant polynucleotide of claim 1, wherein the CBH2a variant has increased thermostability after incubation at pH 5.0 and 55° C. for 1 hour in comparison to wild-type *Myceliophthora thermophila* CBH2a (SEQ ID NO:1).

8. An expression vector comprising the recombinant polynucleotide of claim 1.

9. A host cell comprising a recombinant polynucleotide of claim 1.

10. The host cell of claim 9, wherein the host cell is a yeast or a filamentous fungus.

11. A recombinant polynucleotide that comprises a nucleic acid sequence that encodes a cellobiohydrolase type 2 (CBH2) variant comprising at least 90% sequence identity to SEQ ID NO:1 and comprising an amino acid substitution selected from:

a glutamine, arginine, or tryptophan residue at position 204 (X204Q/R/W);

wherein the position is numbered with reference to SEQ ID NO:1, and wherein the cellobiohydrolase variant has increased thermostability in comparison to the wild-type cellobiohydrolase from which the variant is derived.

12. The recombinant polynucleotide of claim 11, wherein the CBH2 variant further comprises one or more amino acid substitutions selected from:

an alanine, cysteine, lysine, proline, arginine, or valine residue at position 39 (X39A/C/K/P/R/V); and a cysteine, histidine, lysine, asparagine, proline, threonine, or valine at position 250 (X250C/H/K/N/P/TN).

13. The recombinant polynucleotide of claim 11, wherein the CBH2 variant further comprises an amino acid substitution at one or more positions selected from 15, 39, 113, 250, and 340, wherein the position is numbered with reference to SEQ ID NO:1.

14. The recombinant polynucleotide of claim 13, wherein:

the amino acid substitution at position 15 is phenylalanine, isoleucine, or serine (X15F/I/S);

the amino acid substitution at position 39 is alanine or cysteine (X39A/C/K/P/R/V);

the amino acid substitution at position 113 is leucine or arginine (X113L/R/T);

the amino acid substitution at position 250 is proline or valine (X250P/V); and/or the amino acid residue at position 340 is serine (X340S).

15. An expression vector comprising the recombinant polynucleotide of claim 11.

16. A host cell comprising a recombinant polynucleotide of claim 11.

17. The host cell of claim 16, wherein the host cell is a yeast or a filamentous fungus.

* * * * *

SEQUENCE LISTING

<160> NUMBER OF SEQ ID NOS: 26

<210> SEQ ID NO 1
<211> LENGTH: 378
<212> TYPE: PRT
<213> ORGANISM: Myceliophthora thermophila

<400> SEQUENCE: 1

Ala Pro Ser Arg Thr Thr Pro Gln Lys Pro Arg Gln Ala Ser Ala Gly
1 5 10 15

Cys Ala Ser Ala Val Thr Leu Asp Ala Ser Thr Asn Val Phe Gln Gln
20 25 30

Tyr Thr Leu His Pro Asn Asn Phe Tyr Arg Ala Glu Val Glu Ala Ala
35 40 45

Ala Glu Ala Ile Ser Asp Ser Ala Leu Ala Glu Lys Ala Arg Lys Val
50 55 60

Ala Asp Val Gly Thr Phe Leu Trp Leu Asp Thr Ile Glu Asn Ile Gly
65 70 75 80

Arg Leu Glu Pro Ala Leu Glu Asp Val Pro Cys Glu Asn Ile Val Gly
85 90 95

Leu Val Ile Tyr Asp Leu Pro Gly Arg Asp Cys Ala Ala Lys Ala Ser
100 105 110

Asn Gly Glu Leu Lys Val Gly Glu Leu Asp Arg Tyr Lys Thr Glu Tyr
115 120 125

Ile Asp Lys Ile Ala Glu Ile Leu Lys Ala His Ser Asn Thr Ala Phe
130 135 140

Ala Leu Val Ile Glu Pro Asp Ser Leu Pro Asn Leu Val Thr Asn Ser
145 150 155 160

Asp Leu Gln Thr Cys Gln Gln Ser Ala Ser Gly Tyr Arg Glu Gly Val
165 170 175

Ala Tyr Ala Leu Lys Gln Leu Asn Leu Pro Asn Val Val Met Tyr Ile
180 185 190

Asp Ala Gly His Gly Gly Trp Leu Gly Trp Asp Ala Asn Leu Lys Pro
195 200 205

Gly Ala Gln Glu Leu Ala Ser Val Tyr Lys Ser Ala Gly Ser Pro Ser
210 215 220

Gln Val Arg Gly Ile Ser Thr Asn Val Ala Gly Trp Asn Ala Trp Asp
225 230 235 240

Gln Glu Pro Gly Glu Phe Ser Asp Ala Ser Asp Ala Gln Tyr Asn Lys
245 250 255

Cys Gln Asn Glu Lys Ile Tyr Ile Asn Thr Phe Gly Ala Glu Leu Lys
260 265 270

Ser Ala Gly Met Pro Asn His Ala Ile Ile Asp Thr Gly Arg Asn Gly
275 280 285

Val Thr Gly Leu Arg Asp Glu Trp Gly Asp Trp Cys Asn Val Asn Gly
290 295 300

Ala Gly Phe Gly Val Arg Pro Thr Ala Asn Thr Gly Asp Glu Leu Ala
305 310 315 320

Asp Ala Phe Val Trp Val Lys Pro Gly Gly Glu Ser Asp Gly Thr Ser
325 330 335

Asp Ser Ser Ala Ala Arg Tyr Asp Ser Phe Cys Gly Lys Pro Asp Ala
340 345 350

Phe Lys Pro Ser Pro Glu Ala Gly Thr Trp Asn Gln Ala Tyr Phe Glu
355 360 365

-continued

```
Met Leu Leu Lys Asn Ala Asn Pro Ser Phe
    370                 375


<210> SEQ ID NO 2
<211> LENGTH: 1134
<212> TYPE: DNA
<213> ORGANISM: Myceliophthora thermophila

<400> SEQUENCE: 2

gcgccctcgc gcacgactcc ccagaagccc cgccaggcct cggcgggctg cgcgtcggcc     60

gtgacgctcg atgccagcac caacgtgttc cagcagtaca cgctgcaccc caacaacttc    120

taccgtgccg aggtcgaggc tgccgccgag gccatctccg actcggcgct ggccgagaag    180

gcccgcaagg tcgccgacgt cggtaccttc ctgtggctcg acaccatcga gaacattggc    240

cggctggagc ccgcgctcga ggacgtgccc tgcgagaaca tcgtgggtct cgtcatctac    300

gacctcccgg gccgtgactg cgcggccaag gcctccaacg gcgagctcaa ggtcggcgag    360

ctcgacaggt acaagaccga gtacatcgac aagatcgccg agatcctcaa ggcccactcc    420

aacacggcct tcgccctcgt catcgagccc gactcgctcc ccaacctggt caccaatagc    480

gacctgcaga cgtgccagca gagcgcttcc ggctaccgcg agggtgtcgc ctatgccctc    540

aagcagctca acctccccaa cgtggtcatg tacatcgatg ccggccacgg tggctggctc    600

ggctgggacg ccaacctcaa gcccggcgcc caggagctcg ccagcgtcta caagtctgct    660

ggttcgccct cgcaagtccg cggtatctcc accaacgtgg ctggttggaa cgcctgggac    720

caggagcccg gtgagttctc ggacgcctcg gatgcccagt acaacaagtg ccagaacgag    780

aagatctaca tcaacacctt tggcgctgag ctcaagtctg ccggcatgcc caaccacgcc    840

atcatcgaca ctggccgcaa cggtgtcacc ggtctccgcg acgagtgggg tgactggtgc    900

aacgtcaacg gcgccggctt cggtgtgcgc ccgactgcca acactggcga cgagctcgcc    960

gacgccttcg tgtgggtcaa gcccggtggc gagtccgacg gcaccagcga ctcgtcggcg   1020

gcgcgctacg acagcttctg cggcaagccc gacgccttca agcccagccc cgaggccggt   1080

acctggaacc aggcctactt cgagatgctc ctcaagaacg ccaacccgtc cttc         1134


<210> SEQ ID NO 3
<211> LENGTH: 378
<212> TYPE: PRT
<213> ORGANISM: Artificial sequence
<220> FEATURE:
<223> OTHER INFORMATION: Synthetic polypeptide for M. thermophila CBH2a
      variant 1

<400> SEQUENCE: 3

Ala Pro Ser Arg Thr Thr Pro Gln Lys Pro Arg Gln Ala Ser Ala Gly
1               5                   10                  15

Cys Ala Ser Ala Val Thr Leu Asp Ala Ser Thr Asn Val Phe Gln Gln
            20                  25                  30

Tyr Thr Leu His Pro Asn Asn Phe Tyr Arg Ala Glu Val Glu Ala Ala
        35                  40                  45

Ala Glu Ala Ile Ser Asp Ser Ala Leu Ala Glu Lys Ala Arg Lys Val
    50                  55                  60

Ala Asp Val Gly Thr Phe Leu Trp Leu Asp Thr Ile Glu Asn Ile Gly
65                  70                  75                  80

Arg Leu Glu Pro Ala Leu Glu Asp Val Pro Cys Glu Asn Ile Leu Gly
                85                  90                  95

Leu Val Ile Tyr Asp Leu Pro Gly Arg Asp Cys Ala Ala Lys Ala Ser
```

-continued

```
            100                 105                 110

Asn Gly Glu Leu Lys Val Gly Glu Leu Asp Arg Tyr Lys Thr Glu Tyr
        115                 120                 125

Ile Asp Lys Ile Ala Glu Ile Leu Lys Ala His Ser Asn Thr Ala Phe
    130                 135                 140

Ala Leu Val Ile Glu Pro Asp Ser Leu Pro Asn Leu Val Thr Asn Ser
145                 150                 155                 160

Asp Leu Gln Thr Cys Gln Gln Ser Ala Ser Gly Tyr Arg Glu Gly Val
                165                 170                 175

Ala Tyr Ala Leu Lys Gln Leu Asn Leu Pro Asn Val Val Met Tyr Ile
            180                 185                 190

Asp Ala Gly His Gly Gly Trp Leu Gly Trp Asp Ala Asn Leu Lys Pro
        195                 200                 205

Gly Ala Gln Glu Leu Ala Ser Val Tyr Lys Ser Ala Gly Ser Pro Ser
    210                 215                 220

Gln Val Arg Gly Ile Ala Thr Asn Val Ala Gly Trp Asn Ala Trp Asp
225                 230                 235                 240

Gln Glu Pro Gly Glu Phe Ser Asp Ala Ser Asp Ala Gln Tyr Asn Lys
                245                 250                 255

Cys Gln Asn Glu Lys Ile Tyr Ile Asn Thr Phe Gly Ala Glu Leu Lys
            260                 265                 270

Ser Ala Gly Met Pro Asn His Ala Ile Ile Asp Thr Gly Arg Asn Gly
        275                 280                 285

Val Thr Gly Leu Arg Asp Glu Trp Gly Asp Trp Cys Asn Val Asn Gly
    290                 295                 300

Ala Gly Phe Gly Val Arg Pro Thr Ala Asn Thr Gly Asp Glu Leu Ala
305                 310                 315                 320

Asp Ala Phe Val Trp Val Lys Pro Gly Gly Glu Ser Asp Gly Thr Ser
                325                 330                 335

Asp Ser Ser Ala Ala Arg Tyr Asp Ser Phe Cys Gly Lys Pro Asp Ala
            340                 345                 350

Phe Lys Pro Ser Pro Glu Ala Gly Thr Trp Asn Gln Ala Tyr Phe Glu
        355                 360                 365

Met Leu Leu Lys Asn Ala Asn Pro Ser Phe
    370                 375


<210> SEQ ID NO 4
<211> LENGTH: 378
<212> TYPE: PRT
<213> ORGANISM: Artificial sequence
<220> FEATURE:
<223> OTHER INFORMATION: Synthetic polypeptide for M. thermophila
      CBH2a variant 2

<400> SEQUENCE: 4

Ala Pro Ser Arg Thr Thr Pro Gln Lys Pro Arg Gln Ala Ser Ala Gly
1               5                   10                  15

Cys Ala Ser Ala Val Thr Leu Asp Ala Ser Thr Asn Val Phe Gln Gln
            20                  25                  30

Tyr Thr Leu His Pro Asn Asn Phe Tyr Arg Ala Glu Val Glu Ala Ala
        35                  40                  45

Ala Glu Ala Ile Ser Asp Ser Ala Leu Ala Glu Lys Ala Arg Lys Val
    50                  55                  60

Ala Asp Val Gly Thr Phe Leu Trp Leu Asp Thr Ile Glu Asn Ile Gly
65                  70                  75                  80
```

-continued

```
Arg Leu Glu Pro Ala Leu Glu Asp Val Pro Cys Glu Asn Ile Val Gly
                85                  90                  95

Leu Val Ile Tyr Asp Leu Pro Gly Arg Asp Cys Ala Ala Lys Ala Ser
            100                 105                 110

Asn Gly Glu Leu Lys Val Gly Glu Leu Asp Arg Tyr Lys Thr Glu Tyr
        115                 120                 125

Ile Asp Lys Ile Ala Glu Ile Leu Lys Ala His Ser Asn Thr Ala Phe
    130                 135                 140

Ala Leu Val Ile Glu Pro Asp Ser Leu Pro Asn Leu Val Thr Asn Ser
145                 150                 155                 160

Asp Leu Gln Thr Cys Gln Gln Ser Ala Ser Gly Tyr Arg Glu Gly Val
                165                 170                 175

Ala Tyr Ala Leu Lys Gln Leu Asn Leu Pro Asn Val Val Met Tyr Ile
            180                 185                 190

Asp Ala Gly His Gly Gly Trp Leu Gly Trp Asp Ala Asn Leu Lys Pro
        195                 200                 205

Gly Ala Gln Glu Leu Ala Ser Val Tyr Lys Ser Ala Gly Ser Pro Ser
    210                 215                 220

Gln Val Arg Gly Ile Ser Thr Asn Val Ala Gly Trp Asn Ala Trp Asp
225                 230                 235                 240

Gln Glu Pro Gly Glu Phe Ser Asp Ala Ser Asp Ala Gln Tyr Asn Lys
                245                 250                 255

Cys Gln Asn Glu Lys Ile Tyr Ile Asn Thr Phe Gly Ala Glu Leu Lys
            260                 265                 270

Ser Ala Gly Met Pro Asn His Ala Ile Ile Asp Thr Gly Arg Asn Gly
        275                 280                 285

Val Thr Gly Leu Arg Asp Glu Trp Gly Asp Trp Cys Asn Val Asn Gly
    290                 295                 300

Ala Gly Phe Gly Val Arg Pro Thr Ala Asn Thr Gly Asp Glu Leu Ala
305                 310                 315                 320

Asp Ala Phe Val Trp Val Lys Pro Gly Gly Glu Ser Asp Gly Thr Ser
                325                 330                 335

Asp Ser Ser Ala Ala Arg Tyr Asp Ser Tyr Cys Gly Lys Pro Asp Ala
            340                 345                 350

Phe Lys Pro Ser Pro Glu Ala Gly Thr Trp Asn Gln Ala Tyr Phe Glu
        355                 360                 365

Met Leu Leu Lys Asn Ala Asn Pro Ser Phe
    370                 375


<210> SEQ ID NO 5
<211> LENGTH: 378
<212> TYPE: PRT
<213> ORGANISM: Artificial sequence
<220> FEATURE:
<223> OTHER INFORMATION: Synthetic polypeptide for M. thermophila CBH2a
      variant 22

<400> SEQUENCE: 5

Ala Pro Ser Arg Thr Thr Pro Gln Lys Pro Arg Gln Ala Ser Ala Gly
1               5                   10                  15

Cys Ala Ser Ala Val Thr Leu Asp Ala Ser Thr Asn Val Phe Gln Gln
            20                  25                  30

Tyr Thr Leu His Pro Asn Asn Phe Tyr Arg Ala Glu Val Glu Ala Ala
        35                  40                  45

Ala Glu Ala Ile Ser Asp Ser Ala Leu Ala Glu Lys Ala Arg Lys Val
    50                  55                  60
```

-continued

```
Ala Asp Val Gly Thr Phe Leu Trp Leu Asp Thr Ile Glu Asn Ile Gly
65                  70                  75                  80

Arg Leu Glu Pro Ala Leu Glu Asp Val Pro Cys Glu Asn Ile Val Gly
                85                  90                  95

Leu Val Ile Tyr Asp Leu Pro Gly Arg Asp Cys Ala Ala Lys Ala Ser
            100                 105                 110

Asn Gly Glu Leu Lys Val Gly Glu Leu Asp Arg Tyr Lys Thr Glu Tyr
        115                 120                 125

Ile Asp Lys Ile Ala Glu Ile Leu Lys Ala His Ser Asn Thr Ala Phe
    130                 135                 140

Ala Leu Val Ile Glu Pro Asp Ser Leu Pro Asn Leu Val Thr Asn Ser
145                 150                 155                 160

Asp Leu Gln Thr Cys Gln Gln Ser Ala Ser Gly Tyr Arg Glu Gly Val
                165                 170                 175

Ala Tyr Ala Leu Lys Gln Leu Asn Leu Pro Asn Val Val Met Tyr Ile
            180                 185                 190

Asp Ala Gly His Gly Gly Trp Leu Gly Trp Asp Ala Asn Leu Lys Pro
        195                 200                 205

Gly Ala Gln Glu Leu Ala Ser Val Tyr Lys Ser Ala Gly Ser Pro Ser
    210                 215                 220

Gln Val Arg Gly Ile Ser Thr Asn Val Ala Gly Trp Asn Ala Trp Asp
225                 230                 235                 240

Gln Glu Pro Gly Glu Phe Ser Asp Ala Pro Asp Ala Gln Tyr Asn Lys
                245                 250                 255

Cys Gln Asn Glu Lys Ile Tyr Ile Asn Thr Phe Gly Ala Glu Leu Lys
            260                 265                 270

Ser Ala Gly Met Pro Asn His Ala Ile Ile Asp Thr Gly Arg Asn Gly
        275                 280                 285

Val Thr Gly Leu Arg Asp Glu Trp Gly Asp Trp Cys Asn Val Asn Gly
    290                 295                 300

Ala Gly Phe Gly Val Arg Pro Thr Ala Asn Thr Gly Asp Glu Leu Ala
305                 310                 315                 320

Asp Ala Phe Val Trp Val Lys Pro Gly Gly Glu Ser Asp Gly Thr Ser
                325                 330                 335

Asp Ser Ser Ala Ala Arg Tyr Asp Ser Phe Cys Gly Lys Pro Asp Ala
            340                 345                 350

Phe Lys Pro Ser Pro Glu Ala Gly Thr Trp Asn Gln Ala Tyr Phe Glu
        355                 360                 365

Met Leu Leu Lys Asn Ala Asn Pro Ser Phe
    370                 375


<210> SEQ ID NO 6
<211> LENGTH: 378
<212> TYPE: PRT
<213> ORGANISM: Artificial sequence
<220> FEATURE:
<223> OTHER INFORMATION: Synthetic polypeptide for M. thermophila CBH2a
      variant 44

<400> SEQUENCE: 6

Ala Pro Ser Arg Thr Thr Pro Gln Lys Pro Arg Gln Ala Ser Ile Gly
1               5                   10                  15

Cys Ala Ser Ala Val Thr Leu Asp Ala Ser Thr Asn Val Phe Gln Gln
            20                  25                  30

Tyr Thr Leu His Pro Asn Cys Phe Tyr Arg Ala Glu Val Glu Ala Ala
```

```
        35                  40                  45

Ala Glu Ala Ile Ser Asp Ser Ala Leu Ala Glu Lys Ala Arg Lys Val
    50                  55                  60

Ala Asp Val Gly Thr Phe Leu Trp Leu Asp Thr Ile Glu Asn Ile Gly
65                  70                  75                  80

Arg Leu Glu Pro Ala Leu Glu Asp Val Pro Cys Glu Asn Ile Val Gly
                85                  90                  95

Leu Val Ile Tyr Asp Leu Pro Gly Arg Asp Cys Ala Ala Lys Ala Ser
            100                 105                 110

Arg Gly Glu Leu Lys Val Gly Glu Leu Asp Arg Tyr Lys Thr Glu Tyr
        115                 120                 125

Ile Asp Lys Ile Ala Glu Ile Leu Lys Ala His Ser Asn Thr Ala Phe
    130                 135                 140

Ala Leu Val Ile Glu Pro Asp Ser Leu Pro Asn Leu Val Thr Asn Ser
145                 150                 155                 160

Asp Leu Gln Thr Cys Gln Gln Ser Ala Ser Gly Tyr Arg Glu Gly Val
                165                 170                 175

Ala Tyr Ala Leu Lys Gln Leu Asn Leu Pro Asn Val Val Met Tyr Ile
            180                 185                 190

Asp Ala Gly His Gly Gly Trp Leu Gly Trp Asp Trp Asn Leu Lys Pro
        195                 200                 205

Gly Ala Gln Glu Leu Ala Ser Val Tyr Lys Ser Ala Gly Ser Pro Ser
    210                 215                 220

Gln Val Arg Gly Ile Ser Thr Asn Val Ala Gly Trp Asn Ala Trp Asp
225                 230                 235                 240

Gln Glu Pro Gly Glu Phe Ser Asp Ala Val Asp Ala Gln Tyr Asn Lys
                245                 250                 255

Cys Gln Asn Glu Lys Ile Tyr Ile Asn Thr Phe Gly Ala Glu Leu Lys
            260                 265                 270

Asp Ala Gly Met Pro Asn His Ala Ile Ile Asp Thr Gly Arg Asn Gly
        275                 280                 285

Val Thr Gly Leu Arg Asp Glu Trp Gly Asp Trp Cys Asn Val Asn Gly
    290                 295                 300

Ala Gly Phe Gly Val Arg Pro Thr Ala Asn Thr Gly Asp Glu Leu Ala
305                 310                 315                 320

Asp Ala Phe Val Trp Val Lys Pro Gly Gly Glu Ser Asp Gly Thr Ser
                325                 330                 335

Asp Ser Ser Ser Ala Arg Tyr Asp Ser Phe Cys Gly Lys Pro Asp Ala
            340                 345                 350

Phe Lys Pro Ser Pro Glu Ala Gly Thr Trp Asn Gln Ala Tyr Phe Glu
        355                 360                 365

Met Leu Leu Lys Asn Ala Asn Pro Ser Phe
    370                 375


<210> SEQ ID NO 7
<211> LENGTH: 378
<212> TYPE: PRT
<213> ORGANISM: Artificial sequence
<220> FEATURE:
<223> OTHER INFORMATION: Synthetic polypeptide for M. thermophila CBH2a
      variant 45

<400> SEQUENCE: 7

Ala Pro Ser Arg Thr Thr Pro Gln Lys Pro Arg Gln Ala Ser Ser Gly
1               5                   10                  15
```

-continued

```
Cys Ala Ser Ala Val Thr Leu Asp Ala Ser Thr Asn Val Phe Gln Gln
            20                  25                  30

Tyr Thr Leu His Pro Asn Ala Phe Tyr Arg Ala Glu Val Glu Ala Ala
        35                  40                  45

Ala Glu Ala Ile Ser Asp Ser Ala Leu Ala Glu Lys Ala Arg Lys Val
    50                  55                  60

Ala Asp Val Gly Thr Phe Leu Trp Leu Asp Thr Ile Glu Asn Ile Gly
65                  70                  75                  80

Arg Leu Glu Pro Ala Leu Glu Asp Val Pro Cys Glu Asn Ile Val Gly
                85                  90                  95

Leu Val Ile Tyr Asp Leu Pro Gly Arg Asp Cys Ala Ala Gln Ala Ser
            100                 105                 110

Asn Gly Glu Leu Lys Val Gly Glu Leu Asp Arg Tyr Lys Thr Glu Tyr
        115                 120                 125

Ile Asp Lys Ile Ala Glu Ile Leu Lys Ala His Ser Asn Thr Ala Phe
    130                 135                 140

Ala Leu Val Ile Glu Pro Asp Ser Leu Pro Asn Leu Val Thr Asn Ser
145                 150                 155                 160

Asp Leu Gln Thr Cys Gln Gln Ser Ala Ser Gly Tyr Arg Glu Gly Val
                165                 170                 175

Ala Tyr Ala Leu Lys Gln Leu Asn Leu Pro Asn Val Val Met Tyr Ile
            180                 185                 190

Asp Ala Gly His Gly Gly Trp Leu Gly Trp Asp Trp Asn Leu Lys Pro
        195                 200                 205

Gly Ala Gln Glu Leu Ala Ser Val Tyr Lys Ser Ala Gly Ser Pro Ser
    210                 215                 220

Gln Val Arg Gly Ile Ser Thr Asn Val Ala Gly Trp Asn Ala Trp Asp
225                 230                 235                 240

Gln Glu Pro Gly Glu Phe Ser Asp Ala Pro Asp Ala Gln Tyr Asn Lys
                245                 250                 255

Cys Gln Asn Glu Lys Ile Tyr Ile Asn Thr Phe Gly Ala Glu Leu Lys
            260                 265                 270

Ser Ala Gly Met Pro Asn His Ala Ile Ile Asp Thr Gly Arg Asn Gly
        275                 280                 285

Val Thr Gly Leu Arg Asp Glu Trp Gly Asp Trp Cys Asn Val Asn Gly
    290                 295                 300

Ala Gly Phe Gly Val Arg Pro Thr Ala Asn Thr Gly Asp Glu Leu Ala
305                 310                 315                 320

Asp Ala Phe Val Trp Val Lys Pro Gly Gly Glu Ser Asp Gly Thr Ser
                325                 330                 335

Asp Ser Ser Ser Ala Arg Tyr Asp Ser Phe Cys Gly Lys Pro Asp Ala
            340                 345                 350

Phe Lys Pro Ser Pro Glu Ala Gly Thr Trp Asn Gln Ala Tyr Phe Glu
        355                 360                 365

Met Leu Leu Lys Asn Ala Asn Pro Ser Phe
    370                 375
```

```
<210> SEQ ID NO 8
<211> LENGTH: 378
<212> TYPE: PRT
<213> ORGANISM: Artificial sequence
<220> FEATURE:
<223> OTHER INFORMATION: Synthetic polypeptide for M. thermophila CBH2a
      variant 46

<400> SEQUENCE: 8
```

-continued

```
Ala Pro Ser Arg Thr Thr Pro Gln Lys Pro Arg Gln Ala Ser Ile Gly
1               5                   10                  15

Cys Ala Ser Ala Val Thr Leu Asp Ala Ser Thr Asn Val Phe Gln Gln
            20                  25                  30

Tyr Thr Leu His Pro Asn Ala Phe Tyr Arg Ala Glu Val Glu Ala Ala
        35                  40                  45

Ala Glu Ala Ile Ser Asp Ser Ala Leu Ala Glu Lys Ala Arg Lys Val
    50                  55                  60

Ala Asp Val Gly Thr Phe Leu Trp Leu Asp Thr Ile Glu Asn Ile Gly
65                  70                  75                  80

Arg Leu Glu Pro Ala Leu Glu Asp Val Pro Cys Glu Asn Ile Val Gly
                85                  90                  95

Leu Val Ile Tyr Asp Leu Pro Gly Arg Asp Cys Ala Ala Lys Ala Ser
            100                 105                 110

Leu Gly Glu Leu Lys Val Gly Glu Leu Asp Arg Tyr Lys Thr Glu Tyr
        115                 120                 125

Ile Asp Lys Ile Ala Glu Ile Leu Lys Ala His Ser Asn Thr Ala Phe
    130                 135                 140

Ala Leu Val Ile Glu Pro Asp Ser Leu Pro Asn Leu Val Thr Asn Ser
145                 150                 155                 160

Asp Leu Gln Thr Cys Gln Gln Ser Ala Ser Gly Tyr Arg Glu Gly Val
                165                 170                 175

Ala Tyr Ala Leu Lys Gln Leu Asn Leu Pro Asn Val Val Met Tyr Ile
            180                 185                 190

Asp Ala Gly His Gly Gly Trp Leu Gly Trp Asp Trp Asn Leu Lys Pro
        195                 200                 205

Gly Ala Gln Glu Leu Ala Ser Val Tyr Lys Ser Ala Gly Ser Pro Ser
    210                 215                 220

Gln Val Arg Gly Ile Ser Thr Asn Val Ala Gly Trp Asn Ala Trp Asp
225                 230                 235                 240

Gln Glu Pro Gly Glu Phe Ser Asp Ala Ser Asp Ala Gln Tyr Asn Lys
                245                 250                 255

Cys Gln Asn Glu Lys Ile Tyr Ile Asn Leu Phe Gly Ala Glu Leu Lys
            260                 265                 270

Ser Ala Gly Met Pro Asn His Ala Ile Ile Asp Thr Gly Arg Asn Gly
        275                 280                 285

Val Thr Gly Leu Arg Asp Glu Trp Gly Asp Trp Cys Asn Val Asn Gly
    290                 295                 300

Ala Gly Phe Gly Val Arg Pro Thr Ala Asn Thr Gly Asp Glu Leu Ala
305                 310                 315                 320

Asp Ala Phe Val Trp Val Lys Pro Gly Gly Glu Ser Asp Gly Thr Ser
                325                 330                 335

Asp Ser Ser Ala Ala Arg Tyr Asp Glu Phe Cys Gly Lys Pro Asp Ala
            340                 345                 350

Phe Lys Pro Ser Pro Glu Ala Gly Thr Trp Asn Gln Ala Tyr Phe Glu
        355                 360                 365

Met Leu Leu Lys Asn Ala Asn Pro Ser Phe
    370                 375
```

<210> SEQ ID NO 9
<211> LENGTH: 378
<212> TYPE: PRT
<213> ORGANISM: Artificial sequence
<220> FEATURE:

-continued

<223> OTHER INFORMATION: Synthetic polypeptide for M. thermophila CBH2a
variant 47

<400> SEQUENCE: 9

```
Ala Pro Ser Arg Thr Thr Pro Gln Lys Pro Arg Gln Ala Ser Ile Gly
1               5                   10                  15

Cys Ala Ser Ala Val Thr Leu Asp Ala Ser Thr Asn Val Phe Gln Gln
            20                  25                  30

Tyr Thr Leu His Pro Asn Asn Phe Tyr Arg Ala Glu Val Glu Ala Ala
        35                  40                  45

Ala Glu Ala Ile Ser Asp Pro Ala Leu Ala Glu Lys Ala Arg Lys Val
    50                  55                  60

Ala Asp Val Gly Thr Phe Leu Trp Leu Asp Thr Ile Glu Asn Ile Gly
65                  70                  75                  80

Arg Leu Glu Pro Ala Leu Glu Asp Val Pro Cys Glu Asn Ile Val Gly
                85                  90                  95

Leu Val Ile Tyr Asp Leu Pro Gly Arg Asp Cys Ala Ala Lys Ala Ser
            100                 105                 110

Asn Gly Glu Leu Lys Val Gly Glu Leu Asp Arg Tyr Lys Thr Glu Tyr
        115                 120                 125

Ile Asp Lys Ile Ala Glu Ile Leu Lys Ala His Ser Asn Thr Ala Phe
    130                 135                 140

Ala Leu Val Ile Glu Pro Asp Ser Leu Pro Asn Leu Val Thr Asn Ser
145                 150                 155                 160

Asp Leu Gln Thr Cys Gln Gln Ser Ala Ser Gly Tyr Arg Glu Gly Val
                165                 170                 175

Ala Tyr Ala Leu Lys Gln Leu Asn Leu Pro Asn Val Val Met Tyr Ile
            180                 185                 190

Asp Ala Gly His Gly Gly Trp Leu Gly Trp Asp Trp Asn Leu Lys Pro
        195                 200                 205

Gly Ala Lys Glu Leu Ala Ser Val Tyr Lys Ser Ala Gly Ser Pro Ser
    210                 215                 220

Gln Val Arg Gly Ile Ser Thr Asn Val Ala Gly Trp Asn Ala Trp Asp
225                 230                 235                 240

Gln Glu Pro Gly Glu Phe Ser Asp Ala Ser Asp Ala Gln Tyr Asn Lys
                245                 250                 255

Cys Gln Asn Glu Lys Ile Tyr Ile His Thr Phe Gly Ala Glu Leu Lys
            260                 265                 270

Ser Ala Gly Met Pro Asn His Ala Ile Ile Asp Thr Gly Arg Asn Gly
        275                 280                 285

Val Thr Gly Leu Arg Asp Glu Trp Gly Asp Trp Cys Asn Val Asn Gly
    290                 295                 300

Ala Gly Phe Gly Val Arg Pro Thr Ala Asn Thr Gly Asp Glu Leu Ala
305                 310                 315                 320

Asp Ala Phe Val Trp Val Lys Pro Gly Gly Glu Ser Asp Gly Thr Ser
                325                 330                 335

Asp Ser Ser Ser Ala Arg Tyr Asp Ser Phe Cys Gly Lys Pro Asp Ala
            340                 345                 350

Phe Lys Pro Ser Pro Glu Ala Gly Thr Trp Asn Gln Ala Tyr Phe Glu
        355                 360                 365

Met Leu Leu Lys Asn Ala Asn Pro Ser Phe
    370                 375
```

<210> SEQ ID NO 10

```
<211> LENGTH: 378
<212> TYPE: PRT
<213> ORGANISM: Chaetomium globosum

<400> SEQUENCE: 10

Ala Pro Ser Pro Thr Thr Lys Gln Lys Pro Arg Gln Ala Gly Gly Ala
1               5                   10                  15

Cys Ala Ser Ala Val Thr Leu Asp Ala Ser Thr Asn Val Phe Lys Glu
            20                  25                  30

Tyr Thr Leu His Pro Asn Ser Phe Tyr Arg Ala Glu Val Glu Ala Ala
        35                  40                  45

Val Glu Gln Ile Thr Asp Ser Ser Leu Ala Ala Lys Ala Ala Lys Val
    50                  55                  60

Ala Asp Val Gly Thr Phe Leu Trp Leu Asp Thr Ile Glu Asn Ile Gly
65                  70                  75                  80

Lys Leu Glu Pro Ala Leu Glu Asp Val Pro Cys Glu Asn Ile Leu Gly
                85                  90                  95

Leu Val Ile Tyr Asp Leu Pro Gly Arg Asp Cys Ala Ala Lys Ala Ser
            100                 105                 110

Asn Gly Glu Leu Lys Val Gly Glu Ile Glu Lys Tyr Lys Thr Glu Tyr
        115                 120                 125

Ile Asp Lys Ile Val Thr Ile Leu Lys Ala Asn Pro Asn Thr Ala Phe
    130                 135                 140

Ala Leu Val Ile Glu Pro Asp Ser Leu Pro Asn Leu Val Thr Asn Ile
145                 150                 155                 160

Asp Leu Thr Thr Cys Gln Glu Ser Ala Asp Gly Tyr His Glu Gly Val
                165                 170                 175

Ala Tyr Ala Leu Lys Ser Leu Asn Leu Pro Asn Val Val Met Tyr Leu
            180                 185                 190

Asp Ala Gly His Gly Gly Trp Leu Gly Trp Asp Ala Asn Leu Lys Pro
        195                 200                 205

Gly Ala Glu Glu Leu Ala Lys Ala Tyr Lys Asn Ala Gly Ser Pro Ser
    210                 215                 220

Gln Phe Arg Gly Ile Ala Thr Asn Val Ala Gly Trp Asn Gln Trp Asp
225                 230                 235                 240

Leu Ser Pro Gly Glu Phe Ser Asp Thr Ser Asp Ala Lys Tyr Asn Ser
                245                 250                 255

Cys Gln Asn Glu Lys Thr Tyr Ile Thr Thr Phe Gly Ala Ala Leu Lys
            260                 265                 270

Thr Ala Gly Met Pro Asn His Ala Ile Ile Asp Thr Gly Arg Asn Gly
        275                 280                 285

Val Ser Gly Leu Arg Glu Glu Trp Gly Asn Trp Cys Asn Val Lys Gly
    290                 295                 300

Ala Gly Phe Gly Ile Arg Pro Thr Ala Asp Thr Gly Ala Asp Leu Ala
305                 310                 315                 320

Asp Ala Phe Val Trp Val Lys Pro Gly Gly Glu Ser Asp Gly Thr Ser
                325                 330                 335

Asp Thr Ser Ala Val Arg Tyr Asp Ser Phe Cys Gly Lys Pro Asp Ala
            340                 345                 350

Tyr Asn Pro Ser Pro Glu Ala Gly Gln Trp Asn Gln Ala Tyr Phe Glu
        355                 360                 365

Asp Leu Val Lys Asn Ala Lys Pro Ala Phe
    370                 375
```

-continued

```
<210> SEQ ID NO 11
<211> LENGTH: 379
<212> TYPE: PRT
<213> ORGANISM: Neurospora crassa

<400> SEQUENCE: 11

Ala Pro Ser Thr Pro Thr Leu Gln Glu Lys Pro Arg Glu Val Gln Ala
1               5                   10                  15

Gly Cys Ala Ser Ala Val Thr Leu Asp Ala Ser Thr Asn Val Trp Lys
            20                  25                  30

Lys Tyr Thr Leu His Ala Asn Lys Phe Tyr Arg Thr Glu Val Glu Ala
        35                  40                  45

Ala Val Ala Ala Ile Ser Asp Ser Ser Leu Ala Ala Lys Ala Ala Lys
    50                  55                  60

Val Ala Asn Val Gly Ser Phe Leu Trp Leu Asp Ser Ile Glu Asn Ile
65                  70                  75                  80

Gly Lys Leu Glu Pro Ala Leu Glu Asp Val Pro Cys Asp His Ile Leu
                85                  90                  95

Gly Leu Val Ile Tyr Asp Leu Pro Gly Arg Asp Cys Ala Ala Lys Ala
            100                 105                 110

Ser Asn Gly Glu Leu Ala Val Gly Glu Leu Ser Arg Tyr Lys Thr Glu
        115                 120                 125

Tyr Ile Asp Ala Ile Val Lys Ile Leu Lys Ala His Pro Lys Thr Ala
    130                 135                 140

Phe Ala Leu Val Ile Glu Pro Asp Ser Leu Pro Asn Leu Val Thr Asn
145                 150                 155                 160

Ser Asp Leu Gln Thr Cys Lys Asp Ser Ala Ser Gly Tyr Arg Asp Gly
                165                 170                 175

Val Ala Tyr Ala Leu Arg Asn Leu Asn Leu Pro Asn Val Val Met Tyr
            180                 185                 190

Ile Asp Ala Gly His Gly Gly Trp Leu Gly Trp Asp Ala Asn Leu Lys
        195                 200                 205

Pro Gly Ala Gln Glu Leu Ala Lys Ala Tyr Lys Ala Ala Gly Ser Pro
    210                 215                 220

Lys Gln Val Arg Gly Ile Ala Thr Asn Val Ala Gly Trp Asn Gln Trp
225                 230                 235                 240

Asp Leu Thr Pro Gly Glu Phe Ser Lys Ala Ser Asp Ala Lys Tyr Asn
                245                 250                 255

Lys Cys Gln Asn Glu Lys Leu Tyr Leu Asp Asn Phe Gly Pro Ala Leu
            260                 265                 270

Lys Ser Ala Gly Met Pro Asn His Ala Ile Val Asp Thr Gly Arg Asn
        275                 280                 285

Gly Val Ser Gly Leu Arg Gln Glu Trp Gly Asn Trp Cys Asn Val Asn
    290                 295                 300

Gly Ala Gly Phe Gly Val Arg Pro Thr Ser Ser Thr Gly His Asp Leu
305                 310                 315                 320

Ala Asp Ala Phe Val Trp Val Lys Pro Gly Gly Glu Ser Asp Gly Thr
                325                 330                 335

Ser Asp Ser Ser Ala Thr Arg Tyr Asp Ser Phe Cys Gly Lys Ser Asp
            340                 345                 350

Ala Tyr Gln Pro Ser Pro Glu Ala Gly Ser Trp Asn Gln Asp Tyr Phe
        355                 360                 365

Glu Met Leu Val Lys Asn Ala Lys Pro Ser Phe
    370                 375
```

-continued

<210> SEQ ID NO 12
<211> LENGTH: 379
<212> TYPE: PRT
<213> ORGANISM: Sordaria macrospora

<400> SEQUENCE: 12

```
Ala Pro Ser Thr Pro Thr Ser Gln Asp Lys Pro Arg Ala Ile Gln Ala
1               5                   10                  15

Gly Cys Ala Ser Ala Val Thr Leu Asp Ala Ser Thr Asn Val Trp Lys
            20                  25                  30

Lys Tyr Thr Leu His Ala Asn Lys Phe Tyr Arg Thr Glu Val Glu Ala
        35                  40                  45

Ala Val Gln Ala Ile Ser Asp Ser Ser Leu Ala Ser Gln Ala Ala Lys
    50                  55                  60

Val Ala Asp Val Gly Ser Phe Leu Trp Leu Asp Thr Ile Ala Asn Ile
65                  70                  75                  80

Gly Lys Leu Glu Pro Ala Leu Glu Asp Val Pro Cys Asp His Ile Leu
                85                  90                  95

Gly Leu Val Ile Tyr Asp Leu Pro Gly Arg Asp Cys Ala Ala Lys Ala
            100                 105                 110

Ser Asn Gly Glu Leu Lys Val Gly Glu Leu Asn Lys Tyr Lys Thr Glu
        115                 120                 125

Tyr Ile Asp Val Ile Val Lys Ile Leu Lys Ala His Pro Lys Thr Ala
    130                 135                 140

Phe Ala Leu Val Ile Glu Pro Asp Ser Leu Pro Asn Leu Val Thr Asn
145                 150                 155                 160

Ala Asp Val Gln Ala Cys Lys Asp Ser Ala Ser Gly Tyr Arg Asp Gly
                165                 170                 175

Val Ala Tyr Ala Leu Lys Asn Leu Asn Leu Pro Asn Val Val Met Tyr
            180                 185                 190

Ile Asp Ala Gly His Gly Gly Trp Leu Gly Trp Asp Ala Asn Leu Lys
        195                 200                 205

Pro Gly Ala Gln Glu Leu Ala Lys Ala Tyr Lys Ala Ala Gly Ser Pro
    210                 215                 220

Lys Gln Val Arg Gly Ile Ala Thr Asn Val Ala Gly Trp Asn Gln Trp
225                 230                 235                 240

Asp Leu Ser Pro Gly Glu Phe Ser Lys Ala Ser Asp Ala Lys Tyr Asn
                245                 250                 255

Lys Cys Gln Asn Glu Lys Leu Tyr Leu Asp Asn Phe Gly Pro Ala Leu
            260                 265                 270

Lys Ser Ala Gly Met Pro Asn His Ala Ile Val Asp Thr Gly Arg Asn
        275                 280                 285

Gly Val Ser Gly Leu Arg Glu Glu Trp Gly Asn Trp Cys Asn Val Asn
    290                 295                 300

Gly Ala Gly Phe Gly Thr Arg Pro Thr Ser Thr Thr Gly His Asp Leu
305                 310                 315                 320

Ala Asp Ala Phe Val Trp Val Lys Pro Gly Gly Glu Ser Asp Gly Thr
                325                 330                 335

Ser Asp Ser Ser Ala Thr Arg Tyr Asp Ser Phe Cys Gly Lys Ser Asp
            340                 345                 350

Ala Tyr Gln Pro Ser Pro Glu Ala Gly Asn Trp Asn Gln Glu Tyr Phe
        355                 360                 365

Glu Met Leu Leu Lys Asn Ala Lys Pro Ala Phe
    370                 375
```

```
<210> SEQ ID NO 13
<211> LENGTH: 380
<212> TYPE: PRT
<213> ORGANISM: Podospora anserina

<400> SEQUENCE: 13

Ala Pro Ser Pro Thr Thr Gln Asp Lys Pro Thr Lys Arg Gln Ala Gly
1               5                   10                  15

Cys Ala Ser Ala Val Ser Leu Asn Ala Gln Thr Asn Val Phe Lys Gln
            20                  25                  30

Tyr Thr Leu His Ala Asn Asn Phe Tyr Arg Lys Glu Ile Glu Glu Leu
        35                  40                  45

Ala Ile Pro Asn Leu Ser Asp Pro Ser Leu Glu Ala Ala Ala Arg Lys
    50                  55                  60

Val Ala Asp Thr Gly Ser Phe Val Trp Leu Asp Thr Ile Ala Asn Val
65                  70                  75                  80

Asp Arg Leu Glu Pro Ala Leu Ala Glu Val Pro Cys Asn Glu Ile Leu
                85                  90                  95

Gly Val Val Val Tyr Asp Leu Pro Gly Arg Asp Cys Ala Ala Lys Ala
            100                 105                 110

Ser Asn Gly Glu Leu Lys Val Gly Glu Leu Asn Arg Tyr Lys Thr Glu
        115                 120                 125

Phe Ile Asp Arg Ile Ala Ser Ile Leu Lys Ala His Pro Asn Thr Ala
    130                 135                 140

Val Ala Leu Val Ile Glu Pro Asp Ser Leu Pro Asn Leu Val Thr Asn
145                 150                 155                 160

Ser Asp Val Gln Ala Cys Arg Asn Ser Ala Ala Gly Tyr Arg Asp Gly
                165                 170                 175

Val Ala Tyr Ala Leu Lys Thr Leu Asn Leu Pro Asn Val Val Gln Tyr
            180                 185                 190

Ile Asp Ala Gly His Gly Gly Trp Leu Gly Trp Asp Ala Asn Leu Lys
        195                 200                 205

Pro Gly Ala Glu Glu Leu Ala Lys Ala Tyr Lys Ala Ala Gly Ser Pro
    210                 215                 220

Lys Gln Phe Arg Gly Ile Ala Thr Asn Val Ala Gly Trp Asn Ala Trp
225                 230                 235                 240

Asp Leu Ser Pro Gly Glu Phe Ser Ser Ala Ser Asp Ala Lys Tyr Asn
                245                 250                 255

Ser Cys Gln Asn Glu Arg Thr Tyr Val Asn Thr Phe Gly Gln Arg Leu
            260                 265                 270

Lys Ala Ala Gly Met Pro Asn His Ala Ile Val Asp Thr Gly Arg Asn
        275                 280                 285

Gly Val Gln Gly Leu Arg Glu Glu Trp Gly Asn Trp Cys Asn Val Asp
    290                 295                 300

Gly Ala Gly Phe Gly Arg Pro Pro Ser Ala Asp Thr Gly Leu Glu Leu
305                 310                 315                 320

Ala Asp Ala Phe Val Trp Val Lys Pro Gly Gly Glu Ser Asp Gly Thr
                325                 330                 335

Ser Asp Ser Ser Ala Val Arg Tyr Asp Ser Phe Cys Gly Lys Pro Asp
            340                 345                 350

Ala Phe Gln Pro Ser Pro Glu Ala Gly Ala Trp His Gln Glu Tyr Phe
        355                 360                 365

Glu Met Leu Leu Arg Asn Ser Asn Pro Ser Leu Leu
```

```
    370                 375                 380

<210> SEQ ID NO 14
<211> LENGTH: 378
<212> TYPE: PRT
<213> ORGANISM: Magnaporthe oryzae

<400> SEQUENCE: 14

Ser Pro Ser Arg Thr Val Lys Ser Gln Pro Gly Gln Ala Ala Ala Gly
1               5                   10                  15

Cys Ser Ser Ala Val Thr Leu Asp Ala Ser Thr Asn Val Phe Ser Lys
            20                  25                  30

Tyr Thr Leu His Pro Asn Ser Phe Tyr Arg Ala Glu Val Glu Ala Ala
        35                  40                  45

Ala Glu Ala Ile Ser Asp Ser Thr Leu Lys Ala Gln Ala Leu Lys Val
    50                  55                  60

Ala Asp Val Gly Ser Phe Leu Trp Ile Asp Thr Ile Ser Ala Ile Ser
65                  70                  75                  80

Arg Ile Glu Pro Gly Val Ser Asp Gln Pro Cys Asp His Ile Leu Gly
                85                  90                  95

Leu Val Ile Tyr Asp Leu Pro Gly Arg Asp Cys Ala Ala Lys Ala Ser
            100                 105                 110

Asn Gly Glu Leu Lys Val Gly Glu Leu Ala Lys Tyr Lys Ser Gln Tyr
        115                 120                 125

Ile Asp Pro Ile Ala Ala Leu Leu Lys Lys Tyr Asn Asn His Ala Phe
    130                 135                 140

Ala Leu Leu Ile Glu Pro Asp Ser Leu Pro Asn Leu Val Thr Asn Ser
145                 150                 155                 160

Asp Leu Ser Ala Cys Gln Gln Ser Ala Ala Gly Tyr Arg Asp Gly Val
                165                 170                 175

Ala Tyr Ala Leu Lys Thr Leu Asn Leu Pro Asn Val Val Met Tyr Ile
            180                 185                 190

Asp Ala Gly His Gly Gly Trp Leu Gly Trp Asn Asp Asn Leu Lys Pro
        195                 200                 205

Gly Ala Glu Glu Leu Ala Lys Ala Tyr Lys Ala Ala Gly Ser Pro Lys
    210                 215                 220

Gln Phe Arg Gly Phe Ala Thr Asn Val Ala Gly Trp Asn Ala Trp Asp
225                 230                 235                 240

Leu Thr Pro Gly Glu Phe Ser Ser Ala Ser Asp Ala Gln Trp Asn Lys
                245                 250                 255

Cys Gln Asn Glu Lys Ile Tyr Val Glu Thr Phe Gly Pro Leu Leu Lys
            260                 265                 270

Asn Ala Gly Met Pro Asn His Ala Ile Val Asp Val Gly Arg Asn Ala
        275                 280                 285

Val Gln Gly Leu Arg Glu Glu Trp Gly His Trp Cys Asn Val Asn Gly
    290                 295                 300

Ala Gly Phe Gly Val Arg Pro Thr Thr Ser Thr Gly Ser Ser Leu Thr
305                 310                 315                 320

Asp Ala Leu Leu Trp Val Lys Pro Gly Gly Glu Ser Asp Gly Thr Ser
                325                 330                 335

Asp Thr Ser Ala Thr Arg Tyr Asp Ser Phe Cys Gly Met Ser Asp Ala
            340                 345                 350

Tyr Lys Pro Ser Pro Glu Ala Gly Gln Trp Asn Gln Asp Tyr Phe Glu
        355                 360                 365
```

```
Met Leu Leu Arg Asn Ala Lys Pro Gln Phe
    370                 375


<210> SEQ ID NO 15
<211> LENGTH: 378
<212> TYPE: PRT
<213> ORGANISM: Leptosphaeria maculans

<400> SEQUENCE: 15

Leu Pro Ser Pro Thr Glu Gln Gly Pro Ile Thr Ala Arg Ala Ala Ala
1               5                   10                  15

Ala Ala Cys Ala Thr Pro Val Thr Leu Ser Gly Asn Pro Phe Ala Ser
            20                  25                  30

Arg Ser Ile Tyr Ala Asn Lys Phe Tyr Ser Ser Glu Val Ala Ala Ala
        35                  40                  45

Ala Ala Ala Met Thr Asp Thr Ala Leu Ala Ser Ala Ala Ala Lys Val
    50                  55                  60

Ala Asn Val Gly Thr Phe Leu Trp Ile Asp Thr Arg Ala Lys Ile Ala
65                  70                  75                  80

Val Val Glu Asp Gly Ile Lys Asp Val Pro Cys Asp Gln Ile Ala Ala
                85                  90                  95

Leu Val Ile Tyr Asp Leu Pro Gly Arg Asp Cys Ala Ala Lys Ala Ser
            100                 105                 110

Asn Gly Glu Leu Ala Val Gly Glu Leu Asp Ile Tyr Lys Arg Glu Tyr
        115                 120                 125

Ile Asp Pro Ile Val Ala Ile Phe Lys Lys Tyr Pro Asn Thr Ala Ile
    130                 135                 140

Ala Leu Val Ile Glu Pro Asp Ser Leu Pro Asn Leu Val Thr Asn Ala
145                 150                 155                 160

Lys Leu Gln Thr Cys Gln Asp Ser Ala Ser Gly Tyr Arg Glu Gly Val
                165                 170                 175

Ala Tyr Ala Leu Lys Gln Phe Asn Met Pro Asn Ile Ala Met Tyr Ile
            180                 185                 190

Asp Ala Gly His Gly Gly Trp Leu Gly Trp Asn Asp Asn Leu Lys Pro
        195                 200                 205

Gly Ala Lys Glu Leu Ala Thr Val Tyr Lys Asn Ala Gly Ser Pro Lys
    210                 215                 220

Ser Val Arg Gly Ile Ala Thr Asn Val Ala Gly Trp Asn Ala Trp Asp
225                 230                 235                 240

Gln Thr Pro Gly Glu Phe Ser Thr Ala Thr Asp Ala Gln Trp Asn Lys
                245                 250                 255

Ala Gln Asn Glu Lys Leu Tyr Ile Glu Leu Phe Ser Pro Glu Leu Lys
            260                 265                 270

Ser Ala Gly Met Pro Gly Gln Ala Ile Val Asp Thr Gly Arg Asn Ala
        275                 280                 285

Val Thr Gly Leu Arg Arg Glu Trp Gly Asn Trp Cys Asn Val Asn Gly
    290                 295                 300

Ala Gly Phe Gly Val Arg Pro Thr Ser Asn Thr Gly Ser Ser Leu Val
305                 310                 315                 320

Asp Ser Phe Val Trp Val Lys Pro Gly Gly Glu Ser Asp Gly Thr Ser
                325                 330                 335

Asp Pro Ser Ala Thr Arg Tyr Asp Ser Phe Cys Gly Lys Glu Asp Ala
            340                 345                 350

Phe Lys Pro Ser Pro Glu Ala Gly Gln Trp Asn Gln Ala Tyr Phe Glu
        355                 360                 365
```

Met Leu Val Lys Asn Ala Lys Pro Ala Phe
    370                 375

<210> SEQ ID NO 16
<211> LENGTH: 366
<212> TYPE: PRT
<213> ORGANISM: Phaeosphaeria nodorum

<400> SEQUENCE: 16

Ala Pro Ser Pro Val Glu Asn Gly Pro Ile Thr Ala Arg Ala Val Gly
1               5                   10                  15

Ala Ala Ala Ala Ala Cys Ala Thr Pro Val Thr Leu Ser Gly Asn Pro
            20                  25                  30

Phe Ala Ser Arg Gln Ile Tyr Ala Asn Lys Phe Tyr Ser Ser Glu Val
        35                  40                  45

Ser Ala Ala Ala Ala Ala Met Thr Asp Ser Ala Leu Ala Ala Ser Ala
    50                  55                  60

Thr Lys Ile Asp Ile Val Glu Asp Thr Ile Lys Asp Val Pro Cys Asp
65                  70                  75                  80

Gln Ile Ala Ala Leu Val Ile Tyr Asp Leu Pro Gly Arg Asp Cys Ala
                85                  90                  95

Ala Lys Ala Ser Asn Gly Glu Leu Pro Val Gly Ser Leu Glu Thr Tyr
            100                 105                 110

Lys Thr Glu Tyr Ile Asp Pro Ile Val Ala Ile Phe Lys Lys Tyr Pro
        115                 120                 125

Asn Ile Ala Ile Ala Leu Val Ile Glu Pro Asp Ser Leu Pro Asn Leu
    130                 135                 140

Val Thr Asn Ala Asn Leu Gln Thr Cys Lys Asp Ser Ala Glu Gly Tyr
145                 150                 155                 160

Arg Lys Gly Val Ala Tyr Ala Leu Lys Ser Leu Asn Leu Pro Asn Ile
                165                 170                 175

Ala Met Tyr Ile Asp Ala Gly His Gly Gly Trp Leu Gly Trp Asn Asp
            180                 185                 190

Asn Leu Lys Pro Gly Ala Lys Glu Leu Ala Thr Val Tyr Lys Asp Ala
        195                 200                 205

Gly Ser Pro Lys Gln Val Arg Gly Val Ser Thr Asn Val Ala Gly Trp
    210                 215                 220

Asn Ala Tyr Asp Leu Ser Pro Gly Glu Phe Ser Lys Ala Thr Asp Ala
225                 230                 235                 240

Gln Tyr Asn Lys Ala Gln Asn Glu Lys Leu Phe Val Ser Met Phe Ser
                245                 250                 255

Pro Glu Leu Lys Ser Ala Gly Met Pro Gly Gln Ala Ile Ile Asp Thr
            260                 265                 270

Ala Arg Asn Gly Val Thr Gly Leu Arg Lys Glu Trp Gly Asp Trp Cys
        275                 280                 285

Asn Val Lys Gly Ala Gly Phe Gly Val Arg Pro Thr Gly Asn Thr Gly
    290                 295                 300

Asn Thr Leu Val Asp Ala Phe Val Trp Val Lys Pro Gly Gly Glu Ser
305                 310                 315                 320

Asp Gly Thr Ser Asp Ser Ser Ala Thr Arg Tyr Asp Ser Phe Cys Gly
                325                 330                 335

Lys Asp Asp Ala Phe Lys Pro Ser Pro Glu Ala Gly Gln Trp His Gln
            340                 345                 350

Ala Tyr Phe Glu Glu Leu Val Lys Asn Ala Lys Pro Ala Leu 355 360 365

<210> SEQ ID NO 17
<211> LENGTH: 367
<212> TYPE: PRT
<213> ORGANISM: Schizophyllum commune

<400> SEQUENCE: 17

Ser Pro Ala Asn Arg Lys Arg Arg Pro Ala Val Thr Leu Glu Gly Asn
1 5 10 15

Pro Phe Glu Ser Tyr Thr Leu His Ala Asn Ser His Tyr Ser Ser Leu
20 25 30

Val Glu Ala Ala Ile Gly Asn Leu Ser Asp Ser Ser Leu Glu Pro Ala
35 40 45

Ala Gln Val Val Lys Glu Thr Gly Thr Phe Leu Trp Leu Asp Thr Ile
50 55 60

Ser Thr Ile Glu Thr Phe Glu Gly Tyr Leu Gln Glu Thr Gly Glu Asn
65 70 75 80

Glu Ile Phe Gly Val Val Ile Tyr Asp Leu Pro Gly Arg Asp Cys Ala
85 90 95

Ala Lys Ala Ser Asn Gly Glu Leu Ala Val Gly Glu Leu Asp Arg Tyr
100 105 110

Lys Ser Glu Tyr Ile Asp Pro Ile Val Ala Ile Ile Lys Asn Asn Pro
115 120 125

Asp Ile Ala Ile Ala Ala Ile Ile Glu Pro Asp Ser Leu Pro Asn Leu
130 135 140

Val Thr Asn Ser Asp Leu Thr Thr Cys Gln Asn Ser Ala Ser Gly Tyr
145 150 155 160

Glu Glu Gly Val Ala Tyr Ala Leu Ser Ser Leu Asp Leu Pro Asn Val
165 170 175

Val Gln Tyr Val Asp Ala Gly His Gly Gly Trp Leu Gly Trp Asp Ala
180 185 190

Asn Leu Lys Pro Gly Ala Glu Glu Leu Ala Lys Val Tyr Lys Ala Ala
195 200 205

Gly Ser Pro Ser Asn Val Arg Gly Ile Ser Thr Asn Val Ala Gly Trp
210 215 220

Asn Ala Trp Ser Lys Asn Pro Gly Glu Phe Glu Asn Ala Pro Asp Gly
225 230 235 240

Gln Tyr Asn Lys Cys Gln Asp Glu Gln Arg Tyr Val Thr Ile Phe Gly
245 250 255

Asp Ala Leu Ser Ala Ala Gly Phe Pro Asn His Ala Ile Val Asp Thr
260 265 270

Ala Arg Asn Gly Val Gln Gly Leu Arg Asp Ala Trp Gly Asp Trp Cys
275 280 285

Asn Val Ile Gly Ala Gly Ile Gly Val Arg Pro Thr Ala Asp Thr Gly
290 295 300

Glu Glu Leu Ala Asp Ala Phe Val Trp Val Lys Pro Ala Gly Glu Ser
305 310 315 320

Asp Gly Thr Ser Asp Ser Ser Ala Thr Arg Tyr Asp Ser Met Cys Gly
325 330 335

Leu Asp Asp Ala Tyr Lys Pro Ser Pro Glu Ala Gly Ala Trp Asn Gln
340 345 350

Pro Tyr Phe Glu Glu Leu Leu Lys Asn Ala Asn Pro Ser Leu Ala
355 360 365

<210> SEQ ID NO 18
<211> LENGTH: 375
<212> TYPE: PRT
<213> ORGANISM: Pyrenophora teres

<400> SEQUENCE: 18

```
Ala Pro Thr Pro Asp Asp Asn Gly Pro Leu Ala Ala Arg Ala Ala Cys
1               5                   10                  15

Ser Ser Pro Val Thr Leu Ser Gly Asn Pro Phe Thr Gly Arg Lys Ile
            20                  25                  30

Tyr Ala Asn Lys Phe Tyr Ala Ala Glu Val Asn Lys Ala Ala Ala Ala
        35                  40                  45

Ile Ser Asp Ala Thr Leu Ala Ala Ala Ala Lys Lys Val Ala Asp Val
    50                  55                  60

Gly Thr Tyr Phe Trp Ile Asp Thr Arg Ala Lys Ile Ala Met Val Glu
65                  70                  75                  80

Asp Glu Leu Lys Asn Val Ser Cys Asp Gln Ile Ala Ala Phe Val Ile
                85                  90                  95

Tyr Asp Leu Pro Gly Arg Asp Cys Ala Ala Lys Ala Ser Asn Gly Glu
            100                 105                 110

Leu Ala Val Gly Gln Leu Asp Val Tyr Lys Thr Glu Tyr Ile Asp Pro
        115                 120                 125

Ile Val Ala Ile Phe Lys Lys Tyr Pro Asn Thr Ala Ile Ser Leu Ile
    130                 135                 140

Ile Glu Pro Asp Ser Leu Pro Asn Leu Val Thr Asn Ala Asn Leu Gln
145                 150                 155                 160

Ala Cys Gln Gln Ser Ala Ser Gly Tyr Arg Glu Gly Val Ala Tyr Ala
                165                 170                 175

Leu Lys Gln Leu Asn Leu Pro Asn Ile Ala Met Tyr Ile Asp Ala Gly
            180                 185                 190

His Gly Gly Trp Leu Gly Trp Asp Asp Asn Ile Lys Pro Gly Ala Lys
        195                 200                 205

Glu Leu Ala Thr Val Tyr Lys Asn Ala Gly Ser Pro Lys Ser Val Arg
    210                 215                 220

Gly Ile Ser Thr Asn Ile Ala Gly Trp Asn Ala Phe Asp Leu Ser Pro
225                 230                 235                 240

Gly Glu Phe Ala Asn Ser Ala Asp Gly Lys Tyr Asn Lys Ala Gln Asn
                245                 250                 255

Glu Lys Leu Tyr Val Ser Leu Ile Ser Pro Glu Leu Val Lys Asn Gly
            260                 265                 270

Met Pro Gly Gln Ala Ile Val Asp Thr Gly Arg Asn Gly Val Thr Gly
        275                 280                 285

Leu Arg Ala Glu Trp Gly Asp Trp Cys Asn Val Asn Gly Ala Gly Phe
    290                 295                 300

Gly Val Arg Pro Thr Thr Asn Thr Gly Ser Ser Leu Val Asp Ser Phe
305                 310                 315                 320

Val Trp Gly Lys Pro Gly Gly Glu Ser Asp Gly Thr Ser Asp Ser Ser
                325                 330                 335

Ala Thr Arg Tyr Asp Ser Phe Cys Gly Lys Ser Asp Ala Tyr Lys Pro
            340                 345                 350

Ser Pro Glu Ala Gly Gln Trp Asn Gln Pro Tyr Phe Glu Met Leu Val
        355                 360                 365

Lys Asn Ala Lys Pro Ala Phe
    370                 375
```

<210> SEQ ID NO 19
<211> LENGTH: 356
<212> TYPE: PRT
<213> ORGANISM: Pyrenophora tritici-repentis

<400> SEQUENCE: 19

```
Ala Pro Thr Pro Ala Asp Asn Gly Pro Leu Ala Ala Arg Ala Ala Cys
1               5                   10                  15

Ser Ser Pro Val Thr Leu Thr Gly Asn Pro Phe Thr Gly Arg Lys Ile
            20                  25                  30

Tyr Ala Asn Lys Phe Tyr Ala Asp Glu Val Asn Lys Ala Ala Ala Ala
        35                  40                  45

Met Thr Asp Ser Thr Leu Ala Ala Ala Ala Lys Lys Val Ala Asp Val
    50                  55                  60

Gly Thr Tyr Phe Trp Ile Asp Thr Arg Ala Lys Ile Ala Met Ile Glu
65                  70                  75                  80

Asp Glu Leu Lys Asn Val Ser Cys Asp Gln Ile Ala Ala Phe Val Ile
                85                  90                  95

Tyr Asp Leu Pro Gly Arg Asp Cys Ala Ala Lys Ala Ser Asn Gly Glu
            100                 105                 110

Leu Ala Val Gly Gln Leu Asp Val Tyr Lys Thr Glu Tyr Ile Asp Pro
        115                 120                 125

Ile Val Ala Ile Phe Lys Lys Tyr Pro Asn Thr Ala Ile Ser Leu Ile
    130                 135                 140

Ile Glu Pro Asp Ser Leu Pro Asn Leu Val Thr Asn Ala Asn Val Gln
145                 150                 155                 160

Ala Cys Gln Gln Ser Ala Ser Gly Tyr Arg Asp Gly Val Ala Tyr Ala
                165                 170                 175

Leu Lys Gln Leu Asn Leu Pro Asn Ile Ala Met Tyr Ile Asp Ala Gly
            180                 185                 190

His Gly Gly Trp Leu Gly Trp Asp Asp Asn Ile Lys Pro Gly Ala Lys
        195                 200                 205

Glu Leu Ala Thr Val Tyr Lys Ala Ala Gly Ser Pro Lys Gln Val Arg
    210                 215                 220

Gly Ile Ser Thr Asn Ile Ala Gly Trp Asn Ala Trp Asp Leu Ser Pro
225                 230                 235                 240

Gly Glu Phe Ala Asn Ser Ala Asp Gly Lys Tyr Asn Lys Ala Gln Asn
                245                 250                 255

Glu Lys Leu Tyr Ile Gly Leu Ile Ser Pro Glu Leu Val Lys Asn Gly
            260                 265                 270

Met Pro Gly Gln Ala Ile Val Asp Thr Gly Arg Asn Gly Val Thr Gly
        275                 280                 285

Leu Arg Ala Glu Trp Gly Asp Cys Leu Val Asp Ser Phe Val Trp Gly
    290                 295                 300

Lys Pro Gly Gly Glu Ser Asp Gly Thr Ser Asp Ser Ser Ala Thr Arg
305                 310                 315                 320

Tyr Asp Ser Phe Cys Gly Lys Ser Asp Ala Tyr Lys Pro Ser Pro Glu
                325                 330                 335

Ala Gly Gln Trp Asn Gln Ala Tyr Phe Glu Met Leu Val Lys Asn Ala
            340                 345                 350

Lys Pro Ala Phe
        355
```

-continued

<210> SEQ ID NO 20
<211> LENGTH: 465
<212> TYPE: PRT
<213> ORGANISM: Myceliophthora thermophila

<400> SEQUENCE: 20

```
Ala Pro Val Ile Glu Glu Arg Gln Asn Cys Gly Ala Val Trp Thr Gln
1               5                   10                  15

Cys Gly Gly Asn Gly Trp Gln Gly Pro Thr Cys Cys Ala Ser Gly Ser
            20                  25                  30

Thr Cys Val Ala Gln Asn Glu Trp Tyr Ser Gln Cys Leu Pro Asn Ser
        35                  40                  45

Gln Val Thr Ser Ser Thr Thr Pro Ser Ser Thr Ser Thr Ser Gln Arg
    50                  55                  60

Ser Thr Ser Thr Ser Ser Ser Thr Thr Arg Ser Gly Ser Ser Ser Ser
65                  70                  75                  80

Ser Ser Thr Thr Pro Pro Pro Val Ser Ser Pro Val Thr Ser Ile Pro
                85                  90                  95

Gly Gly Ala Thr Ser Thr Ala Ser Tyr Ser Gly Asn Pro Phe Ser Gly
            100                 105                 110

Val Arg Leu Phe Ala Asn Asp Tyr Tyr Arg Ser Glu Val His Asn Leu
        115                 120                 125

Ala Ile Pro Ser Met Thr Gly Thr Leu Ala Ala Lys Ala Ser Ala Val
    130                 135                 140

Ala Glu Val Pro Ser Phe Gln Trp Leu Asp Arg Asn Val Thr Ile Asp
145                 150                 155                 160

Thr Leu Met Val Gln Thr Leu Ser Gln Val Arg Ala Leu Asn Lys Ala
                165                 170                 175

Gly Ala Asn Pro Pro Tyr Ala Ala Gln Leu Val Val Tyr Asp Leu Pro
            180                 185                 190

Asp Arg Asp Cys Ala Ala Ala Ala Ser Asn Gly Glu Phe Ser Ile Ala
        195                 200                 205

Asn Gly Gly Ala Ala Asn Tyr Arg Ser Tyr Ile Asp Ala Ile Arg Lys
    210                 215                 220

His Ile Ile Glu Tyr Ser Asp Ile Arg Ile Ile Leu Val Ile Glu Pro
225                 230                 235                 240

Asp Ser Met Ala Asn Met Val Thr Asn Met Asn Val Ala Lys Cys Ser
                245                 250                 255

Asn Ala Ala Ser Thr Tyr His Glu Leu Thr Val Tyr Ala Leu Lys Gln
            260                 265                 270

Leu Asn Leu Pro Asn Val Ala Met Tyr Leu Asp Ala Gly His Ala Gly
        275                 280                 285

Trp Leu Gly Trp Pro Ala Asn Ile Gln Pro Ala Ala Glu Leu Phe Ala
    290                 295                 300

Gly Ile Tyr Asn Asp Ala Gly Lys Pro Ala Ala Val Arg Gly Leu Ala
305                 310                 315                 320

Thr Asn Val Ala Asn Tyr Asn Ala Trp Ser Ile Ala Ser Ala Pro Ser
                325                 330                 335

Tyr Thr Ser Pro Asn Pro Asn Tyr Asp Glu Lys His Tyr Ile Glu Ala
            340                 345                 350

Phe Ser Pro Leu Leu Asn Ser Ala Gly Phe Pro Ala Arg Phe Ile Val
        355                 360                 365

Asp Thr Gly Arg Asn Gly Lys Gln Pro Thr Gly Gln Gln Gln Trp Gly
    370                 375                 380
```

-continued

```
Asp Trp Cys Asn Val Lys Gly Thr Gly Phe Gly Val Arg Pro Thr Ala
385                 390                 395                 400

Asn Thr Gly His Glu Leu Val Asp Ala Phe Val Trp Val Lys Pro Gly
                405                 410                 415

Gly Glu Ser Asp Gly Thr Ser Asp Thr Ser Ala Ala Arg Tyr Asp Tyr
            420                 425                 430

His Cys Gly Leu Ser Asp Ala Leu Gln Pro Ala Pro Glu Ala Gly Gln
        435                 440                 445

Trp Phe Gln Ala Tyr Phe Glu Gln Leu Leu Thr Asn Ala Asn Pro Pro
    450                 455                 460

Phe
465
```

<210> SEQ ID NO 21
<211> LENGTH: 2487
<212> TYPE: DNA
<213> ORGANISM: Myceliophthora thermophila

<400> SEQUENCE: 21

```
atgaggacct cctctcgttt aatcggtgcc cttgcggcgg cactcttgcc gtctgccctt     60

gcgcagaaca acgcgccggt aaccttcacc gacccggact cgggcattac cttcaacacg    120

tggggtctcg ccgaggattc tccccagact aagggcggtt tcacttttgg tgttgctctg    180

ccctctgatg ccctcacgac agacgccaag gagttcatcg gttacttgaa atgcgcgagg    240

aacgatgaga gcggttggtg cggtgtctcc ctgggcggcc ccatgaccaa ctcgctcctc    300

atcgcggcct ggccccacga ggacaccgtc tacacctctc tccgcttcgc caccggctat    360

gccatgccgg atgtctacca gggggacgcc gagatcaccc aggtctcctc ctctgtcaac    420

tcgacgcact tcagcctcat cttcaggtgc gagaactgcc tgcaatggag tcaaagcggc    480

gccaccggcg gtgcctccac ctcgaacggc gtgttggtcc tcggctgggt ccaggcattc    540

gccgaccccg gcaacccgac ctgccccgac cagatcaccc tcgagcagca cgacaacggc    600

atgggtatct ggggtgccca gctcaactcc gacgccgcca gcccgtccta caccgagtgg    660

gccgcccagg ccaccaagac cgtcacgggt gactgcggcg gtcccaccga gacctctgtc    720

gtcggtgtcc ccgttccgac gggcgtctcg ttcgattaca tcgtcgtggg cggcggtgcc    780

ggtggcatcc ccgccgccga caagctcagc gaggccggca agagtgtgct gctcatcgag    840

aagggctttg cctcgaccgc caacaccgga ggcactctcg gccccgagtg gctcgagggc    900

cacgacctta cccgctttga cgtgccgggt ctgtgcaacc agatctgggt tgactccaag    960

gggatcgctt gcgaggatac cgaccagatg gctggctgtg tcctcggcgg cggtaccgcc   1020

gtgaatgccg gcctgtggtt caagccctac tcgctcgact gggactacct cttccctagt   1080

ggttggaagt acaaagacgt ccagccggcc atcaaccgcg ccctctcgcg catcccgggc   1140

accgatgctc cctcgaccga cggcaagcgc tactaccaac agggcttcga cgtcctctcc   1200

aagggcctgg ccggcggcgg ctggacctcg gtcacggcca ataacgcgcc agacaagaag   1260

aaccgcacct tctcccatgc cccctcatg ttcgccggcg gcgagcgcaa cggcccgctg   1320

ggcacctact tccagaccgc caagaagcgc agcaacttca agctctggct caacacgtcg   1380

gtcaagcgcg tcatccgcca gggcggccac atcaccggcg tcgaggtcga gccgttccgc   1440

gacggcggtt accaaggcat cgtccccgtc accaaggtta cgggccgcgt catcctctct   1500

gccggtacct ttggcagtgc aaagatcctg ctgaggagcg gtatcggtcc gaacgatcag   1560

ctgcaggttg tcgcggcctc ggagaaggat ggccctacca tgatcagcaa ctcgtcctgg   1620
```

atcaacctgc ctgtcggcta caacctggat gaccacctca acaccgacac tgtcatctcc 1680
caccccgacg tcgtgttcta cgacttctac gaggcgtggg acaatcccat ccagtctgac 1740
aaggacagct acctcaactc gcgcacgggc atcctcgccc aagccgctcc caacattggg 1800
cctatgttct gggaagagat caagggtgcg gacggcattg ttcgccagct ccagtggact 1860
gcccgtgtcg agggcagcct gggtgccccc aacggcaaga ccatgaccat gtcgcagtac 1920
ctcggtcgtg gtgccacctc gcgcggccgc atgaccatca ccccgtccct gacaactgtc 1980
gtctcggacg tgccctacct caaggacccc aacgacaagg aggccgtcat ccagggcatc 2040
atcaacctgc agaacgccct caagaacgtc gccaacctga cctggctctt ccccaactcg 2100
accatcacgc cgcgccaata cgttgacagc atggtcgtct ccccgagcaa ccggcgctcc 2160
aaccactgga tgggcaccaa caagatcggc accgacgacg ggcgcaaggg cggctccgcc 2220
gtcgtcgacc tcaacaccaa ggtctacggc accgacaacc tcttcgtcat cgacgcctcc 2280
atcttccccg gcgtgcccac caccaacccc acctcgtaca tcgtgacggc gtcggagcac 2340
gcctcggccc gcatcctcgc cctgcccgac ctcacgcccg tccccaagta cgggcagtgc 2400
ggcggccgcg aatggagcgg cagcttcgtc tgcgccgacg gctccacgtg ccagatgcag 2460
aacgagtggt actcgcagtg cttgtga 2487

<210> SEQ ID NO 22
<211> LENGTH: 828
<212> TYPE: PRT
<213> ORGANISM: Myceliophthora thermophila

<400> SEQUENCE: 22

Met Arg Thr Ser Ser Arg Leu Ile Gly Ala Leu Ala Ala Ala Leu Leu
1 5 10 15

Pro Ser Ala Leu Ala Gln Asn Asn Ala Pro Val Thr Phe Thr Asp Pro
20 25 30

Asp Ser Gly Ile Thr Phe Asn Thr Trp Gly Leu Ala Glu Asp Ser Pro
35 40 45

Gln Thr Lys Gly Gly Phe Thr Phe Gly Val Ala Leu Pro Ser Asp Ala
50 55 60

Leu Thr Thr Asp Ala Lys Glu Phe Ile Gly Tyr Leu Lys Cys Ala Arg
65 70 75 80

Asn Asp Glu Ser Gly Trp Cys Gly Val Ser Leu Gly Gly Pro Met Thr
85 90 95

Asn Ser Leu Leu Ile Ala Ala Trp Pro His Glu Asp Thr Val Tyr Thr
100 105 110

Ser Leu Arg Phe Ala Thr Gly Tyr Ala Met Pro Asp Val Tyr Gln Gly
115 120 125

Asp Ala Glu Ile Thr Gln Val Ser Ser Ser Val Asn Ser Thr His Phe
130 135 140

Ser Leu Ile Phe Arg Cys Glu Asn Cys Leu Gln Trp Ser Gln Ser Gly
145 150 155 160

Ala Thr Gly Gly Ala Ser Thr Ser Asn Gly Val Leu Val Leu Gly Trp
165 170 175

Val Gln Ala Phe Ala Asp Pro Gly Asn Pro Thr Cys Pro Asp Gln Ile
180 185 190

Thr Leu Glu Gln His Asp Asn Gly Met Gly Ile Trp Gly Ala Gln Leu
195 200 205

Asn Ser Asp Ala Ala Ser Pro Ser Tyr Thr Glu Trp Ala Ala Gln Ala

-continued

```
    210                 215                 220

Thr Lys Thr Val Thr Gly Asp Cys Gly Gly Pro Thr Glu Thr Ser Val
225                 230                 235                 240

Val Gly Val Pro Val Pro Thr Gly Val Ser Phe Asp Tyr Ile Val Val
                245                 250                 255

Gly Gly Gly Ala Gly Gly Ile Pro Ala Ala Asp Lys Leu Ser Glu Ala
            260                 265                 270

Gly Lys Ser Val Leu Leu Ile Glu Lys Gly Phe Ala Ser Thr Ala Asn
        275                 280                 285

Thr Gly Gly Thr Leu Gly Pro Glu Trp Leu Glu Gly His Asp Leu Thr
    290                 295                 300

Arg Phe Asp Val Pro Gly Leu Cys Asn Gln Ile Trp Val Asp Ser Lys
305                 310                 315                 320

Gly Ile Ala Cys Glu Asp Thr Asp Gln Met Ala Gly Cys Val Leu Gly
                325                 330                 335

Gly Gly Thr Ala Val Asn Ala Gly Leu Trp Phe Lys Pro Tyr Ser Leu
            340                 345                 350

Asp Trp Asp Tyr Leu Phe Pro Ser Gly Trp Lys Tyr Lys Asp Val Gln
        355                 360                 365

Pro Ala Ile Asn Arg Ala Leu Ser Arg Ile Pro Gly Thr Asp Ala Pro
    370                 375                 380

Ser Thr Asp Gly Lys Arg Tyr Tyr Gln Gln Gly Phe Asp Val Leu Ser
385                 390                 395                 400

Lys Gly Leu Ala Gly Gly Gly Trp Thr Ser Val Thr Ala Asn Asn Ala
                405                 410                 415

Pro Asp Lys Lys Asn Arg Thr Phe Ser His Ala Pro Phe Met Phe Ala
            420                 425                 430

Gly Gly Glu Arg Asn Gly Pro Leu Gly Thr Tyr Phe Gln Thr Ala Lys
        435                 440                 445

Lys Arg Ser Asn Phe Lys Leu Trp Leu Asn Thr Ser Val Lys Arg Val
    450                 455                 460

Ile Arg Gln Gly Gly His Ile Thr Gly Val Glu Val Glu Pro Phe Arg
465                 470                 475                 480

Asp Gly Gly Tyr Gln Gly Ile Val Pro Val Thr Lys Val Thr Gly Arg
                485                 490                 495

Val Ile Leu Ser Ala Gly Thr Phe Gly Ser Ala Lys Ile Leu Leu Arg
            500                 505                 510

Ser Gly Ile Gly Pro Asn Asp Gln Leu Gln Val Val Ala Ala Ser Glu
        515                 520                 525

Lys Asp Gly Pro Thr Met Ile Ser Asn Ser Ser Trp Ile Asn Leu Pro
    530                 535                 540

Val Gly Tyr Asn Leu Asp Asp His Leu Asn Thr Asp Thr Val Ile Ser
545                 550                 555                 560

His Pro Asp Val Val Phe Tyr Asp Phe Tyr Glu Ala Trp Asp Asn Pro
                565                 570                 575

Ile Gln Ser Asp Lys Asp Ser Tyr Leu Asn Ser Arg Thr Gly Ile Leu
            580                 585                 590

Ala Gln Ala Ala Pro Asn Ile Gly Pro Met Phe Trp Glu Glu Ile Lys
        595                 600                 605

Gly Ala Asp Gly Ile Val Arg Gln Leu Gln Trp Thr Ala Arg Val Glu
    610                 615                 620

Gly Ser Leu Gly Ala Pro Asn Gly Lys Thr Met Thr Met Ser Gln Tyr
625                 630                 635                 640
```

```
Leu Gly Arg Gly Ala Thr Ser Arg Gly Arg Met Thr Ile Thr Pro Ser
                645                 650                 655

Leu Thr Thr Val Val Ser Asp Val Pro Tyr Leu Lys Asp Pro Asn Asp
            660                 665                 670

Lys Glu Ala Val Ile Gln Gly Ile Ile Asn Leu Gln Asn Ala Leu Lys
        675                 680                 685

Asn Val Ala Asn Leu Thr Trp Leu Phe Pro Asn Ser Thr Ile Thr Pro
    690                 695                 700

Arg Gln Tyr Val Asp Ser Met Val Val Ser Pro Ser Asn Arg Arg Ser
705                 710                 715                 720

Asn His Trp Met Gly Thr Asn Lys Ile Gly Thr Asp Asp Gly Arg Lys
                725                 730                 735

Gly Gly Ser Ala Val Val Asp Leu Asn Thr Lys Val Tyr Gly Thr Asp
            740                 745                 750

Asn Leu Phe Val Ile Asp Ala Ser Ile Phe Pro Gly Val Pro Thr Thr
        755                 760                 765

Asn Pro Thr Ser Tyr Ile Val Thr Ala Ser Glu His Ala Ser Ala Arg
    770                 775                 780

Ile Leu Ala Leu Pro Asp Leu Thr Pro Val Pro Lys Tyr Gly Gln Cys
785                 790                 795                 800

Gly Gly Arg Glu Trp Ser Gly Ser Phe Val Cys Ala Asp Gly Ser Thr
                805                 810                 815

Cys Gln Met Gln Asn Glu Trp Tyr Ser Gln Cys Leu
            820                 825


<210> SEQ ID NO 23
<211> LENGTH: 2364
<212> TYPE: DNA
<213> ORGANISM: Myceliophthora thermophila

<400> SEQUENCE: 23

atgaagctac tcagccgcgt tggggcgacc gccctagcgg cgacgttgtc actgcagcaa      60

tgtgcagccc agatgaccga ggggacctac accgatgagg ctaccggtat ccaattcaag     120

acgtggaccg cctccgaggg cgcccctttc acgtttggct tgaccctccc cgcggacgcg     180

ctggaaaagg atgccaccga gtacattggt ctcctgcgtt gccaaatcac cgatcccgcc     240

tcgcccagct ggtgcggtat ctcccacggc cagtccggcc agatgacgca ggcgctgctg     300

ctggtcgcct gggccagcga ggacaccgtc tacacgtcgt tccgctacgc caccggctac     360

acgctccccg gcctctacac gggcgacgcc aagctgaccc agatctcctc ctcggtcagc     420

gaggacagct tcgaggtgct gttccgctgc gaaaactgct tctcctggga ccaggatggc     480

accaagggca acgtctcgac cagcaacggc aacctggtcc tcggccgcgc cgccgcgaag     540

gatggtgtga cgggccccac gtgcccggac acggccgagt tcggtttcca tgataacggt     600

ttcggacagt ggggtgccgt gcttgagggt gctacttcgg actcgtacga ggagtgggct     660

aagctggcca cgaccacgcc cgagaccacc tgcgatggca ctggccccgg cgacaaggag     720

tgcgttccgg ctcccgagga cacgtatgat tacatcgttg tcggtgccgg cgccggtggt     780

atcaccgtcg ccgacaagct cagcgaggcc ggccacaagg tccttctcat cgagaaggga     840

ccccccttcga ccggcctgtg gaacgggacc atgaagcccg agtggctcga gagcaccgac     900

cttacccgct tcgacgttcc cggcctgtgc aaccagatct gggtcgactc tgccggcatc     960

gcctgcaccg ataccgacca gatggcgggc tgcgttctcg gcggtggcac cgctgtcaac    1020
```

-continued

```
gctggtttgt ggtggaagcc ccacccccgct gactgggatg agaacttccc cgaagggtgg   1080

aagtcgagcg atctcgcgga tgcgaccgag cgtgtcttca agcgcatccc cggcacgtcg   1140

cacccgtcgc aggacggcaa gttgtaccgc caggagggct tcgaggtcat cagcaagggc   1200

ctggccaacg ccggctggaa ggaaatcagc gccaacgagg cgcccagcga gaagaaccac   1260

acctatgcac acaccgagtt catgttctcg ggcggtgagc gtggcggccc cctggcgacg   1320

taccttgcct cggctgccga gcgcagcaac ttcaacctgt ggctcaacac tgccgtccgg   1380

agggccgtcc gcagcggcag caaggtcacc ggcgtcgagc tcgagtgcct cacggacggt   1440

ggcttcagcg ggaccgtcaa cctgaatgag ggcggtggtg tcatcttctc ggccggcgct   1500

ttcggctcgg ccaagctgct ccttcgcagc ggtatcggtc ctgaggacca gctcgagatt   1560

gtggcgagct ccaaggacgg cgagaccttc actcccaagg acgagtggat caacctcccc   1620

gtcggccaca acctgatcga ccatctcaac actgacctca ttatcacgca cccggatgtc   1680

gttttctatg acttctatgc ggcctgggac gagcccatca cggaggataa ggaggcctac   1740

ctgaactcgc ggtccggcat tctcgcccag gcggcgccca atatcggccc tatgatgtgg   1800

gatcaagtca cgccgtccga cggcatcacc cgccagttcc agtggacatg ccgtgttgag   1860

ggcgacagct ccaagaccaa ctcgacccac gccatgaccc tcagccagta cctcggccgt   1920

ggcgtcgtct cgcgcggccg gatgggcatc acctccgggc tgagcacgac ggtggccgag   1980

cacccgtacc tgcacaacaa cggcgacctg gaggcggtca tccaggggat ccagaacgtg   2040

gtggacgcgc tcagccaggt ggccgacctc gagtgggtgc tcccgccgcc cgacgggacg   2100

gtggccgact acgtcaacag cctgatcgtc tcgccggcca accgccgggc caaccactgg   2160

atgggcacgg ccaagctggg caccgacgac ggccgctcgg gcggcacctc ggtcgtcgac   2220

ctcgacacca aggtgtacgg caccgacaac ctgttcgtcg tcgacgcgtc cgtcttcccc   2280

ggcatgtcga cgggcaaccc gtcggccatg atcgtcatcg tggccgagca ggcggcgcag   2340

cgcatcctgg ccctgcggtc ttaa                                           2364
```

<210> SEQ ID NO 24
<211> LENGTH: 787
<212> TYPE: PRT
<213> ORGANISM: Myceliophthora thermophila

<400> SEQUENCE: 24

```
Met Lys Leu Leu Ser Arg Val Gly Ala Thr Ala Leu Ala Ala Thr Leu
1               5                   10                  15

Ser Leu Gln Gln Cys Ala Ala Gln Met Thr Glu Gly Thr Tyr Thr Asp
            20                  25                  30

Glu Ala Thr Gly Ile Gln Phe Lys Thr Trp Thr Ala Ser Glu Gly Ala
        35                  40                  45

Pro Phe Thr Phe Gly Leu Thr Leu Pro Ala Asp Ala Leu Glu Lys Asp
    50                  55                  60

Ala Thr Glu Tyr Ile Gly Leu Leu Arg Cys Gln Ile Thr Asp Pro Ala
65                  70                  75                  80

Ser Pro Ser Trp Cys Gly Ile Ser His Gly Gln Ser Gly Gln Met Thr
                85                  90                  95

Gln Ala Leu Leu Leu Val Ala Trp Ala Ser Glu Asp Thr Val Tyr Thr
            100                 105                 110

Ser Phe Arg Tyr Ala Thr Gly Tyr Thr Leu Pro Gly Leu Tyr Thr Gly
        115                 120                 125

Asp Ala Lys Leu Thr Gln Ile Ser Ser Ser Val Ser Glu Asp Ser Phe
```

```
    130                 135                 140

Glu Val Leu Phe Arg Cys Glu Asn Cys Phe Ser Trp Asp Gln Asp Gly
145                 150                 155                 160

Thr Lys Gly Asn Val Ser Thr Ser Asn Gly Asn Leu Val Leu Gly Arg
                165                 170                 175

Ala Ala Ala Lys Asp Gly Val Thr Gly Pro Thr Cys Pro Asp Thr Ala
            180                 185                 190

Glu Phe Gly Phe His Asp Asn Gly Phe Gly Gln Trp Gly Ala Val Leu
        195                 200                 205

Glu Gly Ala Thr Ser Asp Ser Tyr Glu Glu Trp Ala Lys Leu Ala Thr
    210                 215                 220

Thr Thr Pro Glu Thr Thr Cys Asp Gly Thr Gly Pro Gly Asp Lys Glu
225                 230                 235                 240

Cys Val Pro Ala Pro Glu Asp Thr Tyr Asp Tyr Ile Val Val Gly Ala
                245                 250                 255

Gly Ala Gly Gly Ile Thr Val Ala Asp Lys Leu Ser Glu Ala Gly His
            260                 265                 270

Lys Val Leu Leu Ile Glu Lys Gly Pro Pro Ser Thr Gly Leu Trp Asn
        275                 280                 285

Gly Thr Met Lys Pro Glu Trp Leu Glu Ser Thr Asp Leu Thr Arg Phe
    290                 295                 300

Asp Val Pro Gly Leu Cys Asn Gln Ile Trp Val Asp Ser Ala Gly Ile
305                 310                 315                 320

Ala Cys Thr Asp Thr Asp Gln Met Ala Gly Cys Val Leu Gly Gly Gly
                325                 330                 335

Thr Ala Val Asn Ala Gly Leu Trp Trp Lys Pro His Pro Ala Asp Trp
            340                 345                 350

Asp Glu Asn Phe Pro Glu Gly Trp Lys Ser Ser Asp Leu Ala Asp Ala
        355                 360                 365

Thr Glu Arg Val Phe Lys Arg Ile Pro Gly Thr Ser His Pro Ser Gln
    370                 375                 380

Asp Gly Lys Leu Tyr Arg Gln Glu Gly Phe Glu Val Ile Ser Lys Gly
385                 390                 395                 400

Leu Ala Asn Ala Gly Trp Lys Glu Ile Ser Ala Asn Glu Ala Pro Ser
                405                 410                 415

Glu Lys Asn His Thr Tyr Ala His Thr Glu Phe Met Phe Ser Gly Gly
            420                 425                 430

Glu Arg Gly Gly Pro Leu Ala Thr Tyr Leu Ala Ser Ala Ala Glu Arg
        435                 440                 445

Ser Asn Phe Asn Leu Trp Leu Asn Thr Ala Val Arg Arg Ala Val Arg
    450                 455                 460

Ser Gly Ser Lys Val Thr Gly Val Glu Leu Glu Cys Leu Thr Asp Gly
465                 470                 475                 480

Gly Phe Ser Gly Thr Val Asn Leu Asn Glu Gly Gly Gly Val Ile Phe
                485                 490                 495

Ser Ala Gly Ala Phe Gly Ser Ala Lys Leu Leu Leu Arg Ser Gly Ile
            500                 505                 510

Gly Pro Glu Asp Gln Leu Glu Ile Val Ala Ser Ser Lys Asp Gly Glu
        515                 520                 525

Thr Phe Thr Pro Lys Asp Glu Trp Ile Asn Leu Pro Val Gly His Asn
    530                 535                 540

Leu Ile Asp His Leu Asn Thr Asp Leu Ile Ile Thr His Pro Asp Val
545                 550                 555                 560
```

```
Val Phe Tyr Asp Phe Tyr Ala Ala Trp Asp Glu Pro Ile Thr Glu Asp
                565                 570                 575

Lys Glu Ala Tyr Leu Asn Ser Arg Ser Gly Ile Leu Ala Gln Ala Ala
            580                 585                 590

Pro Asn Ile Gly Pro Met Met Trp Asp Gln Val Thr Pro Ser Asp Gly
        595                 600                 605

Ile Thr Arg Gln Phe Gln Trp Thr Cys Arg Val Glu Gly Asp Ser Ser
    610                 615                 620

Lys Thr Asn Ser Thr His Ala Met Thr Leu Ser Gln Tyr Leu Gly Arg
625                 630                 635                 640

Gly Val Val Ser Arg Gly Arg Met Gly Ile Thr Ser Gly Leu Ser Thr
                645                 650                 655

Thr Val Ala Glu His Pro Tyr Leu His Asn Asn Gly Asp Leu Glu Ala
            660                 665                 670

Val Ile Gln Gly Ile Gln Asn Val Val Asp Ala Leu Ser Gln Val Ala
        675                 680                 685

Asp Leu Glu Trp Val Leu Pro Pro Pro Asp Gly Thr Val Ala Asp Tyr
    690                 695                 700

Val Asn Ser Leu Ile Val Ser Pro Ala Asn Arg Arg Ala Asn His Trp
705                 710                 715                 720

Met Gly Thr Ala Lys Leu Gly Thr Asp Asp Gly Arg Ser Gly Gly Thr
                725                 730                 735

Ser Val Val Asp Leu Asp Thr Lys Val Tyr Gly Thr Asp Asn Leu Phe
            740                 745                 750

Val Val Asp Ala Ser Val Phe Pro Gly Met Ser Thr Gly Asn Pro Ser
        755                 760                 765

Ala Met Ile Val Ile Val Ala Glu Gln Ala Ala Gln Arg Ile Leu Ala
    770                 775                 780

Leu Arg Ser
785


<210> SEQ ID NO 25
<211> LENGTH: 307
<212> TYPE: PRT
<213> ORGANISM: Artificial sequence
<220> FEATURE:
<223> OTHER INFORMATION: Synthetic polypeptide consensus sequence

<400> SEQUENCE: 25

Ala Pro Ser Pro Thr Thr Pro Ala Gly Cys Ala Ser Ala Val Thr Leu
1               5                   10                  15

Asp Ala Thr Asn Val Phe Tyr Thr Leu His Ala Asn Lys Phe Tyr Arg
            20                  25                  30

Ala Glu Val Glu Ala Ala Ala Ala Ala Ile Ser Asp Ser Ser Leu Ala
        35                  40                  45

Ala Ala Ala Lys Val Ala Asp Val Gly Thr Phe Leu Trp Leu Asp Thr
    50                  55                  60

Ile Ala Asn Ile Gly Lys Leu Glu Pro Ala Leu Asp Val Pro Cys Asp
65                  70                  75                  80

Gln Ile Leu Gly Leu Val Ile Tyr Asp Leu Pro Gly Arg Asp Cys Ala
                85                  90                  95

Ala Lys Ala Ser Asn Gly Glu Leu Ala Val Gly Glu Leu Asp Arg Tyr
            100                 105                 110

Lys Thr Glu Tyr Ile Asp Pro Ile Val Ala Ile Leu Lys Tyr Pro Asn
        115                 120                 125
```

-continued

```
Thr Ala Ile Ala Leu Val Ile Glu Pro Asp Ser Leu Pro Asn Leu Lys
    130                 135                 140

Pro Gly Ala Glu Leu Ala Lys Val Tyr Lys Ala Ala Gly Ser Pro Lys
145                 150                 155                 160

Gln Val Arg Gly Ile Ala Thr Asn Val Ala Gly Trp Asn Ala Trp Asp
                165                 170                 175

Leu Ser Pro Gly Glu Phe Ser Ala Ser Asp Ala Lys Tyr Asn Lys Cys
            180                 185                 190

Gln Asn Glu Lys Leu Tyr Ile Phe Gly Pro Leu Lys Ser Ala Gly Met
        195                 200                 205

Pro Asn His Ala Ile Val Asp Thr Gly Arg Asn Gly Val Thr Gly Leu
    210                 215                 220

Arg Glu Glu Trp Gly Trp Cys Asn Val Asn Gly Ala Gly Phe Gly Val
225                 230                 235                 240

Arg Pro Thr Ala Thr Gly Glu Leu Ala Asp Ala Phe Val Trp Val Lys
                245                 250                 255

Pro Gly Gly Glu Ser Asp Gly Thr Ser Asp Ser Ser Ala Thr Arg Tyr
            260                 265                 270

Asp Ser Phe Cys Gly Lys Ser Asp Ala Tyr Lys Pro Ser Pro Glu Ala
        275                 280                 285

Gly Gln Trp Asn Gln Ala Tyr Phe Glu Met Leu Leu Lys Asn Ala Lys
    290                 295                 300

Pro Ala Phe
305


<210> SEQ ID NO 26
<211> LENGTH: 17
<212> TYPE: PRT
<213> ORGANISM: Myceliophthora thermophila

<400> SEQUENCE: 26

Met Lys Phe Val Gln Ser Ala Thr Leu Ala Phe Ala Ala Thr Ala Leu
1               5                   10                  15

Ala
```